US007901873B2

(12) United States Patent
Nicholson et al.

(10) Patent No.: US 7,901,873 B2
(45) Date of Patent: Mar. 8, 2011

(54) METHODS FOR THE DIAGNOSIS AND TREATMENT OF BONE DISORDERS

(75) Inventors: Jeremy Kirk Nicholson, Croydon (GB); Elaine Holmes, London (GB); John Christopher Lindon, Westerham (GB); Joanne Tracey Brindle, Watchfield (GB); David John Grainger, Cambridge (GB)

(73) Assignee: TCP Innovations Limited, Cambridge (GB)

(*) Notice: Subject to any disclaimer, the term of this patent is extended or adjusted under 35 U.S.C. 154(b) by 1224 days.

(21) Appl. No.: 10/475,791

(22) PCT Filed: Apr. 23, 2002

(86) PCT No.: PCT/GB02/01909
§ 371 (c)(1),
(2), (4) Date: Jul. 12, 2004

(87) PCT Pub. No.: WO02/086502
PCT Pub. Date: Oct. 31, 2002

(65) Prior Publication Data
US 2004/0241743 A1    Dec. 2, 2004

Related U.S. Application Data

(60) Provisional application No. 60/307,015, filed on Jul. 20, 2001.

(30) Foreign Application Priority Data

Apr. 23, 2001 (GB) .................................. 0109930.8
Jul. 17, 2001 (GB) .................................. 0117428.3

(51) Int. Cl.
*G01N 33/53* (2006.01)

(52) U.S. Cl. .............................................. 435/4; 435/25
(58) Field of Classification Search ............... 436/96, 436/17, 173, 174; 324/300, 308, 318, 321; 435/4, 25
See application file for complete search history.

(56) References Cited

U.S. PATENT DOCUMENTS

| 4,510,450 | A | 4/1985 | Brown |
| 4,635,643 | A | 1/1987 | Brown |
| 5,769,074 | A | 6/1998 | Barnhill et al. |
| 6,683,455 | B2 | 1/2004 | Ebbels et al. |
| 2002/0145425 | A1 | 10/2002 | Ebbels et al. |
| 2004/0142496 | A1 | 7/2004 | Nicholson et al. |

(Continued)

FOREIGN PATENT DOCUMENTS

JP    2000-298128 A    10/2000

(Continued)

OTHER PUBLICATIONS

A Microtitre Format Assay for Proline in Human Serum or Plasma David J. Grainger, Sri Aitken Clinica Chimica Acta 343 (2004) 113-118.*

(Continued)

*Primary Examiner* — Jill Warden
*Assistant Examiner* — Dwan A Gerido
(74) *Attorney, Agent, or Firm* — Morrison & Foerster LLP

(57) ABSTRACT

This invention pertains to chemometric methods for the analysis of chemical, biochemical, and biological data, for example, spectral data, for example, nuclear magnetic resonance (NMR) spectra, and their applications, including, e.g., classification, diagnosis, prognosis, etc., especially in the context of bone disorders, e.g., conditions associated with low bone mineral density, e.g., osteoporosis.

22 Claims, 5 Drawing Sheets

U.S. PATENT DOCUMENTS

| | | | |
|---|---|---|---|
| 2004/0214348 | A1 | 10/2004 | Nicholson et al. |
| 2004/0241743 | A1 | 12/2004 | Nicholson et al. |
| 2005/0037515 | A1 | 2/2005 | Nicholson et al. |
| 2005/0074745 | A1 | 4/2005 | Clayton et al. |
| 2005/0130321 | A1 | 6/2005 | Nicholson et al. |
| 2006/0073611 | A1 | 4/2006 | Grainger et al. |

FOREIGN PATENT DOCUMENTS

| | | | |
|---|---|---|---|
| WO | WO-91/10128 | A1 | 7/1991 |
| WO | WO-93/21517 | A1 | 10/1993 |
| WO | WO-97/48331 | A1 | 12/1997 |
| WO | WO-99/45842 | A1 | 9/1999 |
| WO | WO-00/42915 | A1 | 7/2000 |
| WO | WO-00/65366 | A1 | 11/2000 |
| WO | WO-00/72031 | A1 | 11/2000 |
| WO | WO-00/72038 | A1 | 11/2000 |
| WO | WO-02/085195 | A2 | 10/2002 |
| WO | WO-02/085195 | A3 | 10/2002 |
| WO | WO-02/086478 | A2 | 10/2002 |
| WO | WO-02/086478 | A3 | 10/2002 |
| WO | WO-02/086500 | A2 | 10/2002 |
| WO | WO-02/086500 | A3 | 10/2002 |
| WO | WO-02/086501 | A2 | 10/2002 |
| WO | WO-02/086501 | A3 | 10/2002 |
| WO | WO-02/086502 | A2 | 10/2002 |

OTHER PUBLICATIONS

Adams, E. et al. (1980). "Metabolism of Proline and the Hydroxprolines," *Ann. Rev. Bio.* 49:1005-1061.

Ala-Korpela, M. (1995). "¹HNMR Spectroscopy of Human Blood Plasma," *Progress in Nuclear Magnetic Resonance Spectroscopy* 27:475-554.

Ala-Korpela, M. et al. (1995). "Quantification of Biomedical NMR Data using Artificial Neural Network Analysis: Lipoprotein Lipid Profiles from $^1$H NMR Data of Human Plasma," *NMR in Biomedicine* 8:235-244.

Andersson, C.A. (1999). "Direct Orthogonalization," *Chemonmetrics and Intelligent Laboratory Systems* 47:51-63.

Anker, L. et al. (1992). "Prediction of Carbon-13 Nuclear Magnetic Resonance Chemical Shifts by Artificial Neural Networks," *Anal. Chem.* 64:1157-1164.

Anthony, M.L. et al., (1994). "Pattern Recognition Classification of the Site of Nephrotoxicity Based on Metabolic Data Derived from Proton Nuclear Magnetic Resonance Spectra of Urine," *Molecular Pharmacology* 46:199-211.

Anthony, M.L. et al. (1995). "Classification of Toxin-Induced Changes in $^1$H NMR Spectra of Urine Using an Artificial Neural Network," *Journal of Pharmaceutical & Biomedical Analysis* 13(3):205-211.

Beckwith-Hall, B.M. et al. (1998). "Nuclear Magnetic Resonance Spectroscopic and Principal Components Analysis Investigation into Biochemical Effects of Three Model Hepatotoxins," *Chem. Res. Toxicol.* 11:260-272.

Berman, J.L. et al. (Sep. 1978). "A Multivariate Approach for Interpreting Treadmill Exercise Tests in Coronary Artery Disease," *Circulation* 58(3):505-512.

Berman, J.W. et al. (Apr. 15, 1996). "Localization of Monocyte Chemoattractant Peptide-1 Expression in the Central Nervous System in Experimental Autoimmune Encephalomyelitis and Trauma in the Rat," *J. of Immunol.* 156(8):3017-3023.

Bishop, C.M. (1995). *Neural Networks for Pattern Recognition*, Oxford University Press, Inc.: New York, NY, pp. xiv-xvii (Table of Contents Only.).

Boctor, F.N. (1971). "An Improved Method for Colorimetric Determination of Proline with Isatin," *Analytical Biochemistry* 43:66-70.

Breslow, J.L. (Sep. 1993). "Transgenic Mouse Models of Lipoprotein Metabolism and Atherosclerosis," *Proc. Natl. Acad. Sci. USA* 90:8314-8318.

Bretthorst, G.L. et al. (1988). "Bayesian Analysis of Time-Domain Magnetic Resonance Signals," *Journal of Magnetic Resonance* 79:369-376.

Bretthorst, G.L. (1990). "Bayesian Analysis. II. Signal Detection and Model Selection," *Journal of Magnetic Resonance* 88:552-570.

Bretthorst, G.L. (1990). "Bayesian Analysis. III. Applications to NMR Signal Detection, Model Selection, and Parameter Estimation," *Journal of Magnetic Resonance* 88:571-595.

Bro, R. (1997). "PARAFAC. Tutorial and Applications," *Chemometrics and Intelligent Laboratory Systems* 38:149-171.

Broomhead, D.S. et al. (1998) "Multivariable Function Interpolation and Adaptive Networks," *Complex Systems* 2:321-355.

Brown, T.R. et al. (1996). "NMR Spectral Quantitation by Principal-Component Analysis. II. Determination of Frequency and Phase Shifts," *Journal of Magnetic Resonance, Series B* 112:32-43.

Bruce, R.A. (Oct. 1974). Value of the Balke Protocol, *American Heart Journal* 88(4):533-534.

Collins, F.S. et al. (Feb. 7, 2001). "Implications of the Human Genome Project for Medical Science," *Journal of the American Medical Association* 285(5):540-544.

Confort-Gouny, S. et al. (1992). "Metabolic Characterization of Neurological Diseases by Proton Localized NMR Spectroscopy of the Human Brain," *C. R. Acad. Sci. III* 315:287-293.

Contasta, I. et al. (2001). "Cell Cycle Control in Cellular Homeostasis During the Immune Response: Interactions Between TH1, TH2 Cytokines, and Bc12 and p53 Molecules," *Cancer Biotherapy & Radiopharmaceuticals* 16(1):63-71.

Cullen, P. et al. (1998). "Lipoproteins and Cardiovascular Risk—from Genetics to CHD Prevention," *European Heart Journal* 19(Suppl. C):C5-C11.

Després, J-P. et al. (2000). "HDL-Cholesterol as a Marker of Coronary Heart Disease Risk: The Québec Cardiovascular Study," *Atherosclerosis* 153:263-272.

Dolecek, T.A. et al. (Jun. 1986). "A Long-Term Nutrition Intervention Experience: Lipid Responses and Dietary Adherence Patterns in the Multiple Risk Factor Intervention Trial," *Journal of the American Dietetic Association* 86(6):752-758.

Dutt, M.J. et al. (2000). "Proteomic Analysis," *Current Opinion in Biotechnology* 11:176-179.

Dvorak, A.M. et al. (Aug. 1996)."Comparative Ultrastructural Morphology of Human Basophils Stimulated to Release Histamine by Anti-IgE, Recombinant IgE-Dependent Histamine-Releasing Factor, or Monocyte Chemotactic Protein-1," *J. Allergy Clin. Immunol.* 98(2):355-370.

Enesenat, D. et al. (2001). "Transforming Growth Factor-β1 Stimulates Vascular Smooth Muscle Cell L-Proline Transport by Inducing System A Amino Acid Transporter 2 (SAT2) Gene Expression," *Biochem. J.* 360:507-512.

European Search Report mailed Jan. 19, 2007, for European Application No. 02720254.8 filed on Apr. 23, 2002, nine pages.

European Search Report mailed Aug. 24, 2007, for European Application No. 02720251.4 filed on Apr. 23, 2002, seven pages.

European Search Report mailed Feb. 28, 2008, for European Application No. 02718382.1 filed on Apr. 23, 2002, four pages.

Fan, T. W-M. (1996). "Metabolite Profiling by One—and Two-Dimensional NMR Analysis of Complex Mixtures," *Progress in Nuclear Magnetic Resonance Spectroscopy* 28:161-219.

Farrant, R.D. et al. (1992). "An Automatic Data Reduction and Transfer Method to Aid Pattern Recognition Analysis and Classification of NMR Spectra," *Journal of Pharmaceutical & Biomedical Analysis* 10(2/3):141-144.

Fearn, T. (2000). "On Orthogonal Signal Correction," *Chemometrics and Intelligent Laboratory Systems* 50:47-52.

Fiehn, O. et al. (Nov. 2000). "Metabolite Profiling for Plant Functional Genomics," *Nature Biotechnology* 18:1157-1161.

Felson, D.T. et al. (Oct. 17, 2000). "Osteoarthritis: New Insights. Part 1: The Disease and Its Risk Factors," *Annals of Internal Medicine* 133(8):635-646.

Felson, D.T. et al. (Aug. 1998). "An Update on the Epidemiology of Knee and Hip Osteoarthritis with a View to Prevention," *Arthritis & Rheumatism* 41(8):1343-1355.

Frank, I.E. et al. (1984). "Prediction of Product Quality from Special Data Using the Partial Least-Squares Method," *J. Chem. Inf. Comput. Sci.* 24:20-24.

Garnero, P. et al. (1996). "Markers of Bone Resorption Predict Hip Fracture in Elderly Women: The EPISOD Prospective Study," *Journal of Bone and Mineral Research* 11(10):1531-1538.

Garrod, S. et al. (2001). "High-Resolution $^1$H NMR and Magic Angle Spinning NMR Spectroscopic Investigation of the Biochemical Effects of 2-Bromoethanamine in Intact Renal and Hepatic Tissue," *Magnetic Resonance in Medicine* 45:781-790.

Gartland, K.P.R. et al. (1990). "A Pattern Recognition Approach to the Comparison of PMR and Clinical Chemical Data for Classification of Nephrotoxicity," *Journal of Pharmaceutical & Biomedical Analysis* 8(8-12):963-968.

Gartland, K.P.R. et al. (1990). "Pattern Recognition Analysis of High Resolution $^1$H NMR Spectra of Urine. A Nonlinear Mapping Approach to the Classification of Toxicological Data," *NMR in Biomedicine* 3(4):166-172.

Gartland, K.P.R. et al. (1991). "Application of Pattern Recognition Methods to the Analysis and Classification of Toxicological Data Derived from Proton Nuclear Magnetic Resonance Spectroscopy of Urine," *Molecular Pharmacology* 39:629-642.

Geisow, M.J. (Feb. 1998). "Proteomics: One Small Step for a Digital Computer, One Giant Leap for Humankind," *Nature Biotechnology* 16:206.

Ghirnikar, R.S. et al. (1996). "Rapid Communication: Chemokine Expression in Rat Stab Wound Brain Injury," *Journal of Neuroscience Research* 46:727-733.

Gong, J-H. et al. (Jul. 7, 1997). "An Antagonist of Monocyte Chemoattractant Protein 1 (MCP-1) Inhibits Arthritis in the MRL-*lpr* Mouse Model," *J. Exp. Med.* 186(1):131-137.

Guccione, A.A. et al. (Mar. 1994). "The Effects of Specific Medical Conditions on the Functional Limitations of Elders in the Framingham Study," *American Journal of Public Health* 84(3):351-358.

Gygi, S.P. et al. (Mar. 1999). "Correlation between Protein and mRNA Abundance in Yeast," *Molecular and Cellular Biology* 19(3):1720-1730.

Hare, B.J. et al. (1994). "Application of Neural Networks to Automated Assignment of NMR Spectra of Proteins," *Journal of Biomolecular NMR* 4:35-46.

Hiltunen, Y. et al. (1995). "Lipoprotein-Lipid Quantification by Neural-Network Analysis of $^1$H NMR Data from Human Blood Plasma," *Journal of Magnetic Resonance, Series B* 106:191-194.

Holmes, E. et al. (1998). "Development of a Model for Classification of Toxin-Induced Lesions Using $^1$H NMR Spectroscopy of Urine Combined with Pattern Recognition," *NMR in Biomedicine* 11:235-244.

Holmes, E. et al. (1998). "The Identification of Novel Biomarkers of Renal Toxicity Using Automatic Data Reduction Techniques and PCA of Proton NMR Spectra Urine," *Chemometrics and Intelligent Laboratory Systems* 44:245-255.

Holmes, E. et al. (1992). "Nuclear Magnetic Resonance Spectrometry and Pattern Recognition Analysis of the Biochemical Processes Associated with the Progression of and Recovery from Nephrotoxic Lesions in the Rat Induced by Mercury (II) Chloride and 2-Bromoethanamine," *Molecular Pharmacology* 42:922-930.

Holmes, E. et al. (1994). "Automatic Data Reduction and Pattern Recognition Methods for Analysis of $^1$H Nuclear Magnetic Resonance Spectra of Human Urine from Normal and Pathological States," *Analytical Biochemistry* 220:284-296.

Howells, S.L. et al. (1993). "Pattern Recognition of $^{31}$P Magnetic Resonance Spectroscopy Tumour Spectra Obtained In Vivo," *NMR in Biomedicine* 6:237-241.

Hughes, D.E. et al. (Jun. 1997). "Apoptosis in Bone Physiology and Disease," *J. Clin. Pathol.: Mol. Pathol.* 50(3):132-137.

Iida, K. at al. (1997). "Analysis of T Cell Subsets and βeta Chemokines in Patients with Pulmonary Sarcoidosis," *Thorax* 52:431-437.

Insko, E.K. at al. (1999). "Sodium NMR Evaluation of Articular Cartilage Degradation," *Magnetic Resonance in Medicine* 41:30-34.

International Preliminary Examination Report mailed on Oct. 23, 2003 for International Application No. PCT/GB02/01909, filed on Apr. 23, 2002, four pages.

Isles, C.G. et al. (Sep. 2000). "Identifying Patients at risk for Coronary Heart Disease: Implications from Trials of Lipid-Lowering Drug Therapy," *Q. J. Med.* 93(9):567-574.

Jöreskog, K.G. et al. (1982). *Systems Under Indirect Observation Causality Structure Prediction Part I*, North-Holland Publishing Company: Amsterdam, Netherlands, pp. xvii-xx (Table of Contents Only.).

Kawai, A. et al. (Jan. 15, 1998). "*SYT-SSX* Gene Fusion as a Determinant of Morphology and Prognosis in Synovial Sarcoma," *N. Eng. J. Med.* 338(3):153-160.

Kjelsberg, M.O. (1986). "Relationship Between Baseline Risk Factors and Coronary Heart Disease and Total Mortality in the Multiple Risk Factor Intervention Trial," *Preventive Medicine* 15:254-273.

Kjelsberg, M.O. et al. (1997). "Chapter 2. Brief Description of the Multiple Risk Factor Intervention Trial," *Am. J. Clin. Nutr.* 65(Suppl.):191S-195S.

Klenk, H-P. et al. (Nov. 27, 1997). "The Complete Genome Sequence of the Hyperthermolphilic, Sulphate-Reducing Archaeon *Archaeoglobus fulgidus*," *Nature* 390:364-370.

Kuesel, A.C. et al. (1996). "Quantitation of Resonance in Biological $^{31}$P NMR Spectra via Principal Component Analysis: Potential and Limitations," *NMR in Biomedicine* 9:93-104.

Kuller, L.H. et al. (1991). "Cigarette Smoking and Mortality," *Preventive Medicine* 20:638-654.

Kvalheim, O.M. et al. (1989). "Interpretation of Latent-Variable Regression Models," *Chemometrics and Intelligent Laboratory Systems* 7:39-51.

Lamers, R.J.A.N. et al. (2005). "Identification of an Urinary Metabolite Profile Associated with Osteoarthritis," *OsteoArthritis and Cartilage* 13:762-768.

Lindon, J.C. et al. (1980). "Digitsation and Data Processing in Fourier Transform NMR," *Progress in NMR Spectroscopy* 14:27-66.

Lindon, J.C. et al. (1990). "NMR Spectroscopy of Biofluids," *Annual Reports on NMR Spectroscopy* 38:1-88.

Lindon, J.C. et al. (2001). "Pattern Recognition Methods and Applications in Biomedical Magentic Resonance," *Progress in Nuclear Magnetic Resonance Spectroscopy* 39:1-40.

Martin, G.J. (1998). "Recent Advances in Site-Specific Natural Isotope Fractionation Studied by Nuclear Magnetic Resonance," *Isotopes Environ. Health Stud.* 34:233-243.

Martin, M.L. et al. (1999). "Site-Specific Isotope Effects and Origin Inference," *Analusis* 27(3):209-213.

Martin, T.R. et al. (Apr. 1989). "Role of Mast Cells in Anaphylaxis. Evidence for the Importance of Mast Cells in the Cardiopulmonary Alterations and Death Induced by Anti-IgE in Mice," *J. Clin. Invest.* 83:1375-1383.

Mazzucchelli, L. (1996). "Differential In Situ Expression of the Genes Encoding the Chemokines MCP-1 and Rantes in Human Inflammatory Bowel Disease," *Journal of Pathology* 178:201-206.

McIlvain, H.E. (1992). "Application of the MRFIT Smoking Cessation Program to a Healthy, Mixed-Sex Sample," *Am. J. Prev. Med.* 8(3):165-170.

Melton, III, L.J. et al. (1992). "How Many Women Have Osteoporosis?," *Journal of Bone and Mineral Research* 7(9):1005-1010.

Moka, D. et al. (1998). "Biochemical Classification of Kidney Carcinoma Biopsy Samples Using Magic-Angle-Spinning $^1$H Nuclear Magnetic Resonance Spectroscopy," *Journal of Pharmaceutical and Biomedical Analysis* 17:125-132.

Morvan, D. et al. (1990). "Discriminant Factor Analysis of $^{31}$P NMR Spectroscopic Data in Myopathies," *Magnetic Resonance in Medicine* 13:216-227.

Nicholson, J.K. et al. (1989). "High Resolution Proton Magnetic Resonance Spectroscopy of Biological Fluids," *Progress in NMR Spectroscopy* 21:449-501.

Nicholson, J.K. et al. (Mar. 1, 1995). "750 MHz $^1$H and $^1$H-$^{13}$C NMR Spectroscopy of Human Blood Plasma," *Anal. Chem.* 67(5):793-811.

Nicholson, J.K. et al. (1999). "'Metabononmics': Understanding the Metabolic Reponses of Living Systems to Pathophysiological Stimuli via Multivariate Statistical Analysis of Biological NMR Spectroscopic Data," *Xenobiotica* 29(11):1181-1189.

Nilsson, N.J. (1965). *Learning Machines. Foundations of Trainable Pattern-Classifying Systems*, McGraw-Hill Book Company: New York, NY, pp. vii-xi (Table of Contents Only.).

Ogata, H. et al. (1997). "The Role of Monocyte Chemoattractant Protein-1 (MCP-1) in the Pathogenesis of Collagen-Induced Arthritis in Rats," *Journal of Pathology* 182:106-114.

Parzen, E. (Sep. 1962). "On Estimation of a Probability Density Function and Mode," *The Annals of Mathematical Statistics* 33(3):1065-1076.

Patterson, D.W. (1996). *Artificial Neural Networks: Theory and Applications*, Prentice Hall: Singapore, pp. vii-xi (Table of Contents Only.).

Pellegrini, P. et al. (2000). "Simultaneous Measurement of Soluble Carcinoembryonic Antigen and Tissue Inhibitor of Metalloproteinase TIMP1 Serum Levels for Use as Markers of Pre-Invasive to Invasive Colorectal Cancer," *Cancer Immunol. Immunother.* 49:388-394.

Plump, A.S. et al. (Oct. 16, 1992). "Severe Hypercholesterolemia and Atherosclerosis in Apolipoprotein E-Deficient Mice Created by Homologous Recombination in ES Cells," *Cell* 71:343-353.

Pocock, N.A. et al. (Oct. 2, 2000). "Potential Roles for Quantitative Ultrasound in the Management of Osteoporosis," *Med. J. Aust.* 173:355-358.

Press, W.H. et al. (1988). *Numerical Recipes in C: The Art of Scientific Computing,* Cambridge University Press, New York, NY, pp. v-x (Table of Contents Only.).

Prince, R.L. (2001). "How to Diagnose the Presence of Osteoporosis and Assess the Risk of Fracture," *Best Practice and Research Clinical Rheumatology* 15(3):345-358.

Promislow, J.H.E. (2002). "Protein Consumption and Bone Mineral Density in the Elderly," *American Journal of Epidemiology* 155(7):636-644.

Quinlan, J.R. (1986). "Induction of Decision Trees," *Machine Learning* 1:81-106.

Raisz, L.G. (Mar. 31, 1988). "Local and Systemic Factors in the Pathogenesis of Osteoporosis," *N. Eng. J. Med.* 318(13):818-828.

Ross, R. (Jan. 14, 1999). "Atherosclerosis—An Inflammatory Disease," *N. Engl. J. Med.* 340(2):115-126.

Sach, M. et al. (Feb. 1997). "Inverse MCP-1/IL-8 Ration in Effluents of CAPS Patients with Peritonitis and in Isolated Cultured Human Peritoneal Macrophages," *Nephroi. Dial. Transplant.* 12(2):315-320.

Sato, M. et al. (2000). "Three-Dimensional Modeling of the Effects of Parathyroid Hormone on Bone Distribution in Lumbar Vertebrae of Ovariectomized Cynomolgus Macaques," *Osteoporosis Int.* 11:871-880.

Sjöström, M. et al. (1986). "PLS Discriminant Plots," *Pattern Recognition in Practice II*, Gelsema, E.S. ed. et al., Elsevier Science Publishers B.V.: North-Holland, Netherlands, pp. 461-470.

Somorjai, R.L. et al. (Feb. 1995). "Computerized Consensus Diagnosis: A Classification Strategy for the Robust Analysis of MR Spectra. I. Applications to $^1$H Spectra of Thyroid Neoplasms," *Magn. Reson. Med.* 33(2):257-263.

Specht, D.F. (1990). "Probabilistic Neural Networks," *Neural Networks* 3:109-118.

Spraul, M. et al. (1994). "Automatic Reduction of NMR Spectroscopic Data for Statistical and Pattern Recognition Classification of Samples," *Journal of Pharmaceutical & Biomedical Analysis* 12(10):1215-1225.

Ståhle, L. et al. (1987). "Partial Least Squares Analysis with Cross-Validation for the Two-Class Problem: A Monte Carlo Study," *Journal of Chemometrics* 1:185-196.

Stein, W.H. et al. (Mar. 1954). "The Amino Acid Content of the Blood and Urine in Wilson's Disease," *J. Clin. Invest.* 33(3):410-419.

Stein, W.H. et al. (Dec. 1954). "The Free Amino Acids of Human Blood Plasma," *J. Biol. Chem.* 211(2):915-926.

Stoyanova, R. et al. (1995). "Application of Principal-Component Analysis for NMR Spectral Quantitation," *J. Magn. Reson. A.* 115:265-269.

Sugiyama, Y. et al. (1995). "Chemokines in Bronchoalveolar Lavage Fluid in Summer-Type Hypersensitivity Pneumonitis," *Eur. Respir. J.* 8:1084-1090.

Sun, J. (1997). "Statistical Analysis of NIR Data: Data Pretreatment," *Journal of Chemometrics* 11:525-532.

Sze, D.Y. et al. (1994). "High-Resolution Proton NMR Studies of Lymphocyte Extracts," *Immunomethods* 4:113-126.

Tanaka, Y. et al. (Jul. 1986). "Evaluation of Hepatic Fibrosis by Serum Proline and Amino-Terminal Type III Procollagen Peptide Levels in Alcoholic Patients," *Digestive Diseases and Sciences* 31(7):712-717.

Tomlins, A.M. et al. (Mar. 1998). "High Resolution Magic Angle Spinning $^1$H Nuclear Magnetic Resonance Analysis of Intact Prostatic Hyperplastic and Tumour Tissues," *Analytical Communications* 35:113-115.

Tranter, G. et al. (1999). "Metabonomic Prediction of Drug Toxicity via Probabilistic Neural Networks Analysis of NMR Biofluid Data," Abstract, presented at the $9^{th}$ North American ISSX Meeting, Nashville, TN, Oct. 24-28, 1998, four pages.

Volejnikova, S. et al. (May 1997). "Monocyte Recruitment and Expression of Monocyte Chemoattractant Protein-1 are Developmentally Regulated in Remodeling Bone in the Mouse," *American Journal of Pathology* 150(5):1711-1721.

Wasserman, P.D. (1989). *Neural Computing. Theory and Practice.* Van Nostrand Reinhold: New York, NY, pp. v-vi (Table of Contents Only.).

Weber, O.M. et al. (May 1998). "Heuristic Optimization Algorithms Applied to the Quantification of Spectroscopic Data," *Magn. Reson. Med.* 39(5):723-730.

Westerhuis, J.A. (2001). "Direct Orthogonal Signal Correction," *Chemometrics and Intelligent Laboratory Systems* 56:13-25.

Wise, B.M. et al. (2001). "Orthogonal Signal Correction," located at <http://www.eigenvector.com/MATLAB/OSC.html>, last visited on Mar. 27, 2008, three pages.

Wold, H. (1966). "Estimation of Principal Components and Related Models by Interative Least Squares," *Multivariate Analysis*, Krishnaiah, P.R. ed., Academic Press: New York, NY, pp. 391-420.

Wold, S. (1976). "Pattern Recognition by Means of Disjoint Principal Components Models," *Pattern Recognition* 8:127-139.

Wold, S. et al. (1998). "Orthogonal Signal Correction of Near-Infrared Spectra," *Chemometrics and Intelligent Laboratory Systems* 44:175-185.

Wold, S. et al. (1998). "Modelling and Diagnostics of Batch Processes and Analogous Kinetic Experiments," *Chemometrics and Intelligent Laboratory Systems* 44:331-340.

Yokode, M. et al. (Nov. 30, 1990). "Diet-Induced Hypercholesterolemia in Mice: Prevention by Overexpression of LDL Receptors," *Science* 250(4985):1273-1275.

Zeyneloglu, H.B. (Aug. 1998). "The Effect of Monocyte Chemotactic Protein 1 in Intraperitoneal Adhesion Formation in a Mouse Model," *Am. J. Obstet. Gynecol.* 179(2):438-443.

Zheng, M.H. et al. (1998). "Gene Expression of Monocyte Chemoattractant Protein-1 in Giant Cell Tumors of Bone Osteoclastoma: Possible Involvement in CD68+ Macrophage-Like Cell Migration," *Journal of Cellular Biochemistry* 70:121-129.

Declaration of Non-Establishment of International Search Report mailed Jan. 17, 2003, for PCT Application No. PCT/GB02/01909 filed Apr. 23, 2002, two pages.

Gavaghan, C.L. et al. (2001, e-published Mar. 16, 2001). "Directly Coupled High-Performance Liquid Chromatography and Nuclear Magnetic Resonance Spectroscopic with Chemometric Studies on Metabolic Variation in Sprague-Dawley Rats," *Anal. Biochem.* 291:245-252.

Haybittle, J.L. et al. (1982). "A Prognostic Index in Primary Breast Cancer," *Br. J. Cancer* 45:361-366.

Holmes, E. et al. (2001, e-published Jan. 23, 2001). "Metabonomic Characterization of Genetic Variations in Toxicological and Metabolic Responses Using Probabilistic Neural Networks," *Chem. Res. Toxicol.* 14(2):182-191.

International Search Report mailed Dec. 11, 2002, for PCT Application No. PCT/GB02/01928, filed Apr. 23, 2002, six pages.

International Search Report mailed Dec. 12, 2002, for PCT Application No. PCT/GB02/01862, filed Apr. 23, 2002, 12 pages.

International Search Report mailed Dec. 12, 2002, for PCT Application No. PCT/GB02/01881, filed Apr. 23, 2002, four pages.

International Search Report mailed Apr. 9, 2003, for PCT Application No. PCT/GB02/01854, filed Apr. 23, 2002, six pages.

Morris, P.G. (1986). *Nuclear Magnetic Resonance Imaging in Medicine and Biology*, Clarendon Press: Oxford, pp. 296-297.

Non-Final Office Action dated Jun. 4, 2007, for U.S. Appl. No. 10/475,765, filed Oct. 22, 2003, seven pages.

Non-Final Office Action dated Feb. 19, 2008, for U.S. Appl. No. 10/475,765, filed Oct. 22, 2003, eight pages.

Requirement for Restriction/Election dated Sep. 4, 2008, for U.S. Appl. No. 10/475,734, filed Nov. 29, 2004, ten pages.

Christiansen, C. (Nov. 1995). "Osteoporosis: Diagnosis and Management Today and Tomorrow," *BONE* Supplement 17(5):513S-516S.

European Examination Report mailed on Aug. 17, 2009 for EP Application No. 02720254.8, filed on Apr. 23, 2002, eight pages.

Link, T.M. et al. (1998). "A Comparative Study of Trabecular Bone Properties in the Spine and Femur Using High Resolution MRI and CT," *Journal of Bone and Mineral Research* 13(1):122-132.

Final Office Action mailed Oct. 21, 2008, for U.S. Appl. No. 10/475,765, filed Oct. 22, 2003, 12 pages.

Chung, H. et al. (Nov. 1993). "Relationship Between NMR Transverse Relaxation, Trabecular Bone Architecture, and Strength," *Proc. Natl. Acad. Sci. USA* 90:10250-10254.

Fish, F.E. et al. (1991). "Functional Correlates of Differences in Bone Density Among Terrestrial and Aquatic Genera in the Family Mustelidae (Mammalia)," *Zoomorphology* 110:339-345.

Glasbey, C.A. et al. (Aug. 2, 2001). "The Application of Multivariate Statistical Methods to NMR Imaging," *Computers and Electronics in Agriculture* 32(2):85-100.

James, G.M. et al. (Mar. 1, 2001). "Principal Component Models for Sparse Functional Data," located at <http://www-stat.stanford.edu/~hastie/Papers/fpc.ps> last visited on May 29, 2007, 22 pages.

Weinstein, L. et al. (May 1999). "A Simple System to Determine Who Needs Osteoporosis Screening," *Obstetrics & Gynecology* 93(5-Pt. 1):757-760.

Non-Final Office Action mailed Oct. 2, 2008, for U.S. Appl. No. 10/475,573, filed Apr. 23, 2002, 12 pages.

\* cited by examiner

Figure 1A-OP
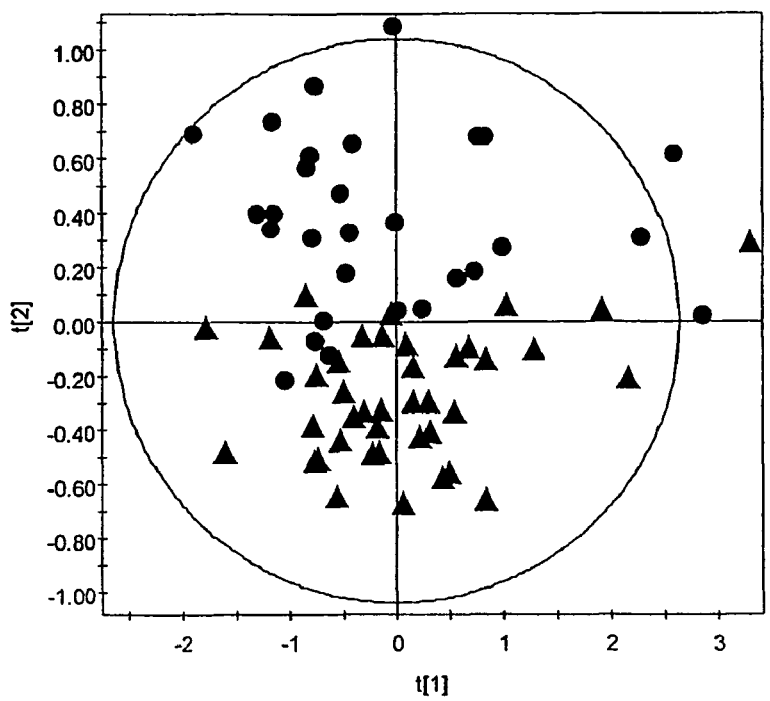
Figure 1B-OP
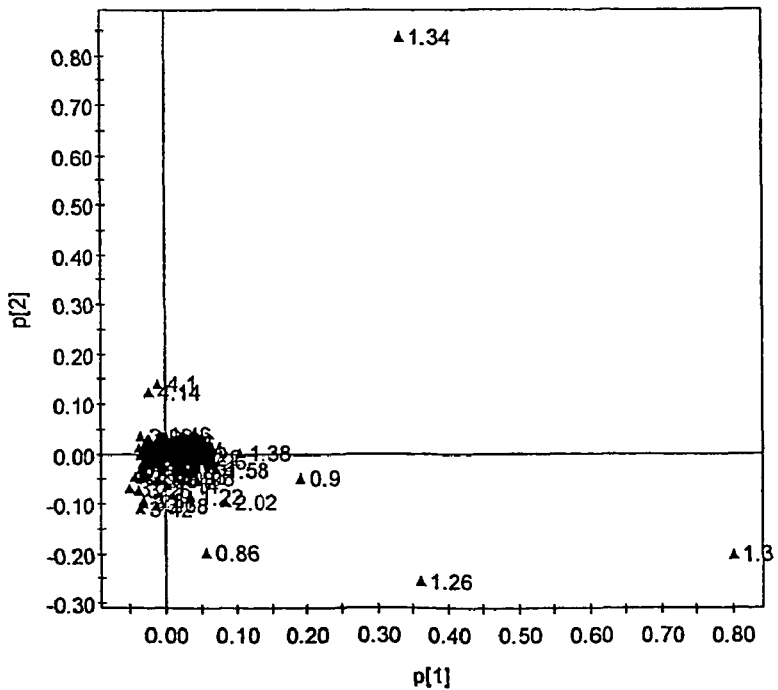

Figure 1C-OP
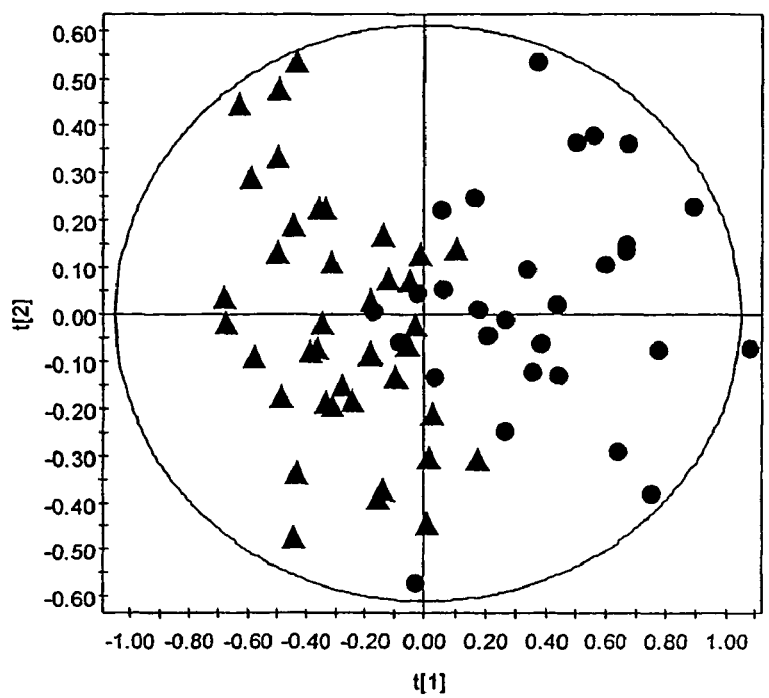
Figure 1D-OP
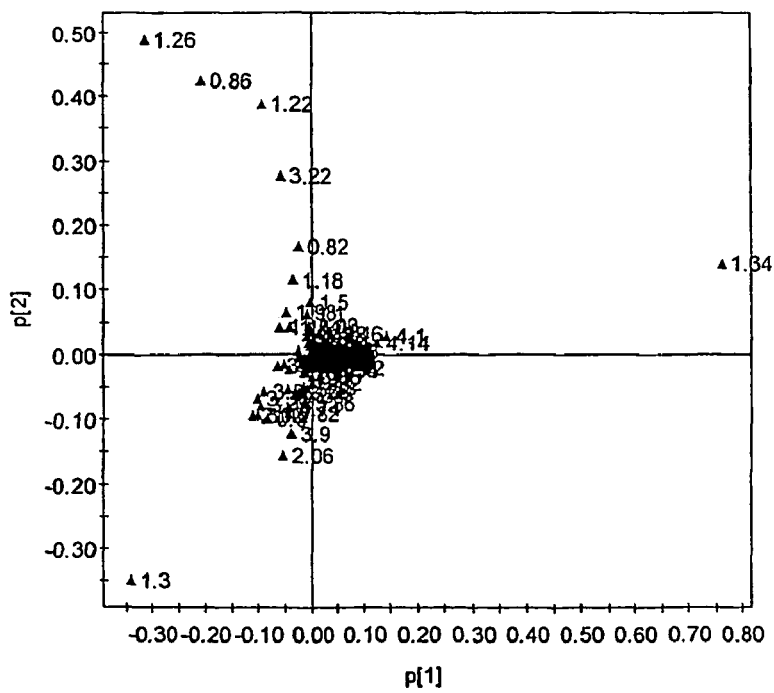

Figure 1E-OP
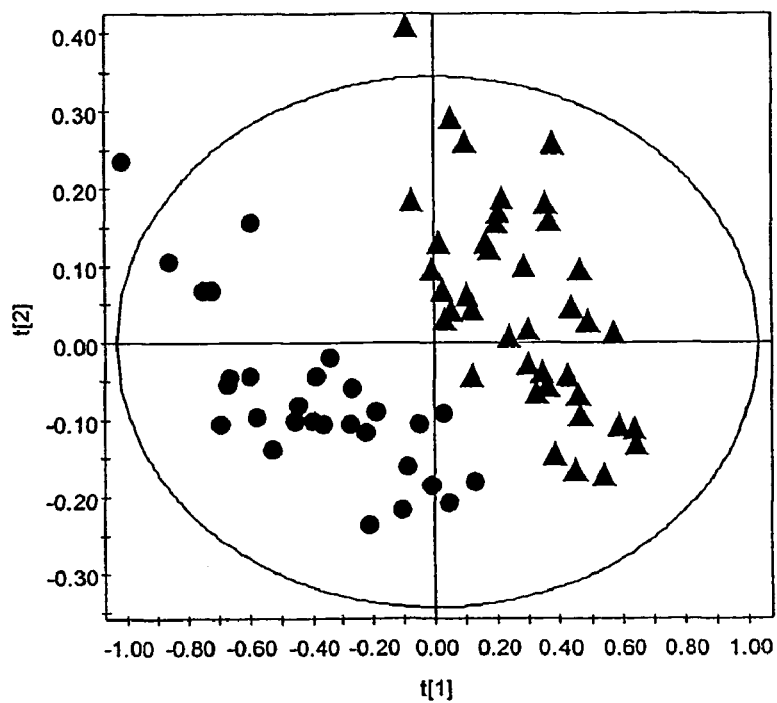
Figure 1F-OP
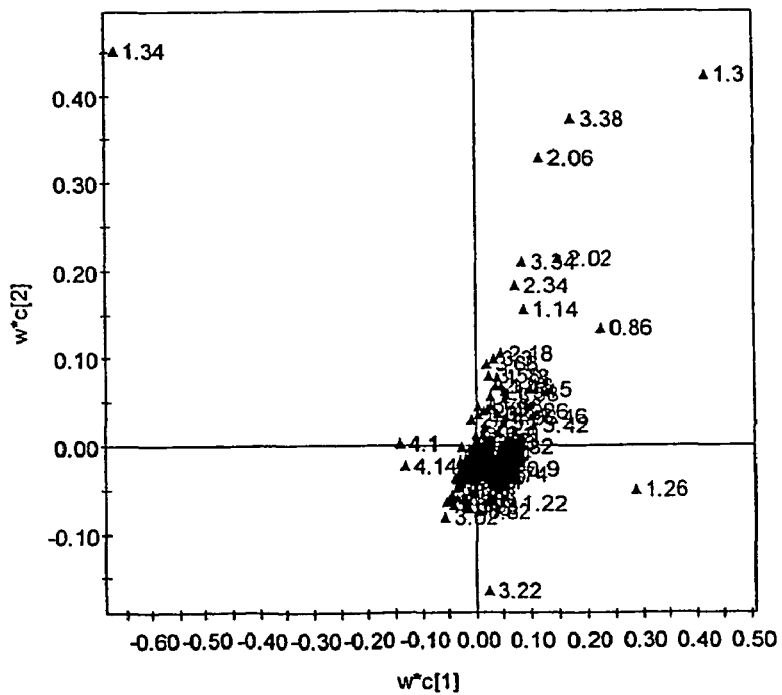

Figure 2A-OP
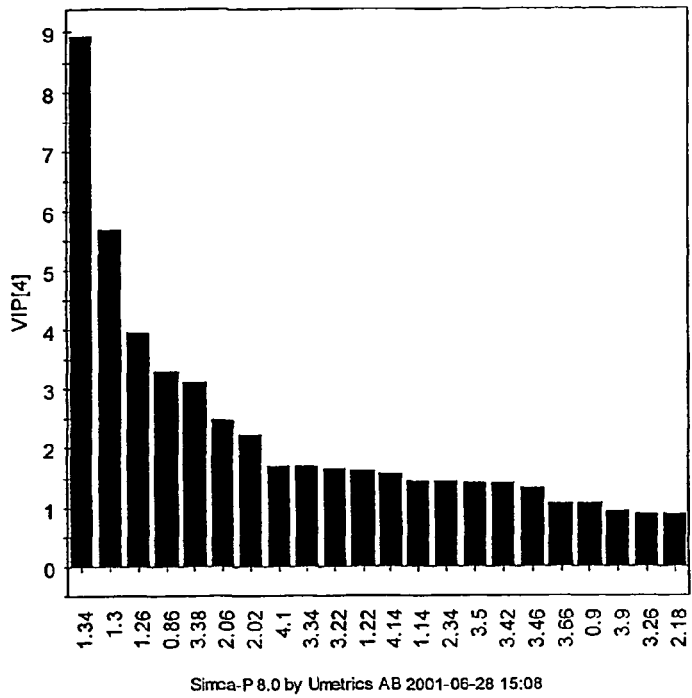
Figure 2B-OP
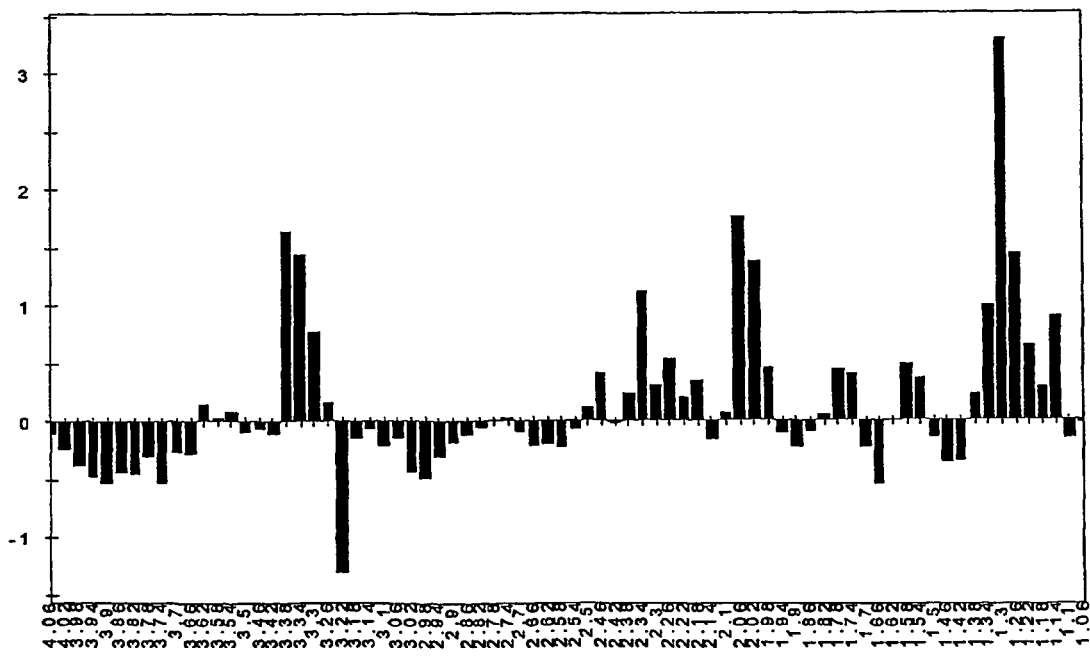

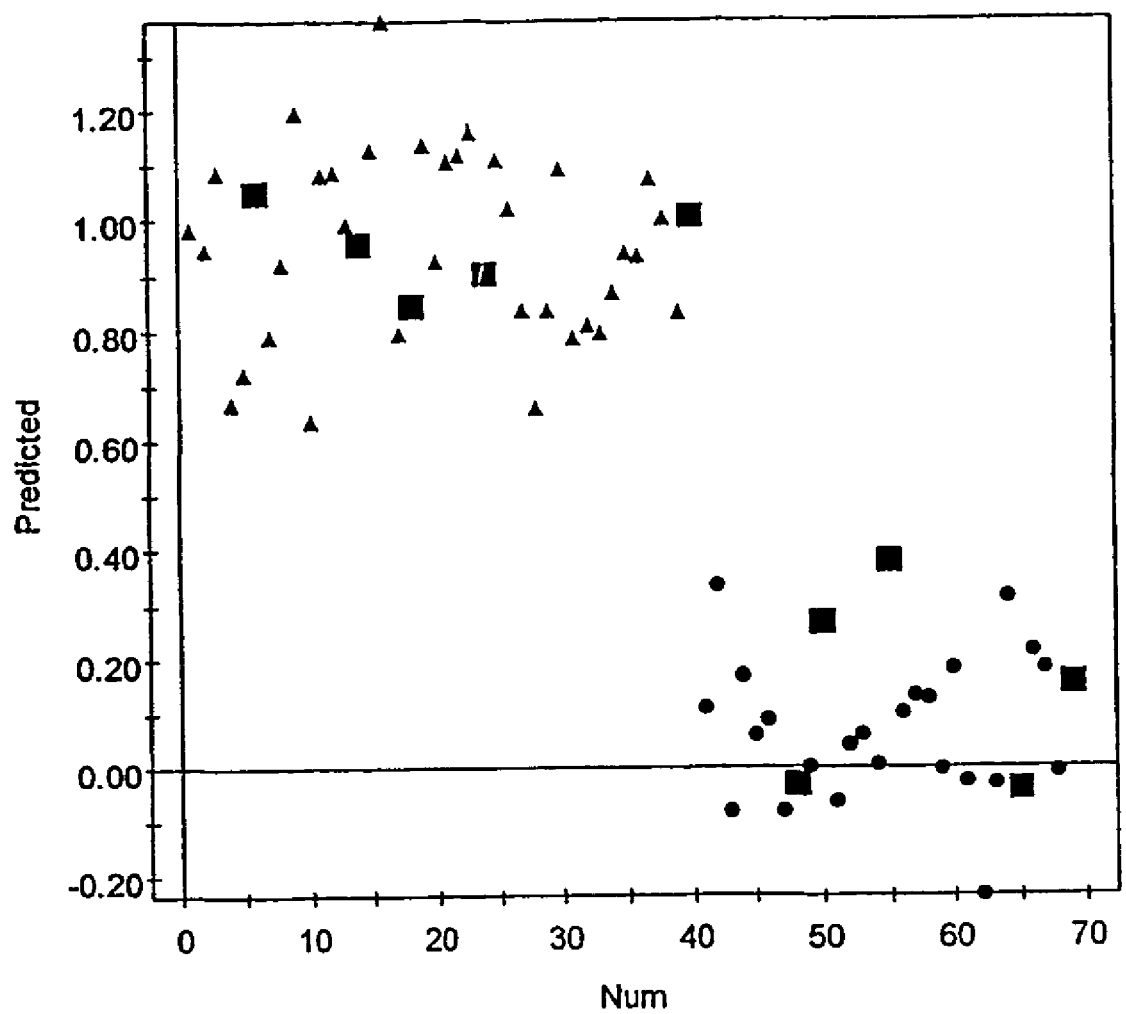

METHODS FOR THE DIAGNOSIS AND TREATMENT OF BONE DISORDERS

RELATED APPLICATIONS

This application is related to (and where permitted by law, claims priority to):
(a) United Kingdom patent application GB 0109930.8 filed 23 Apr. 2001;
(b) United Kingdom patent application GB 0117428.3 filed 17 Jul. 2001;
(c) U.S. Provisional patent application U.S. Ser. No. 60/307,015 filed 20 Jul. 2001;
the contents of each of which are incorporated herein by reference in their entirety.
This application is one of five applications filed on even date naming the same applicant:
(1) attorney reference number WJW/LP5995600 (PCT/GB02/01881; WO 02/086478);
(2) attorney reference number WJW/LP5995618 (PCT/GB02/01854; WO 02/086500);
(3) attorney reference number WJW/LP5995626 (PCT/GB02/01862; WO 02/086501);
(4) attorney reference number WJW/LP5995634 (PCT/GB02/01928; WO 02/085195)
(5) attorney reference number WJW/LP5995642 (PCT/GB02/01909; WO 02/086502);
the contents of each of which are incorporated herein by reference in their entirety.

TECHNICAL FIELD

This invention pertains generally to the field of metabonomics, and, more particularly, to chemometric methods for the analysis of chemical, biochemical, and biological data, for example, spectral data, for example, nuclear magnetic resonance (NMR) spectra, and their applications, including, e.g., classification, diagnosis, prognosis, etc., especially in the context of bone disorders, e.g., conditions associated with low bone mineral density, e.g., osteoporosis.

BACKGROUND

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Functions of Bone

The function of bone is to provide mechanical support for joints, tendons and ligaments, to protect vital organs from damage and to act as a reservoir for calcium and phosphate in the preservation of normal mineral homeostasis. Diseases of bone compromise these functions, leading to clinical problems such as fracture, bone pain, bone deformity and abnormalities of calcium and phosphate homeostasis.

Types of Bone

The normal skeleton contains two types of bone; cortical or compact bone, which makes up most of the shafts (diaphysis) of the long bones such as the femur and tibia, and trabecular or spongy bone which makes up most of the vertebral bodies and the ends of the long bones.

All bone is subject to continual turnover, with old bone being actively resorbed, and new bone being deposited. This turnover, or "remodelling" is essential for maintenance of structural competence because continual loading results in the formation of numerous microfractures in the bone matrix which, if left unchecked, would be weak points that could seed catastrophic failures of the bone, i.e., clinically obvious fractures. Such a process can be likened to a stone-chip on an automobile windscreen: the small crack can act as a catalyst for the sudden failure of the entire structure.

Remodelling is therefore an essential process for the maintaining bone strength. As the bone is resorbed and redeposited, the microfractures and structural imperfections are removed.

Trabecular bone has a greater surface area than cortical bone and because of this is remodeled more rapidly. Consequently, conditions associated with increased bone turnover tend to affect trabecular bone more quickly and more profoundly than cortical bone. Cortical bone is arranged in so-called Haversian systems which consists of a series of concentric lamellae of collagen fibres surrounding a central canal that contains blood vessels. Nutrients reach the central parts of the bone by an interconnecting system of canaliculi that run between osteocytes buried deep within bone matrix and lining cells on the bone surface. Trabecular bone has a similar structure, but here the lamellae run in parallel to the bone surface, rather than concentrically as in cortical bone.

Bone Composition

The organic component of bone matrix comprises mainly of type I collagen: a fibrillar protein formed from three protein chains, wound together in a triple helix. Collagen type I is laid down by bone forming cells (osteoblasts) in organised parallel sheets (lamellae). Type I collagen is a member of the collagen superfamily of related proteins which all share the unique structural motif of a left-handed triple helix. The presence of this structural motif, which is responsible for the mechanical strength of collagen sheets, imposes certain absolute requirements on the primary amino acid sequence of the protein. If these requirements are not met, the protein cannot form into the triple helix characteristic of collagens. The most important structural requirements are the presence of glycine amino acid residues at every third position (where the amino acid side chain points in towards the center of the triple helix) and proline residues at every third position to provide both structural rigidity and periodicity on the helix. Glycine is required because it has the smallest side chain of all the proteogenic amino acids (just a single hydrogen atom) and so can be accommodated in the spatially constrained interior of the helix. Proline is required because proline is the only secondary amine among the 20 proteogenic acids, which introduces a rigid 'bend' in the polypeptide, such that the presence of proline residues at repeated intervals will result in the adoption of a helical conformation.

After synthesis, the collagen protein is the subject of post-translational modifications which are essential for the structural rigidity required in bone. Firstly, collagen becomes hydroxylated on certain proline and lysine residues (e.g. to form hydoxyproline and hydroxylysine, respectively). This hydroxylation depends on the activity of enzymes that require vitamin C as a cofactor. Vitamin C deficiency leads to scurvy, a disease in which bone and other collagen-containing tissues (such as skin, tendon and connective tissue) are structurally weakened. This demonstrates the essential requirement for normal collagen hydroxylation.

After deposition into the bone, the collagen chains become cross-linked by specialised covalent bonds (pyridinium cross-links) which help to give bone its tensile strength. These cross links are formed by the action of enzymes on the hydroxylated amino acids (particularly hydroxylysine) in the collagen. It is the absence of these crosslinks which results in the weakened state of the tissue in scurvy when hydroxylation is inhibited by the absence of sufficient vitamin C.

The biochemical structure of collagen is an important factor in the strength of bone, but the pattern in which it is laid down is also important. The collagen fibres should be laid down in ordered sheets for maximal tensile strength. However, when bone is formed rapidly (for example in Paget's disease, or in bone metastases), the lamellae are laid down in a disorderly fashion giving rise to "woven bone," which is mechanically weak and easily fractured.

Bone matrix also contains small amounts of other collagens and several non-collagenous proteins and glycoproteins. The function of non-collagenous bone proteins is unclear, but it is thought that they are involved in mediating the attachment of bone cells to bone matrix, and in regulating bone cell activity during the process of bone remodelling. The organic component of bone forms a framework (called osteoid) upon which mineralisation occurs. After a lag phase of about 10 days, the matrix becomes mineralised, as hydroxyapatite $((Ca_{10}(PO_4)_6(OH)_2)$ crystals are deposited in the spaces between collagen fibrils. Mineralisation confers upon bone the property of mechanical rigidity, which complements the tensile strength, and elasticity derived from bone collagen.

Bone Cell Function and Bone Remodelling

The mechanical integrity of the skeleton is maintained by the process of bone remodelling, which occurs throughout life, in order that damaged bone can be replaced by new bone. Remodelling can be divided into four phases; resorption; reversal, formation, and quiescence (see, e.g., Raisz, 1988; Mundy, 1996). At any one time approximately 10% of bone surface in the adult skeleton is undergoing active remodelled whereas the remaining 90% is quiescent.

Osteoclast Formation and Differentiation

Remodelling commences with attraction of bone resorbing cells (osteoclasts) to the site, which is to be resorbed. These are multinucleated phagocytic cells, rich in the enzyme tartrate-resistant acid phosphatase, which are formed by fusion of precursors derived from the cells of monocyte/macrophage lineage. Osteoclast formation and activation is dependent on close contact between osteoclast precursors and bone marrow stromal cells. Stromal cells secrete the cytokine M-CSF, which is essential for differentiation of both osteoclasts and macrophages from a common precursor.

Mature osteoclasts form a tight seal over the bone surface and resorb bone by secreting hydrochloric acid and proteolytic enzymes through the "ruffled border" into a space beneath the osteoclast (Howship's lacuna). The hydrochloric acid secreted by osteoclasts dissolves hydroxyapatite and allows proteolytic enzymes (mainly Cathepsin K and matrix metalloproteinases) to degrade collagen and other matrix proteins. Deficiency of these proteins causes osteopetrosis which is a disease associated with increased bone mineral density and osteoclast dysfunction. After resorption is completed osteoclasts undergo programmed cell death (apoptosis), in the so-called reversal phase which heralds the start of bone formation.

Osteoblast Formation and Differentiation

Bone formation begins with attraction of osteoblast precursors, which are derived from mesenchymal stem cells in the bone marrow, to the bone surface. Although these cells have the potential to differentiate into many cell types including adipocytes, myocytes, and chondrocytes, in the bone matrix they are driven towards an osteoblastic fate. Mature osteoblasts are plump cuboidal cells, which are responsible for the production of bone matrix. They are rich in the enzyme alkaline phosphatase and the protein osteocalcin, which are used clinically as serum markers of osteoblast activity. Osteoblasts lay down bone matrix which is initially unmineralised (osteoid), but which subsequently becomes calcified after about 10 days to form mature bone. During bone formation, some osteoblasts become trapped within the matrix and differentiate into osteocytes, whereas others differentiate into flattened "lining cells" which cover the bone surface. Osteocytes connect with one another and with lining cells on the bone surface by an intricate network of cytoplasmic processes, running through cannaliculi in bone matrix. Osteocytes appear to act as sensors of mechanical strain in the skeleton, and release signalling molecules such as prostaglandins and nitric oxide (NO), which modulate the function of neighbouring bone cells.

Regulation of Bone Remodelling

Bone remodelling is a highly organised process, but the mechanisms which determine where and when remodelling occurs are poorly understood. Mechanical stimuli and areas of micro-damage are likely to be important in determining the sites at which remodelling occurs in the normal skeleton. Increased bone remodelling may result from local or systemic release of inflammatory cytokines like interleukin-1 and tumour necrosis factor in inflammatory diseases. Calciotropic hormones such as parathyroid hormone (PTH) and 1,25-dihydroxyvitamin D, act together to increase bone remodelling on a systemic basis allowing skeletal calcium to be mobilised for maintenance of plasma calcium homeostasis. Bone remodelling is also increased by other hormones such as thyroid hormone and growth hormone, but suppressed by oestrogen, androgens and calcitonin. There has been considerable study of the processes which regulate the bone resorption side of the balance, but the factors regulating the rate of bone deposition are considerably less well understood.

Bone Disorders

There are a range of disorders of bone which result from the failure to properly regulate the metabolic processes which govern bone turnover (e.g., metabolic bone disorders).

Osteoporosis (OP) is the most prevalent metabolic bone disease. It is characterized by reduced bone mineral density (BMD), deterioration of bone tissue, and increased risk of fracture, e.g., of the hip, spine, and wrist. Many factors contribute to the pathogenesis of osteoporosis including poor diet, lack of exercise, smoking, and excessive alcohol intake. Osteoporosis may also arise in association with inflammatory diseases such as rheumatoid arthritis, endocrine diseases such as thyrotoxicosis, and with certain drug treatments such as glucocorticoids. However there is also a strong genetic component in the pathogenesis of osteoporosis.

Osteoporosis is a major health problem in developed countries. As many as 60% of women suffer from osteoporosis, as defined by the World Health Organisation (WHO), with half of these suffers also having clinically relevant skeletal fractures. Thus 1 in 3 of all women in developed countries will have a skeletal fracture due to osteoporosis. This is a major cause of morbidity and mortality leading to massive health care costs (an estimated $14 billion per annum in the USA alone) (see, e.g., Melton et al., 1992).

Osteopetrosis, the opposite of osteoporosis, is characterised by excessive bone mineral density. It is, however, much rarer than osteoporosis with as few as 1 in 25,000 women affected.

After osteoporosis, the next most prevalent bone disease is osteoarthritis. Osteoarthritis (OA) is the most common form of arthritis in adults, with symptomatic disease affecting roughly 10% of the US population over the age of 30 (see, e.g., Felson et al., 1998). Because OA affects the weight bearing joints of the knee and hip more frequently than other joints, osteoarthritis accounts for more physical disability among the elderly than any other disease (see, e.g., Guccione et al., 1994). Osteoarthritis is the most common cause of total knee and hip replacement surgery, and hence offers significant economic as well as quality of life burden. Recent estimates suggest the total cost of osteoarthritis to the economy, accounting for lost working days, early retirement and medical treatment may exceed 2% of the gross domestic product (see, e.g., Yelin, 1998).

The physiological mechanisms which underlie osteoarthritis remain hotly debated (see, e.g., Felson et al., 2000) but it seems certain that several environmental factors contribute, including excess mechanical loading of the joints, acute joint injury, and diet, as well as a strong genetic component. The disease is characterised by the narrowing of the synovial space in the joint, inflammatory and fibrous changes to the connective tissue, and altered turnover of connective tissue proteins, including the primary connective tissue collagen, type II. The most recent studies suggest that osteoarthritis may result from misregulated connective tissue remodelling in much the same way that osteoporosis results from misregulated bone remodelling. Whereas osteoporosis is a disease of quantitatively low bone mineral density, osteoarthritis is a disease of spatially inappropriate bone mineralisation.

There are a range of other less common bone disorders, including:

Ricketts and osteomalacia are the result of vitamin D deficiency. Vitamin D is required for absorption of calcium and phosphate and for their proper incorporation into bone mineral. Deficiency of vitamin D (called Ricketts in children and osteomalacia in adults) results in a range of symptoms including low bone mineral density, bone deformation and in severe cases muscle tetany due to depletion of extracellular calcium ion stores.

Hyperparathyroidism (over production of parathyroid horomone or PTH) can have similar symptoms to Ricketts. This is unsurprising since PTH production is stimulated in Ricketts as an attempt to maintain the free calcium ion concentration. PTH stimulates bone resorption by promoting osteoclast activity, and hence can result in symptoms resembling osteoporosis. Osteomalacia and hyperparathyoidism combined contribute only a very small fraction of all cases of adult osteoporosis. In almost every case, adult osteoporosis is due to defective bone deposition rather than overactive resorption (see, e.g. Guyton, 1991).

Paget's disease of bone is a relatively common condition (affecting as many as 1 in 1000 people in some areas of the world) of unknown cause, characterized by increased bone turnover and disorganized bone remodeling, with areas of increased osteoclastic and osteoblast activity. Although Pagetic bone is often denser than normal bone, the abnormal architecture causes the bone to be mechanically weak, resulting in bone deformity and increased susceptibility to pathological fracture.

Multiple myeloma is a cancer of plasma cells. In contrast to most other haematological malignancies, the tumour cells do not circulate in the blood, but accumulate in the bone marrow where they give rise to high levels of cytokines that activate osteoclastic bone resorption (e.g., interleukin-6). The disease accounts for approximately 20% of all haematological cancers and is mainly a disease of elderly people.

Balance Between Bone Deposition and Bone Resorption

All of the bone pathologies listed above result from an imbalance between bone deposition and bone resorption. If the mechanisms regulating these two processes become uncoupled than pathological changes in bone mineral density result. In just a few cases, the cause of the imbalance seems clear: for example prolonged estrogen deficiency (such as due to surgical sterilisation) or lengthy treatment with glucocorticoids (such as for asthma) both perturb the balance and can lead to rapid demineralisation of the bone and osteoporosis.

Unfortunately, in the vast majority of cases the mechanisms resulting in loss of balance are much less clear. The difficulty in identifying the causes stems in part of the small scale imbalances that must be occurring. For example, most osteoporotic fractures do not occur until 20-30 years after the menopause. If, as is generally assumed, the osteoporosis was initiated by the reduction in estrogen levels after the menopause, then the demineralisation has been occurring steadily over two or three decades. Since the bone remodelling process is relatively rapid (complete within 28 days in any given osteon) we must assume that the imbalance in favour of demineralisation is very small.

Current Treatments

There are currently two major classes of drugs used in the prevention and treatment of osteoporosis: (1) Hormonally active medications (estrogens, selective estrogen receptor modulators (SERMs)); and (2) anti-resorptives.

There is presently good data to suggest that the long term use of hormonally active medications (usually estrogen, estrogen analogs or conjugated estrogens) after the menopause in women can prevent bone demineralisation and hence delay the onset of osteoporosis. The molecular mechanisms involved are not clearly defined, possibly because they are so complex. However, there are plausible mechanisms which involve both stimulation of bone deposition and suppression of resorption.

To date, such hormonally active medications, including the new generation of SERMs, such as Raloxifene™, which have the beneficial effects of estrogen on bone and the cardiovascular system but do not have the side effects of breast and uterine hyperplasia that can increase the risk of cancer, have not achieved widespread use for the treatment of existing osteoporosis.

At present, treatment of known or suspected bone mineral deficiency is most commonly by the use of drugs to suppress osteoclast activity. The two most important drug groups in this class are bisphophonates (BPs) and non-steroidal anti-inflammatory drugs (NSAIDs).

Bisphosphonates (also know as diphosphonates) are an important class of drugs used in the treatment of bone diseases involving excessive bone destruction or resorption, e.g., Paget's disease, tumour-associated osteolysis, and also in post-menopausal osteoporosis where the defect might be in either bone deposition or resorption. Bisphosphonates are structural analogues of naturally occurring pyrophosphate. Whereas pyrophosphate consists of two phosphate groups linked by an oxygen atom (P—O—P), bisphosphonates have two phosphate groups linked by a carbon atom (P—C—P). This makes bisphosphonates very stable and resistant to degradation. Furthermore, like pyrophosphate, bisphosphonates have very high affinity for calcium and therefore target to bone mineral in vivo. The carbon atom that links the two phosphate groups has two side chains attached to it, which can be altered in structure. This gives rise to a multitude of bisphosphonate compounds with different anti-resorptive potencies. Bone resorption is mediated by highly specialised, multinucleated osteoclast cells. Bisphosphonate drugs specifically inhibit the activity and survival of these cells. Firstly, after intravenous or oral administration, the bisphosphonates are rapidly cleared from the circulation and bind to bone mineral. As the mineral is then resorbed and dissolved by osteoclasts, it is thought that the drug is released from the bone mineral and is internalised by osteoclasts. Intracellular accumulation of the drugs inhibits the ability of the cells to resorb bone (probably by interfering with signal transduction pathways or cellular metabolism) and causes osteoclast apoptosis (see, e.g., Hughes et al., 1997).

NSAIDs are widely used in the treatment of inflammatory diseases, but often cause severe gastrointestinal (GI) side effects, due their inhibition of the prostaglandin-generating enzyme, cyclooxygenase (COX). Recently developed selective cyclooxygenase-2 (COX-2) inhibitors offer new treatment strategies which are likely to be less toxic to the GI tract. NSAIDs developed by Nicox SA (Sophia Antipolis, France), that contain a nitric oxide (NO)-donor group (NO-NSAID) exhibit anti-inflammatory properties without causing GI side effects. The mechanisms responsible for the beneficial effects of NSAIDs on bone are not definitively identified, but since the bone resorbing osteoclast cells are derived from the circulating monocyte pool, it is not difficult to imagine why generalised anti-inflammatory treatments might have anti-resoptive effects. However, another class of powerful anti-inflammatory molecules, the glucacorticoids and their analogs such as dexamethasone have the opposite effects to NSAIDs: chronic dexamethasone treatment (for example, in asthma) induces demineralisation and leads to symptoms of rapid onset osteoporosis. Consequently, while NSAIDs empirically have anti-resorptive properties, further investigations into the detail mechanism of action of these drugs are clearly required.

It has recently been discovered that many of the drugs, which are used clinically to inhibit bone resorption, such as bisphosphonates and oestrogen do so by promoting osteoclast apoptosis (see, e.g., Hughes et al., 1997). At present the most commonly used types of drugs used to suppress osteoclast activity in these diseases are bisphophonates (BPs) and non-steroidal anti-inflammatory drugs (NSAIDs).

Limitations of Current Treatments

There are a number of limitations which impact on the clinical utility of all the available therapeutic and preventative modalities. For example, both hormonal medications (HRT and SERMs) and antiresorptives (BPs and NSAIDs) primarily target resorption. While this may be useful in, for example Paget's disease, it is likely to be less useful in osteoporosis, where the majority of cases have reduced deposition rates as the primary defect. Of course, because bone mineral density is a balance between deposition and resorption rates, antiresorptive strategies can have some efficacy even where the primary defect is in the rate of deposition.

Possibly because current therapeutics target resorption when suppressed deposition is the primary defect in osteoporosis, none of the current agents can build bone, but instead only halt further demineralisation. Because of the limited availability of diagnostic techniques, particularly for population screening, treatment cannot usually begin until clinical symptoms exist (such as fracture) by which point the bones may already be dangerously demineralised. In such cases (which are the majority), a therapy which increases bone mineral density would be desirable. A new treatment based on abolishing proline deficiency would stimulate deposition rate and hence be a new category of therapeutic: one which targets deposition preferentially over resorption. Therapeutics of this categoy would be expected to overcome the limitation of being unable to increase bone mineral density.

Another limitation of exisiting therapies is the failure to treat the underlying cause of the pathology, but rather to try and alleviate the symptoms. In part, this is because few direct causes of osteoporosis have been identified. The inventors have identified a novel contributory mechanism to the development of osteoporosis and hence have provided the first therapeutic approach to target one of the direct mechanisms resulting in pathologically low bone mineral density.

Bone Disorder Diagnostics

It has long been clear that early diagnosis of bone disorders was essential for good therapeutic management. Although there are now several effective treatments for osteoporosis, each one is only able to arrest the further loss of bone mineral density. No treatment to date has been effective in reversing loss which has already occurred. Thus early, reliable diagnosis of declining bone mineral density is of the utmost clinical importance.

Existing diagnosis methods for bone disorders fall into two categories:

(a) direct observation (for example, bone mineral density scans for osteoporosis or radiographic assessment for osteoarthritis); and, (b) indirect observation of molecular markers of remodelling (for example, collagen breakdown products).

Of the major determinants for bone fracture, only bone mineral density can presently be determined with any precision and accuracy.

Bone densitometers typically give results in absolute terms (i.e., bone mineral density, BMD, typically in units of $g/cm^2$) or in relative terms (T-scores or Z-scores) which are derived from the BMD value. The Z-score compares a patient's BMD result with BMD measurements taken from a suitable control population, which is usually a group of healthy people matched for sex and age, and probably also weight. The T-score compares the patient's BMD result BMD measurements taken from a control population of healthy young adults, matched for sex. In other words, for Z-scores, age- and sex-matched controls are used; for T-scores just sex-matched controls are used. The World Health Organisation (WHO) defines osteoporosis as a bone mineral density (BMD) below a cut-off value which is 1.5 standard deviations (SDs) below the mean value for the age- and sex-matched controls (Z-scores), or a bone mineral density (BMD) below a cut-off value which is 2.5 standard deviations (SDs) below the mean value for the sex-matched controls (T-scores) (see, e.g., World Health Organisation, 1994).

The two most widely used methods for assessing bone mineral density (BMD) is the DEXA scan (dual emission X-ray absorbtion scanning) and ultrasound. The DEXA method is considered the gold standard diagnostic tool for bone mineral density, providing a reliable estimate of average bone mineral density in units of grams per cubic centimetre. It can be applied to a number of different bones, but is most commonly used to measure lumbar spine density (as a measure of cortical bone) and femoral neck density (as a measure of trebecular bone mineral density). Ultrasound is easier and cheaper to perform than DEXA scanning, but provides a less reliable estimate of bone mineral density and its accuracy is compromised by the surrounding soft tissue. As a result, ultrasound is usually performed on the heel, where interference by soft tissue is minimised, but it is unclear whether this is typical of whole body bone mineral density, and in any case it does not allow an assessment of cortical bone. See, for example, Pocock et al., 2000; Prince, 2001.

Almost all of the molecular diagnostics currently employed are based on measurements of bone breakdown products. The steady state level of breakdown products should be related to the bone remodelling rate, although it will be biased towards detection of overactive resorption rather than underactive deposition. It may be, in part, for this reason that all therapies currently on trial for osteoporosis (such as estrogen receptor modulators or bisphosphonates) are based on an antiresorptive strategy rather than on promoting deposition, even though (as noted above) most cases of osteoporosis are not due to overactive resorption.

Examples of molecular diagnostics include the measurement of free crosslinks, hydroxyproline, collagen propeptides, or alkaline phosphatase in serum or urine. Free crosslinks are produced when collagen is degraded during resorption. Although the collagen can mostly be broken down to free amino acids, the trimerised hydroxylysine residues that formed the crosslinks cannot be further metabolised and so accumulate in the blood until secreted by the kidney in urine. Thus the levels of crosslink in serum or in urine will be related to the rate of collagen breakdown (most, but not all, of which will be occurring in the bone). Tests for hydroxyproline rely on a similar principle: free proline (that is, proline not incorporated into protein) is never in the hydroxylated form, hydroxyproline. As a result, the only source of free hydroxyproline in blood is from collagen breakdown. As for crosslinks, the free hydroxyproline generated during breakdown cannot be metabolised any further and accumulates until excreted by the kidney. Unfortunately, the level of both of these metabolites (in either serum or urine) is significantly affected by kidney function.

Collagen is produced as a proprotein which has both an N-terminal and C-terminal extension cleaved off prior to incorporation into the extracellular matrix. These extensions, or propeptides, are then metabolised or excreted. However, the steady state level of the propeptides has been suggested to be a marker for collagen deposition, some, but not all, of which is likely to be occurring in the bone.

Problems with Current Diagnostic Methods

The gold standard bone densitometry method, DEXA scanning, is too cumbersome and expensive for routine screening procedures in women without clinical signs of osteoporosis. It requires specialist apparatus (which is large and expensive to install and maintain) as well as specialist training for its operation. Despite accurately measuring bone mineral density, and hence providing the benchmark diagnosis of osteoporosis, nevertheless it does not accurately predict future fracture risk, suggesting that bone quality as well as density may also be important (see, for example, the comments above).

Ultrasound measurements on the heel are simpler to perform, using cheaper apparatus and requiring less operator training, but the results are generally less able to predict the presence of either osteoporosis or future fracture risk.

Molecular diagnostics are considerably easier to implement, although in many cases the reagents required for the assays are expensive to obtain. The major disadvantage of the markers which have been evaluated to date is that the levels of the breakdown products in serum or urine are not particularly temporally stable, changing with diurnal rhythm and also from day to day. As a result, spot measures (i.e., a single specimen taken at a randomly chosen time) have virtually no diagnostic or prognostic power. Series of measurements can be used to provide some indication of relative risk for osteoporosis, but the odds ratio for having osteoporosis is only approximately 2-fold among individuals with high levels of the turnover markers (see, e.g., Garnero, 1996). Such a weak association is of little or no practical clinical value, and as a result, biochemical markers of bone metabolism have not found widespread application in the conical arena, and have not been considered for population screening.

Another important limitation of current molecular diagnostics is the focus on the products of bone metabolism (such as cross links, hydroxyproline, and collagen propetides). These species might offer diagnostic potential but they provide no information at all about the underlying causes of the imbalance between deposition and resorption. Identification of a risk factor that was not a direct marker of bone turnover may offer the prospect of identifying therapeutic targets as well as having prognostic potential.

Metabonomic methods involve obtaining a high density data set which contains information on the identities and relative amounts of all of the low molecular weight substances in a biologial sample (in the present case, human blood serum, although other biofluids can be used as well as tissue samples). These data sets are subjected to pattern recognition or multivariate statistical analyses to identify metabolites, the presence or relative amounts of which are specifically associated with the sample class (e.g., control vs. patient with a particular disease).

As discussed in detail below, the inventors have applied the technique of metabonomics to osteoporosis and have identified a novel biomarker for bone disorders, for example, conditions associated with low bone mineral density, such as osteoporosis: free proline.

Proline

Proline is an alpha-amino acid and one of the twenty proteogenic amino acids (i.e., one of the twenty amino acids which can be incorporated during de novo protein synthesis). Although proteins can contain amino acids other than the basic set of twenty, this only occurs through post-translation modification (e.g., hydroxylation of proline or lysine, gamma-carboxylation of glutamate, etc.). Since the 1950s, all 20 of the proteogenic amino acids have been known to be present in the free form (i.e., not incorporated into a peptide or protein) in human blood (see, e.g., Stein et al., 1954a, 1954b) at levels between 20 µM and 500 µM. Generally, the levels of the amino acids in blood are tightly regulated and do not vary to a great extent between individuals and as a result they are not routinely measured in clinical studies.

Proline, shown below, is one of several amino acids with an alkyl side chain, but is unique among the proteogenic amino acids in that it is a secondary amine, and a cyclic amine, and is, more precisely, an imino acid. This has important structural consequences when proline is incorporated into a polypeptide, causing the chain to "bend". Where a particular protein structure, such as a left-handed helix, is required, proline is the only amino acid capable of providing rigidity to such a structural motif. Although proline exists in the D- or L-configuration, the D-configuration is most common in a biological setting. Free proline may be in a non-ionic form or in an ionic form (e.g., as a zwitterion), as is usually the case in solution at physiological pH.

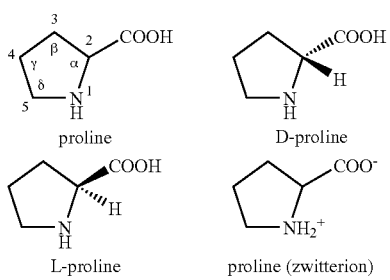

proline   D-proline   L-proline   proline (zwitterion)

Although present in almost every protein, proline is a particularly important constituent of the extracellular matrix proteins of the collagen family. Proline is important both in terms of function (its secondary amine structure promotes helical rigidity) and also in terms of amount. All collagens are constructed from the repeated tripeptide motif -Gly-X-Pro- where Gly is glycine, X is any amino acid, and Pro is proline. Thus, almost one-third by mass of all fibrillar collagens (such as type I collagen in bone or type II collagen in connective tissue) is made up of proline. No other known protein has a mass fraction of proline even approaching this value.

Unlike many other amino acids (such as glycine, glutamate, and tryptophan), free proline has not been implicated in any metabolic pathways other than peptide and protein synthesis. Glycine and glutamate are directly active as signalling molecules, while tryptophan is widely metabolised into signalling molecules such as serotonin. These amino acids (glycine, glutamate) and amino acid derivatives (serotonin, dopamine, adrenalin, etc.) play essential roles in the nervous system as neurotransmitters and may play other key signalling roles, for example, in the control of the immune system. In contrast, no similar roles have been identified for free proline and no biologically active proline-derived metabolites have been reported. As a result, the biochemistry of free proline is much less well understood than for most of the other proteogenic amino acids.

As a result, there are relatively few metabolic reactions which involve free proline: (a) Synthesis of loaded tRNA-Pro, the first step in the incorporation of proline into peptides and proteins. (b) Reactions involved in the synthesis of proline through interconversion of amino acids. In mammals, there are two such pathways: (i) Synthesis from glutamate which involves the sequential action of the enzymes gamma-glutamyl kinase, gamma-glutamyl phospthate reductase (which are separate activities of the same enzyme) and □-pyrroline-5-carboxylate reductase (P5C-reductase). (ii) Synthesis from arginine, via ornithine, which involves the sequential activity of ornithine transaminase and P5C-reductase. In unicellular organisms, there additional proline-utilising pathways (e.g., proline racemase, D-proline reductase and ornithine cyclase have all be identified in *Clostridium* species. (c) Reactions involved in the catabolism of proline, for interconversion into other amino acids. In mammals, the enzyme proline oxidase, which converts proline into P5C is the major catabolic enzyme for proline. The resulting P5C can be further metabolised to glutamate or arginine (via ornithine) or it can be converted back to proline by P5C reductase.

The only other enzymes which act on proline do so only when the proline has been incorporated as a peptidyl-prolyl residue in a polypeptide chain. Such enzymes include proline hydroxylase, the vitamin C dependent enzyme necessary for generating crosslinks in collagen; and peptidylproplyl cis-trans isomerase, an enigmatic family of enzymes whose physiological role is poorly defined, but which has been widely studied after it was discovered to be the target of major immunosuppressive drugs such as cyclosporin.

The total body supply of proline (most of which is incorporated into collagen in bone and muscle at any given time) is derived from two sources:
(a) dietary supply (for example, from the hydrolysis of dietary protein); and,
(b) endogenous synthesis (proline is a non-essential amino acid because humans retain the biochemical pathways necessary to synthesise it).

In order to be taken up from the dietary protein supply, the protein must be efficiently hydrolysed in the stomach, and specific uptake mechanisms then transport the peptides containing proline across the gut epithelium. These small peptides are then subjected to enzymatic hydrolysis to release their free amino acids into the blood.

Proline derived from the diet is supplemented by synthesis, primarily by the liver. The synthesis pathway begins with the citric acid cycle intermediate α-ketoglutarate which is converted into another non-esstential amino acid, glutamate. This glutamate, or glutamate obtained directly from the diet, is then converted via a three step pathway into proline. First, the glutamate is reacted with ATP to form glutamic-γ-semi-aldehyde. This product has two fates: it can either be converted into ornithine and hence to arginine, or else it loses water and is cyclised to form Δ-pyrroline-5-carboxylate. This intermediate is then reduced by the enzyme Δ-pyrolline 5-carboxylate dehydrogenase (P5CDH) to give proline. Alternatively, proline may be synthesised from dietary arginine via ornithine and the enzyme ornithine transaminase, which converts ornithine into Δ-pyrroline-5-carboxylate and thence to proline via the action of P5C reductase. The relative contribution of the two synthetic pathways in not well understood, but the glutamate pathway is likely to be the major contributor under most circumstances.

Free proline in the blood is lost through three routes: (a) incorporation into proteins, mainly collagen; (b) a small amount of renal excretion; and, (c) metabolism to other amino acids, such as arginine and glutamate. The vast majority of the free proline is used to support the high level of collagen turnover in the healthy individual. Renal excretion is very low because proline, unique among the proteogenic amino acids, has a specific re-uptake mechanism in the kidney nephron. The evolution of such a mechanism underlies the value placed on retaining the whole body supply of proline. Specific genetic disorders of this process can lead to hyperprolinuria, and this may in these rare cases result in serum proline deficiency.

To be utilised in protein synthesis, and specifically in collagen biosynthesis, there must not only be a sufficient total body supply of proline, but it must also be available to the cells performing the protein synthesis. Like other small charged molecules, proline is unable to cross the plasma membrane by diffusion, but must be transported. Proline taken up into cells by the System A amino acid transporter responsible for all uptake of all proteogenic amino acids with neutral side chains. The system A transporter has been cloned (it is the product of the SAT2 gene) and is inhibited by the "ideal" subtrate methylaminoisobutyrate (MeAlB). Thus, proline transport (for example across the gut epithelium, or into osteoblasts) may also be an important regulatory step both in the determination of serum proline levels and in the determination of collagen biosynthesis rates. Interestingly, tissues engaged in the highest levels of collagen biosynthesis (e.g., bone) have the highest levels of SAT2 expression, and agents which promote collagen formation (e.g., the cytokine TGF-beta) stimulate SAT2 expression and proline uptake capacity in parallel (see, e.g., Ensenat et al., 2001).

Hydroxyproline, in contrast to free proline, is not used for protein synthesis. It cannot be incorporated directly into protein and must instead be generated by the action of prolyl hydroxylase on polypeptides containing proline. It has no other biological activity ascribed to it, and is essentially a waste product from collagen breakdown. It is plausible that hydroxyproline could interfere with other steps in the proline metabolic pathways (e.g., with the synthesis of proline, by product inhibition of the P5C reductase enzyme, or with the kidney re-uptake mechanism, or the System A amino acid transporter); however, there is presently little evidence to support this hypothesis. Any evidence for such action of hydroxyproline would convert it from the role of innocent bystander in osteoporosis to a potential causal contributor.

Free proline is an important component of the bone turnover cycle because bone remodelling demands by far the highest amounts of free proline of any process in the adult, specifically, for de novo collagen synthesis. It has long been suggested that proline is necessary for collagen synthesis. However, to date, there has been no evidence that proline is rate limiting for bone synthesis.

The inventors have now demonstrated that proline is not only necessary, but is rate limiting for new bone formation. Consequently, sub-optimal levels of available free proline cause osteoporosis by slightly slowing the rate of collagen biosynthesis, and hence tipping the balance slightly in favour of demineralisation over a long time period. Furthermore, the inventors have demonstrated, for the first time, that a low concentration of free proline is a risk factor for osteoporosis.

Low Proline Levels

There are many reasons for low proline levels, and these include:

(1) insufficient dietary intake of proline;
(2) failure to absorb dietary proline, e.g., due to a malabsorption defect.
(3) failure to synthesize proline, e.g., due to an enzymatic/genetic defect.
(4) kidney disorder, e.g., malfunction of selective re-uptake of proline.

The proline content of various diets is likely to differ more markedly than for any other free amino acid. Although the total amount of protein intake varies somewhat between individuals, the most dramatic dietary variations are in the nature of the proteins eaten between vegans, vegetarians, and meat-eaters. Collagens, which have by far the highest proline content per gram of protein, are uniquely found in animals as opposed to plants. As a result, the proline content of a vegetarian diet may be less than 50%, and possibly as low as 20%, of the levels in an average meat-eater diet. Thus, both the overall protein content of the diet and the nature of the protein consumed will have a substantial effect on the total amount of proline available for dietary absorption. Individuals who have low proline levels due to dietary insufficiency would be amenable to therapy with proline supplements, e.g., oral supplements.

Even if the diet is replete with proline, the contribution of dietary sources to the plasma pool of free proline will be inadequate if the available proline is not properly absorbed and processed. Many of these steps are in common with other amino acids (e.g., hydrolysis by stomach acids and enzymes, bulk phase pinocytosis of peptides by gut epithelium, etc.). However, the body may be less sensitive to malabsorption of other amino acids for which the whole body demand is less. Individuals with low proline levels due to malabsorption syndromes will not generally be amenable to therapy with oral proline, but may require parenteral administration of proline or treatment of the underlying cause of the proline malabsorption.

Although dietary sources of proline are likely to be important, based on the rapid increase in serum free proline following an oral proline-rich meal (see, e.g., Stein et al., 1954a, 1954b), endogenous synthesis is also presumably important. By analogy with other systems, such as the cholesterol metabolic pathway, endogenous synthesis is usually regulated to provide additional product only when nutritional sources are inadequate. Thus, dietary insufficiency or malabsorption might reveal an underlying defect in the biosynthesis pathway that normalises free proline levels in healthy individuals. Such a defect might be genetic or epigenetic in origin: for example, polymorphisms may exist in the enzymes involved in proline biosynthesis (e.g., P5C reductase) which operate at slightly different rates, or which are subject to subtly different control mechanisms.

As has already been noted, proline is specifically reabsorbed by the kidney. As a result, any disease with alters kidney function could result in lower free proline levels through loss via the kidneys. Such kidney loss may be very significant, and both dietary and endogenous synthesis pathways may be incapable of normalising free proline levels if proline were lost via the kidneys at a rate comparable to some amino acids (e.g., serine). Such genetic defects resulting in hyperprolinuria have already been described in the literature, although no data on their bone mineral density is yet available.

Also, accumulated hydroxyproline from bone breakdown might interefere with proline absorption, synthesis, cellular transport, or renal re-uptake, resulting in a secondary proline deficiency. Elevated levels of hydroxyproline might arise from increased bone turnover (e.g., in Ricketts or hyperthyroidism) or as a result of failure to clear hydroxyproline through the normal renal excretion mechanism.

SUMMARY OF THE INVENTION

One aspect of the present invention pertains to one or more diagnostic species, including free proline or a surrogate for free proline, for use in a method of classification.

One aspect of the present invention pertains to a method of classification according to bone state which employs or relies upon one or more diagnostic species, including free proline or a surrogate for free proline.

One aspect of the present invention pertains to use of one or more diagnostic species, including free proline or a surrogate for free proline, in a method of classification according to bone state.

One aspect of the present invention pertains to an assay for use in a method of classification according to bone state, which assay relies upon one or more diagnostic species, including free proline or a surrogate for free proline.

One aspect of the present invention pertains to use of an assay in a method of classification according to bone state, which assay relies upon one or more diagnostic species, including free proline or a surrogate for free proline.

One aspect of the present invention pertains to a method of classifying a sample, as described herein.

One aspect of the present invention pertains to a method of classifying a subject as described herein.

One aspect of the present invention pertains to a method of diagnosing a subject as described herein.

One aspect of the present invention pertains to a computer system or device, such as a computer or linked computers, operatively configured to implement a method as described herein; and related computer code computer programs, data carriers carrying such code and programs, and the like.

One aspect of the present invention pertains to a method of determining (e.g., an assay for) the proline content of a sample, said method comprising the steps of:
(a) contacting said sample with sodium citrate buffer to form a precipitate;
(b) separating supernatant from said precipitate;
(c) contacting said supernatant with satin to form a mixture; and,
(d) quantifying any resultant blue colored product in said mixture.

One aspect of the present invention pertains to a composition rich in proline, and/or free proline, and/or one or more proline precursors, for the treatment of and/or the prevention of a condition associated with a bone disorder.

One aspect of the present invention pertains to a method of treatment of and/or the prevention of a condition associated with a bone disorder comprising administration of a composition rich in proline, and/or free proline, and/or one or more proline precursors.

One aspect of the present invention pertains to use of a composition rich in proline, and/or free proline, and/or one or more proline precursors in the preparation of a medicament for the treatment of and/or the prevention of a condition associated with a bone disorder.

One aspect of the present invention pertains to a method of therapy of a condition associated with a bone disorder based upon correction of metabolic defect in one or more of (a) proline synthesis, (b) proline transport, (c) proline absorption, and (d) proline loss mechanisms.

One aspect of the present invention pertains to a method of treatment of a condition associated with proline deficiency, comprising chronic administration of paracetamol.

One aspect of the present invention pertains to use of paracetamol in the preparation of a medicament for the treatment of a condition associated with proline deficiency.

One aspect of the present invention pertains to a method of therapeutic monitoring of the treatment of a patient having a condition associated with a bone disorder comprising monitoring proline (e.g., free proline) levels in said patient.

One aspect of the present invention pertains to a genetic test for susceptibility to conditions associated with a bone disorder based upon polymorphisms of enzymes involved in proline metabolism.

One aspect of the present invention pertains to use of an enzyme involved in proline metabolims, and/or an associated compound, as a target for the identification of a compound which is useful in the treatment of a condition associated with a bone disorder.

One aspect of the present invention pertains to a method of identifying a compound which is useful in the treatment of a condition associated with a bone disorder, and which employs an enzyme involved in proline metabolim and/or an associated compound, as a target.

One aspect of the present invention pertains to a compound identified by such a method, which targets an enzyme involved in proline metabolim and/or an associated compound.

One aspect of the present invention pertains to a method of treatment of a condition associated with a bone disorder which involves administration of a compound identified by a method as described herein.

One aspect of the present invention pertains to a compound identified by a method as described herein, for use in a method of treatment of a condition associated with a bone disorder.

One aspect of the present invention pertains to a method of genetically modifying an animal so as to have a predetermined condition associated with a bone disorder.

One aspect of the present invention pertains to a method of genetically modifying an animal so as to have a deficiency in circulating free proline.

One aspect of the present invention pertains to a genetically modified animal so modified.

One aspect of the present invention pertains to use of such an animal for the development and/or testing of a treatment or therapy.

These and other aspects of the present invention are described herein.

As will be appreciated by one of skill in the art, features and preferred embodiments of one aspect of the present invention will also pertain to other aspects of the present invention.

BRIEF DESCRIPTION OF THE DRAWINGS

FIG. 1A-OP is a scores scatter plot for PC2 and PC1 (t2 vs. t1) for the principal components analysis (PCA) model derived from 1-D $^1$H NMR spectra from serum samples from control subjects (triangles, ▲) and patients with osteoporosis (circles, ●).

FIG. 1B-OP is the corresponding loadings scatter plot (p2 vs. p1) for the PCA shown in FIG. 1A-OP.

FIG. 1C-OP is a scores scatter plot for PC2 and PC1 (t2 vs. t1) for the PCA model derived from 1-D $^1$H NMR spectra from serum samples from control subjects (triangles, ▲) and patients with osteoporosis (circles, ●). Prior to PCA, the data were filtered (in this case, using orthogonal signal correction, OSC).

FIG. 1D-OP is the corresponding loadings scatter plot (p2 vs. p1) for the PCA shown in FIG. 1C-OP.

FIG. 1E-OP is a scores scatter plot for PC2 and PC1 (t2 vs. t1) for the PLS-DA model derived from 1-D $^1$H NMR spectra from serum samples from control subjects (triangles, ▲) and patients with osteoporosis (circles, ●). Prior to PLS-DA, the data were filtered (in this case, using orthogonal signal correction, OSC).

FIG. 1F-OP is the corresponding loadings scatter plot (p2 vs. p1) for the PCA shown in FIG. 1E-OP.

FIG. 2A-OP shows a section of the variable importance plot (VIP) derived from the PLS-DA model described in FIG. 1E-OP.

FIG. 2B-OP shows a section of the regression coefficient plot derived from the PLS-DA model described in FIG. 1E-OP.

FIG. 3-OP is a y-predicted scatter plot for a PLS-DA model calculated using ~85% of the control (triangles, ▲) and osteoporosis (circles, ●) samples, which was then used to predict the presence of disease in the remaining 15% of samples (squares, ■) (the validation set).

DETAILED DESCRIPTION OF THE INVENTION

The inventors have developed novel methods (which employ multivariate statistical analysis and pattern recognition (PR) techniques, and optionally data filtering techniques) of analysing data (e.g., NMR spectra) from a test population which yield accurate mathematical models which may subsequently be used to classify a test sample or subject, and/or in diagnosis.

These techniques have been applied to the analysis of blood serum in the context of osteoporosis. For example, the metabonomic analysis can distinguish between individuals with and without osteoporosis. Novel diagnostic biomarkers for osteoporosis have been identified, including free proline, and associated methods for diagnosis have been developed.

The inventors have determined that free proline is a novel biomarker for bone disorders, for example, conditions associated with a bone disorder, e.g., with low bone mineral density, e.g. with osteoporosis.

Furthermore, the inventors have determined that a deficiency of free proline is a diagnostic marker for bone disorders, for example, conditions associated with a bone disorder, e.g., with low bone mineral density, e.g., with osteoporosis. Thus, a decrease in proline levels, as compared to the proline levels in a suitable control, is diagnostic of bone disorders, for example, conditions associated with a bone disorder, e.g., with low bone mineral density, e.g., with osteoporosis.

One aspect of the present invention pertains to one or more diagnostic species (e.g., biomarkers), including free proline or a surrogate for free proline, for use in a method of classification (e.g., diagnosis) according to bone state, e.g., according to bone mineral density, e.g., according to osteoporotic state.

One aspect of the present invention pertains to a method of classification (e.g., diagnosis) according to bone state, e.g., according to bone mineral density, e.g., according to osteoporotic state which employs or relies upon one or more diagnostic species (e.g., biomarkers), including free proline or a surrogate for free proline.

One aspect of the present invention pertains to use of one or more diagnostic species (e.g., biomarkers), including free proline or a surrogate for free proline, in a method of classification (e.g., diagnosis) according to bone state, e.g., according to bone mineral density, e.g., according to osteoporotic state.

One aspect of the present invention pertains to an assay for use in a method of classification (e.g., diagnosis) according to bone state, e.g., according to bone mineral density, e.g., according to osteoporotic state, which assay relies upon one or more diagnostic species (e.g., biomarkers), including free proline or a surrogate for free proline.

One aspect of the present invention pertains to use of an assay in a method of classification (e.g., diagnosis) according to bone state, e.g., according to bone mineral density, e.g., according to osteoporotic state, which assay relies upon one or more diagnostic species (e.g., biomarkers), including free proline or a surrogate for free proline.

Methods of Classifying, Diagnosing

One aspect of the present invention pertains to a method of classifying a sample, as described herein.

One aspect of the present invention pertains to a method of classifying a subject by classifying a sample from said subject, wherein said method of classifying a sample is as described herein.

One aspect of the present invention pertains to a method of diagnosing a subject by classifying a sample from said subject, wherein said method of classifying a sample is as described herein.

Classifying a Sample: By Amount of Diagnostic Species

One aspect of the present invention pertains to a method of classifying a sample, said method comprising the step of relating the amount of, or relative amount of one or more diagnostic species, including free proline or a surrogate for free proline, present in said sample with a predetermined condition associated with a bone disorder, e.g., with low bone mineral density, e.g., with osteoporosis.

One aspect of the present invention pertains to a method of classifying a sample from a subject, said method comprising the step of relating the amount of, or relative amount of one or more diagnostic species, including free proline or a surrogate for free proline, present in said sample with a predetermined condition associated with a bone disorder, e.g., with low bone mineral density, e.g., with osteoporosis of said subject.

One aspect of the present invention pertains to a method of classifying a sample, said method comprising the step of relating the amount of, or relative amount of one or more diagnostic species, including free proline or a surrogate for free proline, present in said sample with the presence or absence of a predetermined condition associated with a bone disorder, e.g., with low bone mineral density, e.g., with osteoporosis.

One aspect of the present invention pertains to a method of classifying a sample from a subject, said method comprising the step of relating the amount of, or the relative amount of, one or more diagnostic species, including free proline or a surrogate for free proline, present in said sample with the presence or absence of a predetermined condition associated with a bone disorder, e.g., with low bone mineral density, e.g., with osteoporosis of said subject.

One aspect of the present invention pertains to a method of classifying a sample, said method comprising the step of relating a modulation of (e.g., decrease in) the amount of, or relative amount of one or more diagnostic species, including free proline or a surrogate for free proline, present in said sample, as compared to a control sample, with a predetermined condition associated with a bone disorder, e.g., with low bone mineral density, e.g., with osteoporosis.

One aspect of the present invention pertains to a method of classifying a sample from a subject, said method comprising the step of relating a modulation of (e.g., decrease in) the amount of, or relative amount of one or more diagnostic species, including free proline or a surrogate for free proline, present in said sample, as compared to a control sample, with a predetermined condition associated with a bone disorder, e.g., with low bone mineral density, e.g., with osteoporosis of said subject.

One aspect of the present invention pertains to a method of classifying a sample, said method comprising the step of relating a modulation of (e.g., decrease in) the amount of, or relative amount of one or more diagnostic species, including free proline or a surrogate for free proline, present in said sample, as compared to a control sample, with the presence or absence of a predetermined condition associated with a bone disorder, e.g., with low bone mineral density, e.g., with osteoporosis.

One aspect of the present invention pertains to a method of classifying a sample from a subject, said method comprising the step of relating a modulation of (e.g., decrease in) the amount of, or relative amount of one or more diagnostic species, including free proline or a surrogate for free proline, present in said sample, as compared to a control sample, with the presence or absence of a predetermined condition associated with a bone disorder, e.g., with low bone mineral density, e.g., with osteoporosis of said subject.

Classifying a Subject: By Amount of Diagnostic Species

One aspect of the present invention pertains to a method of classifying a subject, said method comprising the step of relating the amount of, or relative amount of one or more diagnostic species, including free proline or a surrogate for free proline, present in a sample from said subject with a predetermined condition associated with a bone disorder, e.g., with low bone mineral density, e.g., with osteoporosis of said subject.

One aspect of the present invention pertains to a method of classifying a subject, said method comprising the step of relating the amount of, or relative amount of one or more diagnostic species, including free proline or a surrogate for free proline, present in a sample from said subject with the presence or absence of a predetermined condition associated with a bone disorder, e.g., with low bone mineral density, e.g., with osteoporosis of said subject.

One aspect of the present invention pertains to a method of classifying a subject, said method comprising the step of relating a modulation of (e.g., decrease in) the amount of, or relative amount of one or more diagnostic species, including free proline or a surrogate for free proline, present in a sample from said subject, as compared to a control sample, with a predetermined condition associated with a bone disorder, e.g., with low bone mineral density, e.g., with osteoporosis of said subject.

One aspect of the present invention pertains to a method of classifying a subject, said method comprising the step of relating a modulation of (e.g., decrease in) the amount of, or relative amount of one or more diagnostic species, including free proline or a surrogate for free proline, present in a sample from said subject, as compared to a control sample, with the presence or absence of a predetermined condition associated with a bone disorder, e.g., with low bone mineral density, e.g., with osteoporosis of said subject.

Diagnosing a Subject: By Amount of Diagnostic Species

One aspect of the present invention pertains to a method of diagnosing a predetermined condition associated with a bone disorder, e.g., with low bone mineral density, e.g., with osteoporosis of a subject, said method comprising the step of relating the amount of, or relative amount of one or more diagnostic species, including free proline or a surrogate for free proline, present in a sample from said subject with said predetermined condition of said subject.

One aspect of the present invention pertains to a method of diagnosing a predetermined condition associated with a bone disorder, e.g., with low bone mineral density, e.g., with osteoporosis of a subject, said method comprising the step of relating the amount of, or relative amount of one or more diagnostic species, including free proline or a surrogate for free proline, present in a sample from said subject with the presence or absence of said predetermined condition of said subject.

One aspect of the present invention pertains to a method of diagnosing a predetermined condition associated with a bone disorder, e.g., with low bone mineral density, e.g., with osteoporosis of a subject, said method comprising the step of relating a modulation of (e.g., decrease in) the amount of, or relative amount of one or more diagnostic species, including free proline or a surrogate for free proline, present in a sample from said subject, as compared to a control sample, with said predetermined condition of said subject.

One aspect of the present invention pertains to a method of diagnosing a predetermined condition associated with a bone disorder, e.g., with low bone mineral density, e.g., with osteoporosis of a subject, said method comprising the step of relating a modulation of (e.g., decrease in) the amount of, or relative amount of one or more diagnostic species, including free proline or a surrogate for free proline, present in a sample from said subject, as compared to a control sample, with the presence or absence of said predetermined condition of said subject.

Classifying a Sample: By NMR Spectral Intensity

One aspect of the present invention pertains to a method of classifying a sample, said method comprising the step of relating NMR spectral intensity at one or more predetermined diagnostic spectral windows associated with one or more diagnostic species, including free proline or a surrogate for free proline, for said sample with a predetermined condition associated with a bone disorder, e.g., with low bone mineral density, e.g., with osteoporosis.

One aspect of the present invention pertains to a method of classifying a sample from a subject, said method comprising the step of relating NMR spectral intensity at one or more predetermined diagnostic spectral windows associated with one or more diagnostic species, including free proline or a surrogate for free proline, for said sample with a predetermined condition associated with a bone disorder, e.g., with low bone mineral density, e.g., with osteoporosis of said subject.

One aspect of the present invention pertains to a method of classifying a sample, said method comprising the step of relating NMR spectral intensity at one or more predetermined diagnostic spectral windows associated with one or more diagnostic species, including free proline or a surrogate for free proline, for said sample with the presence or absence of a predetermined condition associated with a bone disorder, e.g., with low bone mineral density, e.g., with osteoporosis.

One aspect of the present invention pertains to a method of classifying a sample from a subject, said method comprising the step of relating NMR spectral intensity at one or more predetermined diagnostic spectral windows associated with one or more diagnostic species, including free proline or a surrogate for free proline, for said sample with the presence or absence of a predetermined condition associated with a bone disorder, e.g., with low bone mineral density, e.g., with osteoporosis of said subject.

One aspect of the present invention pertains to a method of classifying a sample, said method comprising the step of relating a modulation of (e.g., decrease in) NMR spectral intensity, relative to a control value, at one or more predetermined diagnostic spectral windows associated with one or more diagnostic species, including free proline or a surrogate for free proline, for said sample with a predetermined condition associated with a bone disorder, e.g., with low bone mineral density, e.g., with osteoporosis.

One aspect of the present invention pertains to a method of classifying a sample from a subject, said method comprising the step of relating a modulation of (e.g., decrease in) NMR spectral intensity, relative to a control value, at one or more predetermined diagnostic spectral windows associated with one or more diagnostic species, including free proline or a surrogate for free proline, for said sample with a predetermined condition associated with a bone disorder, e.g., with low bone mineral density, e.g., with osteoporosis of said subject.

One aspect of the present invention pertains to a method of classifying a sample, said method comprising the step of relating a modulation of (e.g., decrease in) NMR spectral intensity, relative to a control value, at one or more predetermined diagnostic spectral windows associated with one or more diagnostic species, including free proline or a surrogate for free proline, for said sample with the presence or absence of a predetermined condition associated with a bone disorder, e.g., with low bone mineral density, e.g., with osteoporosis.

One aspect of the present invention pertains to a method of classifying a sample from a subject, said method comprising the step of relating a modulation of (e.g., decrease in) NMR spectral intensity, relative to a control value, at one or more predetermined diagnostic spectral windows associated with one or more diagnostic species, including free proline or a surrogate for free proline, for said sample with the presence or absence of a predetermined condition associated with a bone disorder, e.g., with low bone mineral density, e.g., with osteoporosis of said subject.

Classifying a Subject: By NMR Spectral Intensity

One aspect of the present invention pertains to a method of classifying a subject, said method comprising the step of relating NMR spectral intensity at one or more predetermined diagnostic spectral windows associated with one or more diagnostic species, including free proline or a surrogate for free proline, for a sample from said subject with a predetermined condition of said subject associated with a bone disorder, e.g., with low bone mineral density, e.g., with osteoporosis.

One aspect of the present invention pertains to a method of classifying a subject, said method comprising the step of relating NMR spectral intensity at one or more predetermined diagnostic spectral windows associated with one or more diagnostic species, including free proline or a surrogate for free proline, for a sample from said subject with the presence or absence of a predetermined condition of said subject associated with a bone disorder, e.g., with low bone mineral density, e.g., with osteoporosis.

One aspect of the present invention pertains to a method of classifying a subject, said method comprising the step of relating a modulation of (e.g., decrease in) NMR spectral intensity, relative to a control value, at one or more predetermined diagnostic spectral windows associated with one or more diagnostic species, including free proline or a surrogate for free proline, for a sample from said subject with a predetermined condition of said subject associated with a bone disorder, e.g., with low bone mineral density, e.g., with osteoporosis.

One aspect of the present invention pertains to a method of classifying a subject, said method comprising the step of relating a modulation of (e.g., decrease in) NMR spectral intensity, relative to a control value, at one or more predetermined diagnostic spectral windows associated with one or more diagnostic species, including free proline or a surrogate for free proline, for a sample from said subject with the presence or absence of a predetermined condition of said subject associated with a bone disorder, e.g., with low bone mineral density, e.g., with osteoporosis.

Diagnosing a Subject: By NMR Spectral Intensity

One aspect of the present invention pertains to a method of diagnosing a predetermined condition of a subject, said method comprising the step of relating NMR spectral intensity at one or more predetermined diagnostic spectral windows associated with one or more diagnostic species, including free proline or a surrogate for free proline, for a sample from said subject with said predetermined condition associated with a bone disorder, e.g., with low bone mineral density, e.g., with osteoporosis of said subject.

One aspect of the present invention pertains to a method of diagnosing a predetermined condition of a subject, said method comprising the step of relating NMR spectral intensity at one or more predetermined diagnostic spectral windows associated with one or more diagnostic species, including free proline or a surrogate for free proline, for a sample from said subject with the presence or absence of said predetermined condition associated with a bone disorder, e.g., with low bone mineral density, e.g., with osteoporosis of said subject.

One aspect of the present invention pertains to a method of diagnosing a predetermined condition of a subject, said method comprising the step of relating a modulation of (e.g., decrease in) NMR spectral intensity, relative to a control value, at one or more predetermined diagnostic spectral windows associated with one or more diagnostic species, including free proline or a surrogate for free proline, for a sample from said subject with said predetermined condition associated with a bone disorder, e.g., with low bone mineral density, e.g., with osteoporosis of said subject.

One aspect of the present invention pertains to a method of diagnosing a predetermined condition of a subject, said method comprising the step of relating a modulation of (e.g., decrease in) NMR spectral intensity, relative to a control value, at one or more predetermined diagnostic spectral windows associated with one or more diagnostic species, including free proline or a surrogate for free proline, for a sample from said subject with the presence or absence of said predetermined condition associated with a bone disorder, e.g., with low bone mineral density, e.g., with osteoporosis of said subject.

Classifying a Sample: By Mathematical Modelling

One aspect of the present invention pertains to a method of classification, said method comprising the steps of:
(a) forming a predictive mathematical model by applying a modelling method to modelling data;
wherein said model takes account of one or more diagnostic species, including free proline or a surrogate for free proline; and,
(b) using said model to classify a test sample according to bone state, e.g., according to bone mineral density, e.g., according to osteoporotic state.

One aspect of the present invention pertains to a method of classifying a test sample, said method comprising the steps of:
(a) forming a predictive mathematical model by applying a modelling method to modelling data;
wherein said modelling data comprises a plurality of data sets for modelling samples of known class associated with a bone disorder, e.g., with low bone mineral density, e.g., with osteoporosis;
wherein said model takes account of one or more diagnostic species, including free proline or a surrogate for free proline; and,
(b) using said model to classify said test sample as being a member of one of said known classes.

One aspect of the present invention pertains to a method of classifying a test sample, said method comprising the steps of:
(a) forming a predictive mathematical model by applying a modelling method to modelling data;
wherein said modelling data comprises at least one data set for each of a plurality of modelling samples;
wherein said modelling samples define a class group consisting of a plurality of classes associated with a bone disorder, e.g., with low bone mineral density, e.g., with osteoporosis;
wherein each of said modelling samples is of a known class selected from said class group;
wherein said model takes account of one or more diagnostic species, including free proline or a surrogate for free proline; and,
(b) using said model with a data set for said test sample to classify said test sample as being a member of one class selected from said class group.

One aspect of the present invention pertains to a method of classification, said method comprising the step of:
using a predictive mathematical model;
wherein said model is formed by applying a modelling method to modelling data;
wherein said model takes account of one or more diagnostic species, including free proline or a surrogate for free proline;

to classify a test sample according to bone state, e.g., according to bone mineral density, e.g., according to osteoporotic state.

One aspect of the present invention pertains to a method of classifying a test sample, said method comprising the step of:
using a predictive mathematical model;
wherein said model is formed by applying a modelling method to modelling data;
wherein said modelling data comprises a plurality of data sets for modelling samples of known class associated with a bone disorder, e.g., with low bone mineral density, e.g., with osteoporosis;
wherein said model takes account of one or more diagnostic species, including free proline or a surrogate for free proline;
to classify said test sample as being a member of one of said known classes.

One aspect of the present invention pertains to a method of classifying a test sample, said method comprising the step of:
using a predictive mathematical model;
wherein said model is formed by applying a modelling method to modelling data;
wherein said modelling data comprises at least one data set for each of a plurality of modelling samples;
wherein said modelling samples define a class group consisting of a plurality of classes associated with a bone disorder, e.g., with low bone mineral density, e.g., with osteoporosis;
wherein each of said modelling samples is of a known class selected from said class group;
wherein said model takes account of one or more diagnostic species, including free proline or a surrogate for free proline;
with a data set for said test sample to classify said test sample as being a member of one class selected from said class group.

Classifying a Subject: By Mathematical Modelling

One aspect of the present invention pertains to a method of classification, said method comprising the steps of:
(a) forming a predictive mathematical model by applying a modelling method to modelling data;
wherein said model takes account of one or more diagnostic species, including free proline or a surrogate for free proline; and,
(b) using said model to classify a subject according to bone state, e.g., according to bone mineral density, e.g., according to osteoporotic state.

One aspect of the present invention pertains to a method of classifying a subject, said method comprising the steps of:
(a) forming a predictive mathematical model by applying a modelling method to modelling data;
wherein said modelling data comprises a plurality of data sets for modelling samples of known class according to bone state, e.g., according to bone mineral density, e.g., according to osteoporotic state;
wherein said model takes account of one or more diagnostic species, including free proline or a surrogate for free proline; and,
(b) using said model to classify a test sample from said subject as being a member of one of said known classes, and thereby classify said subject.

One aspect of the present invention pertains to a method of classifying a subject, said method comprising the steps of:
(a) forming a predictive mathematical model by applying a modelling method to modelling data;
wherein said modelling data comprises at least one data set for each of a plurality of modelling samples;
wherein said modelling samples define a class group consisting of a plurality of classes associated with a bone disorder, e.g., with low bone mineral density, e.g., with osteoporosis;
wherein each of said modelling samples is of a known class selected from said class group;
wherein said model takes account of one or more diagnostic species, including free proline or a surrogate for free proline; and,
(b) using said model with a data set for a test sample from said subject to classify said test sample as being a member of one class selected from said class group, and thereby classify said subject.

One aspect of the present invention pertains to a method of classification, said method comprising the step of:
using a predictive mathematical model;
wherein said model is formed by applying a modelling method to modelling data;
wherein said model takes account of one or more diagnostic species, including free proline or a surrogate for free proline;
to classify a subject according to bone state, e.g., according to bone mineral density, e.g., according to osteoporotic state.

One aspect of the present invention pertains to a method of classifying a subject, said method comprising the step of:
using a predictive mathematical model
wherein said model is formed by applying a modelling method to modelling data;
wherein said modelling data comprises a plurality of data sets for modelling samples of known class associated with a bone disorder, e.g., with low bone mineral density, e.g., with osteoporosis;
wherein said model takes account of one or more diagnostic species, including free proline or a surrogate for free proline;
to classify a test sample from said subject as being a member of one of said known classes, and thereby classify said subject.

One aspect of the present invention pertains to a method of classifying a subject, said method comprising the step of:
using a predictive mathematical model,
wherein said model is formed by applying a modelling method to modelling data;
wherein said modelling data comprises at least one data set for each of a plurality of modelling samples;
wherein said modelling samples define a class group consisting of a plurality of classes associated with a bone disorder, e.g., with low bone mineral density, e.g., with osteoporosis;
wherein each of said modelling samples is of a known class selected from said class group;
wherein said model takes account of one or more diagnostic species, including free proline or a surrogate for free proline;
with a data set for a test sample from said subject to classify said test sample as being a member of one class selected from said class group, and thereby classify said subject.

Diagnosing a Subject: By Mathematical Modelling

One aspect of the present invention pertains to a method of diagnosis of a predetermined condition associated with a bone disorder, e.g., with low bone mineral density, e.g., with osteoporosis, said method comprising the steps of:
(a) forming a predictive mathematical model by applying a modelling method to modelling data;

wherein said model takes account of one or more diagnostic species, including free proline or a surrogate for free proline; and, (b) using said model to diagnose a subject.

One aspect of the present invention pertains to a method of diagnosing a predetermined condition associated with a bone disorder, e.g., with low bone mineral density, e.g., with osteoporosis of a subject, said method comprising the steps of:

(a) forming a predictive mathematical model by applying a modelling method to modelling data;

wherein said modelling data comprises a plurality of data sets for modelling samples of known class;

wherein said model takes account of one or more diagnostic species, including free proline or a surrogate for free proline; and, (b) using said model to classify a test sample from said subject as being a member of one of said known classes, and thereby diagnose said subject.

One aspect of the present invention pertains to a method of diagnosing a predetermined condition associated with a bone disorder, e.g., with low bone mineral density, e.g., with osteoporosis of a subject, said method comprising the steps of:

(a) forming a predictive mathematical model by applying a modelling method to modelling data;

wherein said modelling data comprises at least one data set for each of a plurality of modelling samples;

wherein said modelling samples define a class group consisting of a plurality of classes;

wherein each of said modelling samples is of a known class selected from said class group;

wherein said model takes account of one or more diagnostic species, including free proline or a surrogate for free proline; and, (b) using said model with a data set for a test sample from said subject to classify said test sample as being a member of one class selected from said class group, and thereby diagnose said subject.

One aspect of the present invention pertains to a method of diagnosis of a predetermined condition associated with a bone disorder, e.g., with low bone mineral density, e.g., with osteoporosis, said method comprising the step of:

using a predictive mathematical model;

wherein said model is formed by applying a modelling method to modelling data;

wherein said model takes account of one or more diagnostic species, including free proline or a surrogate for free proline;

to diagnose a subject.

One aspect of the present invention pertains to a method of diagnosing a predetermined condition associated with a bone disorder, e.g., with low bone mineral density, e.g., with osteoporosis of a subject, said method comprising the step of:

using a predictive mathematical model;

wherein said model is formed by applying a modelling method to modelling data;

wherein said modelling data comprises a plurality of data sets for modelling samples of known class;

wherein said model takes account of one or more diagnostic species, including free proline or a surrogate for free proline;

to classify a test sample from said subject as being a member of one of said known classes, and thereby diagnose said subject.

One aspect of the present invention pertains to a method of diagnosing a predetermined condition associated with a bone disorder, e.g., with low bone mineral density, e.g., with osteoporosis of a subject, said method comprising the step of:

using a predictive mathematical model;

wherein said model is formed by applying a modelling method to modelling data;

wherein said modelling data comprises at least one data set for each of a plurality of modelling samples;

wherein said modelling samples define a class group consisting of a plurality of classes;

wherein each of said modelling samples is of a known class selected from said class group;

wherein said model takes account of one or more diagnostic species, including free proline or a surrogate for free proline;

with a data set for a test sample from said subject to classify said test sample as being a member of one class selected from said class group, and thereby diagnose said subject.

Certain Preferred Embodiments

In one embodiment, said sample is a sample from a subject, and said predetermined condition is a predetermined condition of said subject.

In one embodiment, said test sample is a test sample from a subject, and said predetermined condition is a predetermined condition of said subject.

In one embodiment, said classification, classifying, or diagnosis according to bone state is according to bone mineral density.

In one embodiment, said classification, classifying, or diagnosis according to bone state is according to osteoporotic state.

In one embodiment, said predetermined condition is a predetermined condition associated with low bone mineral density.

In one embodiment, said predetermined condition is a predetermined condition associated with osteoporosis.

In one embodiment, said one or more predetermined diagnostic spectral windows are associated with one or more diagnostic species.

In one embodiment, said relating step involves the use of a predictive mathematical model; for example, as described herein.

The nature of a predictive mathematical model is determined primarily by the modelling method employed when forming that model.

In one embodiment, said modelling method is a multivariate statistical analysis modelling method.

In one embodiment, said modelling method is a multivariate statistical analysis modelling method which employs a pattern recognition method.

In one embodiment, said modelling method is, or employs PCA.

In one embodiment, said modelling method is, or employs PLS.

In one embodiment, said modelling method is, or employs PLS-DA.

In one embodiment, said modelling method includes a step of data filtering.

In one embodiment, said modelling method includes a step of orthogonal data filtering.

In one embodiment, said modelling method includes a step of OSC.

In one embodiment, said model takes account of one or more diagnostic species, including free proline or a surrogate for free proline.

The precise details of the predictive mathematical model are determined primarily by the modelling data (e.g., modelling data sets).

In one embodiment, said modelling data comprise spectral data.

In one embodiment, said modelling data comprise both spectral data and non-spectral data (and is referred to as a "composite data").

In one embodiment, said modelling data comprise NMR spectral data.

In one embodiment, said modelling data comprise both NMR spectral data and non-NMR spectral data.

In one embodiment, said modelling data comprise spectra.

In one embodiment, said modelling data are spectra.

In one embodiment, said modelling data comprises a plurality of data sets for modelling samples of known class.

In one embodiment, said modelling data comprises at least one data set for each of a plurality of modelling samples.

In one embodiment, said modelling data comprises exactly one data set for each of a plurality of modelling samples.

In one embodiment, said using step is: using said model with a data set for said test sample to classify said test sample as being a member of one class selected from said class group.

In one embodiment, each of said data sets comprises spectral data.

In one embodiment, each of said data sets comprises both spectral data and non-spectral data (and is referred to as a "composite data set").

In one embodiment, each of said data sets comprises NMR spectral data.

In one embodiment, each of said data sets comprises both NMR spectral data and non-NMR spectral data.

In one embodiment, said NMR spectral data comprises $^1$H NMR spectral data and/or $^{13}$C NMR spectral data.

In one embodiment, said NMR spectral data comprises $^1$H NMR spectral data.

In one embodiment, each of said data sets comprises a spectrum.

In one embodiment, each of said data sets comprises a $^1$H NMR spectrum and/or $^{13}$C NMR spectrum.

In one embodiment, each of said data sets comprises a $^1$H NMR spectrum.

In one embodiment, each of said data sets is a spectrum.

In one embodiment, each of said data sets is a $^1$H NMR spectrum and/or $^{13}$C NMR spectrum.

In one embodiment, each of said data sets is a $^1$H NMR spectrum.

In one embodiment, said non-spectral data is non-spectral clinical data.

In one embodiment, said non-NMR spectral data is non-spectral clinical data.

In one embodiment, said class group comprises classes associated with said predetermined condition (e.g., presence, absence, degree, etc.).

In one embodiment, said class group comprises exactly two classes.

In one embodiment, said class group comprises exactly two classes: presence of said predetermined condition; and absence of said predetermined condition.

Classification, Classifying, and Classes

As discussed above, many aspects of the present invention pertain to methods of classifying things, for example, a sample, a subject, etc. In such methods, the thing is classified, that is, it is associated with an outcome, or, more specifically, it is assigned membership to a particular class (i.e., it is assigned class membership), and is said "to be of," "to belong to," "to be a member of," a particular class.

Classification is made (i.e., class membership is assigned) on the basis of diagnostic criteria. The step of considering such diagnostic criteria, and assigning class membership, is described by the word "relating," for example, in the phrase "relating NMR spectral intensity at one or more predetermined diagnostic spectral windows for said sample (i.e., diagnostic criteria) with the presence or absence of a predetermined condition (i.e., class membership)."

For example, "presence of a predetermined condition" is one class, and "absence of a predetermined condition" is another class; in such cases, classification (i.e., assignment to one of these classes) is equivalent to diagnosis.

Bone Disorders

As used herein, the term "condition" relates to a state which is, in at least one respect, distinct from the state of normality, as determined by a suitable control population.

A condition may be pathological (e.g., a disease, referred to herein as an "indication") or physiological (e.g., phenotype, genotype, fasting, water load, exercise, hormonal cycles, e.g., oestrus, etc.).

Included among conditions is the state of "at risk of" a condition, "predisposition towards a" condition, and the like, again as compared to the state of normality, as determined by a suitable control population. In this way, osteoporosis, at risk of osteoporosis, and predisposition towards osteoporosis are all conditions (and are also conditions associated with osteoporosis).

Where the condition is the state of "at risk of," "predisposition towards," and the like, a method of diagnosis may be considered to be a method of prognosis.

In this context, the phrases "at risk of," "predisposition towards," and the like, indicate a probability of being classified/diagnosed (or being able to be classified/diagnosed) with the predetermined condition which is greater (e.g., 1.5×, 2×, 5×, 10×, etc.) than for the corresponding control. Often, a time period (e.g., within the next 5 years, 10 years, 20 years, etc.) is associated with the probability. For example, a subject who is 2× more likely to be diagnosed with the predetermined condition within the next 5 years, as compared to a suitable control, is "at risk of" that condition.

Included among conditions is the degree of a condition, for example, the progress or phase of a disease, or a recovery therefrom. For example, each of different states in the progress of a disease, or in the recovery from a disease, are themselves conditions. In this way, the degree of a condition may refer to how temporally advanced the condition is. Another example of a degree of a condition relates to its maximum severity, e.g., a disease can be classified as mild, moderate or severe). Yet another example of a degree of a condition relates to the nature of the condition (e.g., anatomical site, extent of tissue involvement, etc.).

In the present invention, said predetermined condition is a predetermined condition which is associated with a bone disorder, e.g., is a bone disorder (e.g., as described above).

In one embodiment, said predetermined condition is a predetermined condition which is associated with (e.g., characterised by) low bone mineral density.

In one embodiment, said predetermined condition is a predetermined condition which is associated with osteoporosis.

In one embodiment, said predetermined condition is osteoporosis or predisposition towards osteoporosis.

In one embodiment, said predetermined condition is osteoporosis.

In one embodiment, said predetermined condition is predisposition towards osteoporosis.

In one embodiment, said predetermined condition is osteoporosis of the spine, hip, or wrist.

In one embodiment, said predetermined condition is predisposition towards osteoporosis of the spine, hip, or wrist.

In one embodiment, said osteoporosis is osteoporosis as defined by the World Health Organisation (WHO), as a bone mineral density (BMD) below a cut-off value which is 1.5 standard deviations (SDs) below the mean value for age- and sex-matched controls (Z-scores) (see, e.g., World Health Organisation, 1994).

In one embodiment, said osteoporosis is osteoporosis as defined by the World Health Organisation (WHO), as a bone mineral density (BMD) below a cut-off value which is 2.5 standard deviations (SDs) below the mean value for sex-matched controls (T-scores) (see, e.g., World Health Organisation, 1994).

Organisms, Subjects, Patients

In one embodiment, said organism (e.g., subject, patient) is an animal having bones.

In one embodiment, said organism (e.g., subject, patient) is a mammal.

In one embodiment, said organism (e.g., subject, patient) is a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the organism may be any of its forms of development, for example, a foetus.

In one embodiment, said organism (e.g., subject, patient) is a human.

The subject (e.g., a human) may be characterised by one or more criteria, for example, sex, age (e.g., 40 years or more, 50 years or more, 60 years or more, etc.), ethnicity, medical history, lifestyle (e.g., smoker, non-smoker), hormonal status (e.g., pre-menopausal, post-menopausal), etc.

The term "population," as used herein, refers to a group of organisms (e.g., subjects, patients). If desired, a population (e.g., of humans) may be selected according to one or more of the criteria listed above.

Diagnostic Species and Biomarkers

In one embodiment, said one or more diagnostic species is a plurality of diagnostic species (i.e., a combination of diagnostic species) including free proline or a surrogate for free proline; that is, at least one of said one or more diagnostic species is free proline or a surrogate for free proline.

In one embodiment, said one or more diagnostic species is a single diagnostic species and is free proline or a surrogate for free proline.

In one embodiment, said one or more diagnostic species is a single diagnostic species and is free proline.

The term "free proline," as used herein, refers to proline per se, whether in the L-form or D-form, but preferably the L-form (i.e., the form found in most naturally occurring proteins). The free proline may be in a neutral form or in an ionic form (e.g., a zwitterionic form), as is usually the case in solution at physiological pH. The free proline may have associated with it one or more counterions, which may be organic or inorganic. The free proline may also have reversible reacted with another chemical species (e.g., bicarbonate ion to give a proline carbamate adduct). The proline may also be bound through non-covalent interactions to another species (e.g., proline bound non-covalently to albumin).

The term "free proline," as used herein, specifically excludes incorporated proline, that is proline incorporated in a peptide, dipeptide, oligopeptide, or polypeptide, more specifically, proline incorporated in a molecule which contain proline moieties coupled through amide bonds, for example, as a prolyl moiety in peptides and proteins.

The term "free proline," as used herein, also specifically excludes hydroxyproline (e.g., 4-hydroxyproline).

In one embodiment, said one or more diagnostic species is a plurality of diagnostic species (i.e., a combination of diagnostic species) including: (a) free proline or a surrogate for free proline; and (b) one or more selected from lipids, choline, 3-hydroxybutyrate, lactate, alanine, creatine, creatinine, glucose, and aromatic amino acids.

The term "surrogate for free proline," as used herein, pertains to a chemical species which is indicative, qualitatively or more preferably quantitatively, of the presence of, or more preferably the amount of, free proline.

In one embodiment, said surrogate for free proline is a metabolic precursor to free proline.

In one embodiment, said surrogate for free proline is a metabolic product of free proline.

In one embodiment, at least one of said one or more predetermined diagnostic species is a species described in Table 4-1-OP and/or Table 4-2-OP, including free proline.

In one embodiment, each of a plurality of said one or more predetermined diagnostic species is a species described in Table 4-1-OP and/or Table 4-2-OP, including free proline.

In one embodiment, each of said one or more predetermined diagnostic species is a species described in Table 4-1-OP and/or Table 4-2-OP, including free proline.

Amount or Relative Amount

As discussed above, many of the methods of the present invention involve classification on the basis of an amount, or a relative amount, of one or more diagnostic species.

In one embodiment, said classification is performed on the basis of an amount, or a relative amount, of a single diagnostic species.

In one embodiment, said classification is performed on the basis of an amount, or a relative amount, of a plurality of diagnostic species.

In one embodiment, said classification is performed on the basis of an amount, or a relative amount, of each of a plurality of diagnostic species.

In one embodiment, said classification is performed on the basis of a total amount, or a relative total amount, of a plurality of diagnostic species.

In one embodiment, said one or more predetermined diagnostic spectral windows is: a plurality of diagnostic spectral windows; and, said NMR spectral intensity at one or more predetermined diagnostic spectral windows is: a combination of a plurality of NMR spectral intensities, each of which is NMR spectral intensity for one of said plurality of predetermined diagnostic spectral windows.

In one embodiment, said combination is a linear combination.

The term "amount," as used in this context, pertains to the amount regardless of the terms of expression.

The term "amount," as used herein in the context of "amount of, or relative amount of (e.g., diagnostic) species," pertains to the amount regardless of the terms of expression.

Absolute amounts may be expressed, for example, in terms of mass (e.g., µg), moles (e.g., µmol), volume (i.e., µL), concentration (molarity, µg/mL, µg/g, wt %, vol %, etc.), etc.

Relative amounts may be expressed, for example, as ratios of absolute amounts (e.g., as a fraction, as a multiple, as a %) with respect to another chemical species. For example, the amount may expressed as a relative amount, relative to an internal standard, for example, another chemical species which is endogenous or added.

The amount may be indicated indirectly, in terms of another quantity (possibly a precursor quantity) which is indicative of the amount. For example, the other quantity may be a spectrometric or spectroscopic quantity (e.g., signal, intensity, absorbance, transmittance, extinction coefficient, conductivity, etc.; optionally processed, e.g., integrated) which itself indicative of the amount.

The amount may be indicated, directly or indirectly, in regard to a different chemical species (e.g., a metabolic precursor, a metabolic product, etc.), which is indicative the amount.

Diagnostic Shift

As discussed above, many of the methods of the present invention involve classification on the basis of a modulation, e.g., of NMR spectral intensity at one or more predetermined diagnostic spectral windows; of the amount, or a relative amount, of diagnostic species; etc. In this context, "modulation" pertains to a change, and may be, for example, an increase or a decrease. In one embodiment, said "a modulation of" is "an increase or decrease in." In one embodiment, said "a modulation of" is "a decrease in."

In one embodiment, the modulation (e.g., increase, decrease) is at least 10%, as compared to a suitable control. In one embodiment, the modulation (e.g., increase, decrease) is at least 20%, as compared to a suitable control. In one embodiment, the modulation is a decrease of at least 50% (i.e., a factor of 0.5). In one embodiment, the modulation is a increase of at least 100% (i.e., a factor of 2).

Each of a plurality of predetermined diagnostic spectral windows, and each of a plurality of diagnostic species, may have independent modulations, which may be the same or different. For example, if there are two predetermined diagnostic spectral windows, NMR spectral intensity may increase in one window and decrease in the other window. In this way, combinations of modulations of NMR spectral intensity in different diagnostic spectral windows may be diagnostic. Similarly, if there are two diagnostic species, the amount of one may increase, and the amount of the other may decrease. Again, combinations of modulations of amounts, or relative amounts of, different diagnostic species may be diagnostic. See, for example, the data in the Examples below, which illustrate cases where different species have different modulations.

The term "diagnostic shift," as used herein, pertains a modulation (e.g., decrease), as compared to a suitable control.

A diagnostic shift may be in regard to, for example, NMR spectral intensity at one or more predetermined diagnostic spectral windows; or the amount of; or relative amount of, diagnostic species (e.g., proline).

In one embodiment, said decrease in the amount of, or relative amount of, diagnostic species (e.g., proline), is at least 10%, as compared to a suitable control. For example, if the control level is determined to be 250 µM proline in blood serum, an observed sample level of 225 µM (i.e., 90%) would correspond to a decrease of 10%.

In one embodiment, said decrease is at least 20%.
In one embodiment, said decrease is at least 30%.
In one embodiment, said decrease is at least 40%.
In one embodiment, said decrease is at least 50%.
In one embodiment, said decrease is at least 60%.
In one embodiment, said decrease is at least 70%.
In one embodiment, said decrease is at least 80%.
In one embodiment, said decrease is at least 90%.

In one embodiment, said sample is a blood serum sample, and said decrease in the amount of, or relative amount of, diagnostic species (e.g., free proline), is to a level of 230 µM or less.

In one embodiment, said sample is a blood serum sample, and the amount of, or relative amount of, diagnostic species (e.g., free proline), is a level of 230 µM or less.

In one embodiment, said level is 220 µM or less.
In one embodiment, said level is 210 µM or less.
In one embodiment, said level is 200 µM or less.
In one embodiment, said level is 180 µM or less.
In one embodiment, said level is 160 µM or less.
In one embodiment, said level is 140 µM or less.
In one embodiment, said level is 120 µM or less.
In one embodiment, said level is 100 µM or less.

Control Samples, Control Subjects, Control Data

Suitable controls are usually selected on the basis of the organism (e.g., subject, patient) under study (test subject, study subject, etc.), and the nature of the study (e.g., type of sample, type of spectra, etc.). Usually, controls are selected to represent the state of "normality." As described herein, deviations from normality (e.g., higher than normal, lower than normal) in test data, test samples, test subjects, etc. are used in classification, diagnosis, etc.

For example, in most cases, control subjects are the same species as the test subject and are chosen to be representative of the equivalent normal (e.g., healthy) organism. A control population is a population of control subjects. If appropriate, control subjects may have characteristics in common (e.g., sex, ethnicity, age group, etc.) with the test subject. If appropriate, control subjects may have characteristics (e.g., age group, etc.) which differ from those of the test subject. For example, it may be desirable to choose healthy 20-year olds of the same sex and ethnicity as the study subject as control subjects.

In most cases, control samples are taken from control subjects. Usually, control samples are of the same sample type (e.g., serum), and are collected and handled (e.g., treated, processed, stored) under the same or similar conditions, as the sample under study (e.g., test sample, study sample).

In most cases, control data (e.g., control values) are obtained from control samples which are taken from control subjects. Usually, control data (e.g., control data sets, control spectral data, control spectra, etc.) are of the same type (e.g., 1-D $^1$H NMR, etc.), and are collected and handled (e.g., recorded, processed) under the same or similar conditions (e.g., parameters), as the test data.

Diagnostic Spectral Windows

As discussed above, many of the methods of the present invention involve relating NMR spectral intensity at one or more predetermined diagnostic spectral windows (e.g., for free proline) with a predetermined condition (e.g., associated with a bone disorder; with a low bone mineral density; osteoporosis).

Examples of methods for identifying one or more suitable diagnostic spectral windows for a given condition, using, for example, pattern recognition methods, are described herein.

The term "diagnostic spectral window," as used herein, pertains to narrow range of chemical shift ($\Delta\delta$) values encompassing an index value, $\delta_r$ (that is, $\delta_r$ falls within the range $\Delta\delta$). Each index value, and its associated spectral window, define a range of chemical shift ($\Delta\delta$) in which the NMR spectral intensity is indicative of the presence of one or more chemical species.

For 2D NMR methods, the diagnostic spectral window refers to a chemical shift patch ($\Delta\delta_1$, $\Delta\delta_2$) which encompasses an index value, $[\delta_{r1}, \delta_{r2}]$. For 3D NMR methods, the diagnostic spectral window refers to a chemical shift volume ($\Delta\delta_1$, $\Delta\delta_2$, $\Delta\delta_3$) which encompasses an index value, [$\delta_{r1}$, $\delta_{r2}$, $\delta_{r3}$].

In one embodiment, the spectral window is centred with respect to its index value (e.g., $\delta_r=1.30$; $|\Delta\delta|=\delta\ 0.04$, and $\Delta\delta$ 1.28–1.32).

The breadth of the range, $|\Delta\delta|$, is determined largely by the spectroscopic parameters, such as field strength/frequency, temperature, sample viscosity, etc. The breadth of the range is often chosen to encompass a typical spin-coupled multiplet pattern. For peaks whose position varies with sample pH, the breadth of the range is may be widened to encompass the expected range of positions.

Typically, the breadth of the range, $|\Delta\delta|$, is from about $\delta$ 0.001 to about $\delta$ 0.2.

In one embodiment, the breadth is from about $\delta$ 0.005 to about $\delta$ 0.1.

In one embodiment, the breadth is from about $\delta$ 0.005 to about $\delta$ 0.08.

In one embodiment, the breadth is from about $\delta$ 0.01 to about $\delta$ 0.08.

In one embodiment, the breadth is from about $\delta$ 0.02 to about $\delta$ 0.08.

In one embodiment, the breadth is from about $\delta$ 0.005 to about $\delta$ 0.06.

In one embodiment, the breadth is from about $\delta$ 0.01 to about $\delta$ 0.06.

In one embodiment, the breadth is from about $\delta$ 0.02 to about $\delta$ 0.06.

In one embodiment, the breadth is about $\delta$ 0.04.

In one embodiment, the breadth is equal to the "bucket" or "bin" width. In one embodiment, the breadth is equal to an integer multiple of the "bucket" or "bin" width.

Although the diagnostic spectral windows are determined in relation to the condition under study, the precise index values for such windows may vary in accordance with the experimental parameters employed, for example, the digital resolution in the original spectra, the width of the buckets used, the temperature of the spectral data acquisition, etc. The exact composition of the sample (e.g., biofluid, tissue, etc.) can affect peak positions by compartmentation, metal complexation, protein-small molecule binding, etc. The observation frequency will have an effect because of different degrees of peak overlap and of first/second order nature of spectra.

In one embodiment, said one or more predetermined diagnostic spectral windows is: a single predetermined diagnostic spectral window.

In one embodiment, said one or more predetermined diagnostic spectral windows is: a plurality of predetermined diagnostic spectral windows. In practice, this may be preferred.

Although the theoretical limit on the number of predetermined diagnostic spectral windows is a function of the data density (e.g., the number of variables, e.g., buckets), typically the number of predetermined diagnostic spectral windows is from 1 to about 30. It is possible for the actual number to be in any sub-range within these general limits. Examples of lower limits include 1, 2, 3, 4, 5, 6, 8, 10, and 15. Examples of upper limits include 3, 4, 5, 6, 8, 10, 15, 20, 25, and 30.

In one embodiment, the number is from 1 to about 20.
In one embodiment, the number is from 1 to about 15.
In one embodiment, the number is from 1 to about 10.
In one embodiment, the number is from 1 to about 8.
In one embodiment, the number is from 1 to about 6.
In one embodiment, the number is from 1 to about 5.
In one embodiment, the number is from 1 to about 4.
In one embodiment, the number is from 1 to about 3.
In one embodiment, the number is 1 or 2.

In one embodiment, said one or more predetermined diagnostic spectral windows is: a plurality of diagnostic spectral windows; and, said NMR spectral intensity at one or more predetermined diagnostic spectral windows is: a combination of a plurality of NMR spectral intensities, each of which is NMR spectral intensity for one of said plurality of predetermined diagnostic spectral windows.

In one embodiment, said combination is a linear combination.

In one embodiment, at least one of said one or more predetermined diagnostic spectral windows encompasses a chemical shift value for an NMR resonance of free proline (e.g., a $^1$H NMR resonance of free proline).

In one embodiment, each of a plurality of said one or more predetermined diagnostic spectral windows encompasses a chemical shift value for an NMR resonance of free proline (e.g., a $^1$H NMR resonance of free proline).

In one embodiment, each of said one or more predetermined diagnostic spectral windows encompasses a chemical shift value for an NMR resonance of free proline (e.g., a $^1$H NMR resonance of free proline).

The $^1$H NMR chemical shifts for free proline in acid, neutral, and basic aqueous solution, are shown below. Note that each proton of the $CH_2$ groups should have a distinct $^1$H NMR chemical shift, because of the presence of the chiral centre. These are resolved for the β- and δ-$CH_2$ groups (i.e., β-$CH_2$ and β'-$CH_2$; δ-$CH_2$ and δ'-$CH_2$); but not for the γ-$CH_2$ group. See, for example, Fan, 1996.

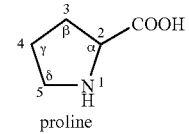

$^1$H NMR Chemical Shifts for Free Proline proline

| Proton | δH (acid) | δH (neutral) | δH (basic) | Multiplicity |
|---|---|---|---|---|
| α-CH | 4.45 | 4.14 | 3.46 | triplet |
| β-$CH_2$ | 2.41 | 2.36 | 2.12 | multiplet |
| β'-$CH_2$ | 2.17 | 2.08 | 1.72 | multiplet |
| γ-$CH_2$ | 2.06 | 2.01 | 1.72 | multiplet |
| δ-$CH_2$ | 3.42 | 3.40 | 2.74 | triplet |
| δ'-$CH_2$ | 3.42 | 3.33 | 3.02 | triplet |

Samples

The methods of the present invention are applied to spectra obtained or recorded for particular samples under study ("study samples"). Samples may be in any form which is compatible with the particular type of spectroscopy, and therefore may be, as appropriate, homogeneous or heterogeneous, comprising one or a combination of, for example, a gas, a liquid, a liquid crystal, a gel, and a solid.

Samples which originate from an organism (e.g., subject, patient) may be in vivo; that is, not removed from or separated from the organism. Thus, in one embodiment, said sample is an in vivo sample. For example, the sample may be circulating blood, which is "probed" in situ, in vivo, for example, using NMR methods.

Samples which originate from an organism may be ex vivo; that is, removed from or separated from the organism (e.g., an ex vivo blood sample, an ex vivo urine sample). Thus, in one embodiment, said sample is an ex vivo sample.

In one embodiment, said sample is an ex vivo blood or blood-derived sample.

In one embodiment, said sample is an ex vivo blood sample.

In one embodiment, said sample is an ex vivo plasma sample.

In one embodiment, said sample is an ex vivo serum sample.

In one embodiment, said sample is an ex vivo urine sample.

In one embodiment, said sample is removed from or separated from an/said organism, and is not returned to said organism (e.g., an ex vivo blood sample, an ex vivo urine sample).

In one embodiment, said sample is removed from or separated from an/said organism, and is returned to said organism (i.e., "in transit") (e.g., as with dialysis methods). Thus, in one embodiment, said sample is an ex vivo in transit sample.

Examples of samples include:
- a whole organism (living or dead, e.g., a living human);
- a part or parts of an organism (e.g., a tissue sample, an organ);
- a pathological tissue such as a tumour;
- a tissue homogenate (e.g. a liver microsome fraction);
- an extract prepared from a organism or a part of an organism (e.g., a tissue sample extract, such as perchloric acid extract);
- an infusion prepared from a organism or a part of an organism (e.g., tea, Chinese traditional herbal medicines);
- an in vitro tissue such as a spheroid;
- a suspension of a particular cell type (e.g. hepatocytes);
- an excretion, secretion, or emission from an organism (especially a fluid);
- material which is administered and collected (e.g., dialysis fluid);
- material which develops as a function of pathology (e.g., a cyst, blisters); and,
- supernatant from a cell culture.

Examples of fluid samples include, for example, blood plasma, blood serum, whole blood, urine, (gall bladder) bile, cerebrospinal fluid, milk, saliva, mucus, sweat, gastric juice, pancreatic juice, seminal fluid, prostatic fluid, seminal vesicle fluid, seminal plasma, amniotic fluid, foetal fluid, follicular fluid, synovial fluid, aqueous humour, ascite fluid, cystic fluid, blister fluid, and cell suspensions; and extracts thereof.

Examples of tissue samples include liver, kidney, prostate, brain, gut, blood, blood cells, skeletal muscle, heart muscle, lymphoid, bone, cartilage, and reproductive tissues.

Blood, Plasma, Serum

Blood is the fluid that circulates in the blood vessels of an animal (e.g., mammal) body, that is, the fluid that is circulated through the heart, arteries, veins, and capillaries. The function of the blood and the circulation is to service the needs of other tissues: to transport oxygen and nutrients to the tissues, to transport carbon dioxide and various metabolic waste products away, to conduct hormones from one part of the body to another, and in general to maintain an appropriate environment in all tissue fluids for optimal survival and function of the cells.

Blood consists of a liquid component, plasma, and a solid component, cells and formed elements (e.g., erythrocytes, leukocytes, and platelets), suspended within it. Erythrocytes, or red blood cells account for about 99.9% of the cells suspended in human blood. They contain haemoglobin which is involved in the transport of oxygen and carbon dioxide. Leukocytes, or white blood cells, account for about 0.1% of the cells suspended in human blood. They play a role in the body's defence mechanism and repair mechanism, and may be classified as agranular or granular. Agranular leukocytes include monocytes and small, medium and large lymphocytes, with small lymphocytes accounting for about 20-25% of the leukocytes in human blood. T cells and B cells are important examples of lymphocytes. Three classes of granular leukocytes are known, neutrophils, eosinophils, and basophils, with neutrophils accounting for about 60% of the leukocytes in human blood. Platelets (i.e., thrombocytes) are not cells but small spindle-shaped or rodlike bodies about 3 microns in length which occur in large numbers in circulating blood. Platelets play a major role in clot formation.

Plasma is the liquid component of blood. It serves as the primary medium for the transport of materials among cellular, tissue, and organ systems and their various external environments, and it is essential for the maintenance of normal haemostasis. One of the most important functions of many of the major tissue and organ systems is to maintain specific components of plasma within acceptable physiological limits. Plasma is the residual fluid of blood which remains after removal of suspended cells and formed elements. Whole blood is typically processed to removed suspended cells and formed elements (e.g., by centrifugation) to yield blood plasma. Serum is the fluid which is obtained after blood has been allowed to dot and the clot removed. Blood serum may be obtained by forming a blood clot (e.g., optionally initiated by the addition of thrombin and calcium ion) and subsequently removing the clot (e.g., by centrifugation). Serum and plasma differ primarily in their content of fibrinogen and several components which are removed in the clotting process. Plasma may be effectively prevented from clotting by the addition of an anti-coagulant (e.g., sodium citrate, heparin, lithium heparin) to permit handling or storage. Plasma is composed primarily of water (approximately 90%), with approximately 7% proteins, 0.9% inorganic salts, and smaller amounts of carbohydrates, lipids, and organic salts.

The term "blood sample," as used herein, pertains to a sample of whole blood.

The term "blood-derived sample," as used herein, pertains to an ex vivo sample derived from the blood of the subject under study.

Examples of blood and blood-derived samples include, but are not limited to, whole blood (WB), blood plasma (including, e.g., fresh frozen plasma (FFP)), blood serum, blood fractions, plasma fractions, serum fractions, blood fractions comprising red blood cells (RBC), platelets (PLT), leukocytes, etc., and cell lysates including fractions thereof (for example, cells, such as red blood cells, white blood cells, etc., may be harvested and lysed to obtain a cell lysate).

Methods for obtaining, preparing, handling, and storing blood and blood-derived samples (e.g., plasma, serum) are well known in the art. See, for example, Lindon et al., 1999. Typically, blood is collected from subjects using conventional techniques (e.g., from the ante-cubital fossa), typically preprandially.

For use in the methods described herein, the method used to prepare the blood fraction (e.g., serum) should be reproduced as carefully as possible from one subject to the next. It is important that the same or similar procedure be used for all subjects. It may be preferable to prepare serum (as opposed to plasma or other blood fractions) for two reasons: (a) the preparation of serum is more reproducible from individual to individual than the preparation of plasma, and (b) the preparation of plasma requires the addition of anticoagulants (e.g., EDTA, citrate, or heparin) which will be visible in the NMR metabonomic profile and may reduce the data density available.

A typical method for the preparation of serum suitable for analysis by the methods described herein is as follows: 10 mL of blood is drawn from the antecubital fossa of an individual who had fasted overnight, using an 18 gauge butterfly needle.

The blood is immediately dispensed into a polypropylene tube and allowed to clot at room temperature for 3 hours. The clotted blood is then subjected to centrifugation (e.g., 4,500×g for 5 minutes) and the serum supernatant removed to a clean tube. If necessary, the centrifugation step can be repeated to ensure the serum is efficiently separated from the clot. The serum supernatant may be analysed "fresh" or it may be stored frozen for later analysis.

A typical method for the preparation of plasma suitable for analysis by the methods described herein is as follows: High quality platelet-poor plasma is made by drawing the blood using a 19 gauge butterfly needle without the use of a tourniquet from the anetcubital fossa. The first 2 mL of blood drawn is discarded and the remainder is rapidly mixed and aliquoted into Diatube H anticoagulant tubes (Becton Dickinson). After gentle mixing by inversion the anticoagulated blood is cooled on ice for 15 minutes then subjected to centrifugation to pellet the cells and platelets (approximately 1,200×g for 15 minutes). The platelet poor plasma supernantant is carefully removed, drawing off the middle third of the supernatant and discarding the upper third (which may contain floating platelets) and the lower third which is too close to the readily disturbed platelet layer on the top of the cell pellet. The plasma may then be aliquoted and stored frozen at −20° C. or colder, and then thawed when required for assay.

Samples may be analysed immediately ("fresh"), or may be frozen and stored (e.g., at −80° C.) ("fresh frozen") for future analysis. If frozen, samples are completely thawed prior to analysis.

In one embodiment, said sample is a blood sample or a blood-derived sample.

In one embodiment, said sample is a blood sample.

In one embodiment, said sample is a blood plasma sample.

In one embodiment, said sample is a blood serum sample.

Urine

The composition of urine is complex and highly variable both between species and within species according to lifestyle. A wide range of organic acids and bases, simple sugars and polysaccharides, heterocycles, polyols, low molecular weight proteins and polypeptides are present together with inorganic species such as $Na^+$, $K^+$, $Ca^{2+}$, $Mg^{2+}$, $HCO_3^-$, $SO_4^{2-}$ and phosphates.

The term "urine," as used herein, pertains to whole (or intact) urine.

The term "urine-derived sample," as used herein, pertains to an ex vivo sample derived from the urine of the subject under study (e.g., obtained by dilution, concentration, addition of additives, solvent- or solid-phase extraction, etc.). Analysis may be performed using, for example, fresh urine; urine which has been frozen and then thawed; urine which has been dried (e.g., freeze-dried) and then reconstituted, e.g., with water or $D_2O$.

Methods for the collection (e.g., by excretion, catheterisation, etc.), handling, storage, and pre-analysis preparation of many classes of sample, especially biological samples (e.g., biofluids) are well known in the art. See, for example, Lindon et al., 1999.

Again, samples may be analysed immediately ("fresh"), or may be frozen and stored (e.g., at −80° C.) ("fresh frozen") for future analysis. If frozen, samples are completely thawed prior to analysis.

In one embodiment, said sample is a urine sample or a urine-derived sample.

In one embodiment, said sample is a urine sample.

A: Spectral Analysis Methods

As discussed above, many of the methods of the present invention involve NMR spectral intensity at one or more predetermined diagnostic spectral windows. Some suitable methods for determining NMR spectral intensity and diagnostic spectral windows are described below.

Also, as discussed above, many of the methods of the present invention involve use of a predictive mathematical model. Some suitable methods for forming and using such models are described below.

A new "metabonomic" approach has been developed which is aimed at augmenting and complementing the information provided by genomics and proteomics. "Metabonomics" is conventionally defined as "the quantitative measurement of the multiparametric metabolic response of living systems to pathophysiological stimuli or genetic modification" (see, for example, Nicholson et al., 1999). This concept has arisen primarily from the application of $^1H$ NMR spectroscopy to study the metabolic composition of biofluids, cells, and tissues and from studies utilising pattern recognition (PR), expert systems and other chemoinformatic tools to interpret and classify complex NMR-generated metabolic data sets. Metabonomic methods have the potential, ultimately, to determine the entire dynamic metabolic make-up of an organism. The NMR spectrum of a sample (e.g., biofluid) provides a metabolic fingerprint or profile of the organism from which the sample was obtained, and this metabolic fingerprint or profile is characteristically changed by a disease, toxic process, genetic modification, etc.

NMR Spectroscopy

As discussed above, many aspects of the present invention pertain to methods which employ NMR spectra, or data obtained or derived from NMR spectra (e.g., NMR spectral data).

The principal nucleus studied in biomedical NMR spectroscopy is the proton or $^1H$ nucleus. This is the most sensitive of all naturally occurring nuclei. The chemical shift range is about 10 ppm for organic molecules. In addition $^{13}C$ NMR spectroscopy using either the naturally abundant 1.1% $^{13}C$ nuclei or employing isotopic enrichment is useful for identifying metabolites. The $^{13}C$ chemical shift range is about 200 ppm. Other nuclei find special application. These include 15N (in natural abundance or enriched), $^{19}F$ for studies of drug metabolism, and $^{31}P$ for studies of endogenous phosphate biochemistry either in vitro or in vivo.

In order to obtain an NMR spectrum, it is necessary to define a "pulse program". At its simplest, this is application of a radio-frequency (RF) pulse followed by acquisition of a free induction decay (FID)—a time-dependent oscillating, decaying voltage which is digitised in an analog-digital converter (ADC). At equilibrium, the nuclear spins are present in a number of quantum states and the RF pulse disturbs this equilibrium. The FID is the result of the spins returning towards the equilibrium state. It is necessary to choose the length of the pulse (usually a few microseconds) to give the optimum response.

This, and other experimental parameters are chosen on the basis of knowledge and experience on the part of the spectroscopist. See, for example, T. D. W. Claridge, *High-Resolution NMR Techniques in Organic Chemistry: A Practical Guide to Modern NMR for Chemists*, Oxford University Press, 2000. These are based on the observation frequency to be used, the known properties of the nucleus under study (i.e., the expected chemical shift range will determine the spectral width, the desired peak resolution determines the number of data points, the relaxation times determine the recycle time between scans, etc.). The number of scans to be added is determined by the concentration of the analyte, the inherent sensitivity of the nucleus under study and its abundance (either natural or enhanced by isotopic enrichment).

After data acquisition, a number of possible manipulations are possible. The FID can be multiplied by a mathematical function to improve the signal-to-noise ratio or reduce the peak line widths. The expert operator has choice over such parameters. The FID is then often filled by a number of zeros and then subjected to Fourier transformation. After this conversion from time-dependent data to frequency dependent data, it is necessary to phase the spectrum so that all peaks appear upright—this is done using two parameters by visual inspection on screen (now automatic routines are available with reasonable success). At this point the spectrum baseline can be curved. To remedy this, one defines points in the spectrum where no peaks appear and these are taken to be baseline. Usually, a polynomial function is fitted to these points, but other methods are available, and this function subtracted from the spectrum to provide a flat baseline. This can also be done in an automatic fashion. Other manipulations are also possible. It is possible to extend the FID forwards or backwards by "linear prediction" to improve resolution or to remove so-called truncation artefacts which occur if data acquisition of a scan is stopped before the FID has decayed into the noise. All of these decisions are also applicable to 2- and 3-dimensional NMR spectroscopy.

An NMR spectrum consists of a series of digital data points with a y value (relating to signal strength) as a function of equally spaced x-values (frequency). These data point values run over the whole of the spectrum. Individual peaks in the spectrum are identified by the spectroscopist or automatically by software and the area under each peak is determined either by integration (summation of the y values of all points over the peak) or by curve fitting. A peak can be a single resonance or a multiplet of resonances corresponding to a single type of nucleus in a particular chemical environment (e.g., the two protons ortho to the carboxyl group in benzoic acid). Integration is also possible of the three dimensional peak volumes in 2-dimensional NMR spectra. The intensity of a peak in an NMR spectrum is proportional to the number of nuclei giving rise to that peak (if the experiment is conducted under conditions where each successive accumulated free induction decay (FID) is taken starting at equilibrium). Also, the relative intensity of peaks from different analytes in the same sample is proportional to the concentration of that analyte (again if equilibrium prevails at the start of each scan).

Thus, the term "NMR spectral intensity," as used herein, pertains to some measure related to the NMR peak area, and may be absolute or relative. NMR spectral intensity may be, for example, a combination of a plurality of NMR spectral intensities, e.g., a linear combination of a plurality of NMR spectral intensities.

In the context of NMR spectral intensity, the term "NMR" refers to any type of NMR spectroscopy.

NMR spectroscopic techniques can be classified according to the number of frequency axes and these include 1 D-, 2D-, and 3D-NMR. ID spectra include, for example, single pulse; water-peak eliminated either by saturation or non-excitation; spin-echo, such as CPMG (i.e., edited on the basis of spin-spin relaxation); diffusion-edited, selective excitation of specific spectra regions. 2D spectra include for example J-resolved (JRES); 1H-1H correlation methods, such as NOESY, COSY, TOCSY and variants thereof; heteronuclear correlation including direct detection methods, such as HETCOR, and inverse-detected methods, such as 1H-13C HMQC, HSQC, HMBC. 3D spectra include many variants, all of which are combinations of 2D methods, e.g. HMQC-TOCSY, NOESY-TOCSY, etc. All of these NMR spectroscopic techniques can also be combined with magic-angle-spinning (MAS) in order to study samples other than isotropic liquids, such as tissues, which are characterised by anisotropic composition.

Preferred nuclei include $^1$H and $^{13}$C. Preferred techniques for use in the present invention include water-peak eliminated, spin-echo such as CPMG, diffusion edited, JRES, COSY, TOCSY, HMQC, HSQC, and HMBC.

NMR analysis (especially of biofluids) is carried out at as high a field strength as is practical, according to availability (very high field machines are not widespread), cost (a 600 MHz instrument costs about £500,000 but a shielded 800 MHz instrument can cost more than £3,500,000, depending on the nature of accessory equipment purchased), and ability to accommodate the physical size of the instrument. Maintenance/operational costs do not vary greatly and are small compared to the capital cost of the machine and the personnel costs.

Typically, the $^1$H observation frequency is from about 200 MHz to about 900 MHz, more typically from about 400 MHz to about 900 MHz, yet more typically from about 500 MHz to about 750 MHz. $^1$H observation frequencies of 500 and 600 MHz may be particularly preferred. Instruments with the following $^1$H observation frequencies are/were commercially available: 200, 250, 270 (discontinued), 300, 360 (discontinued), 400, 500, 600, 700, 750, 800, and 900 MHz.

Higher frequencies are used to obtain better signal-to-noise ratio and for greater spectral dispersion of resonances. This gives a better chance of identifying the molecules giving rise to the peaks. The benefit is not linear because in addition to the better dispersion, the detailed spectral peaks can move from being "second-order"—where analysis by inspection is not possible, towards "first-order," where it is. Both peak positions and intensities within multiplets change in a non-linear fashion as this progression occurs. Lower observation frequencies would be used where cost is an issue, but this is likely to lead to reduced effectiveness for classification and identification of biomarkers.

NMR Spectroscopy: Sample Preparation

NMR spectra can be measured in solid, liquid, liquid crystal or gas states over a range of temperatures from 120 K to 420 K and outside this range with specialised equipment. Typically, NMR analysis of biofluids is performed in the liquid state with a sample temperature of from about 274 K to about 328 K, but more typically from about 283 K to about 321 K. An example of a typical temperature is about 300 K.

Lower temperatures would be used to ensure that the biofluid did not suffer from any decomposition or show any effects of chemical or enzymatic reactions during the data acquisition. Higher temperatures may be used to improve detection of certain species. For example, for plasma or serum, lipoproteins undergo a series of phase changes as the temperature is increased; in particular, the low density lipoprotein (LDL) peak intensities are rather temperature dependent and the lines sharpen and broader more-difficult-to-detect components become visible as the lipoprotein becomes more "liquid."

Typically, biofluid samples are diluted with solvent prior to NMR analysis. This is done for a variety of reasons, including: to lessen solution viscosity, to control the pH of the solution, and to allow addition of reagents and reference materials.

An example of a typical dilution solvent is a solution of 0.9% by weight of sodium chloride in $D_2O$. The $D_2O$ lessens the overall concentration of $H_2O$ and eases the technical requirements in the suppression of the solvent water NMR resonance, necessary for optimum detection of metabolite NMR signals. The deuterium nuclei of the $D_2O$ also provides an NMR signal for locking the magnetic field enabling the exact co-registration of successive scans.

Depending on the available amount of the biofluid, typically, the dilution ratio is from about 1:50 to about 5:1 by volume, but more typically from about 1:20 to about 1:1 by volume. An example of a typical dilution ratio is 3:7 by volume (e.g., 150 µL sample, 350 µL solvent), typical for conventional 5 mm NMR tubes and for flow-injection NMR spectroscopy.

Typical sample volumes for NMR analysis are from about 50 µL (e.g., for microprobes) to about 2 mL. An example of a typical sample volume is about 500 µL.

NMR peak positions (chemical shifts) are measured relative to that of a known standard compound usually added directly to the sample. For biofluids such as urine this is commonly a partially deuterated form of TSP, i.e., 3-trimethylsilyl-[2,2,3,3-$^2H_4$]-propionate sodium salt. For biofluids containing high levels of proteins, this substance is not suitable since it binds to proteins and shows a broadened NMR line. Added formate anion (e.g., as a salt) can be used in such cases as for blood plasma.

NMR Spectroscopy: Manipulation of NMR Spectra

NMR spectra are typically acquired, and subsequently, handled in digitised form. Conventional methods of spectral pre-processing of (digital) spectra are well known, and include, where applicable, signal averaging, Fourier transformation (and other transformation methods), phase correction, baseline correction, smoothing, and the like (see, for example, Lindon et al., 1980).

Modern spectroscopic methods often permit the collection of high or very high resolution spectra. In digital form, even a simple spectrum (e.g., signal versus spectroscopic parameter) may have many thousands, if not tens of thousands of data points. It is often desirable to reduce or compress the data to give fewer data points, for both practical computing methods and also to effect some degree of signal averaging to compensate for physical effects, such as pH variation, compartmentalisation, and the like. The resulting data may be referred to as "spectral data."

For example, a typical $^1H$ NMR spectrum is recorded as signal intensity versus chemical shift ($\delta$) which ranges from about $\delta$ 0 to $\delta$ 10. At a typical chemical shift resolution of about $\delta$ $10^{-4}$-$10^{-3}$ ppm, the spectrum in digital form comprises about 10,000 to 100,000 data points. As discussed above, it is often desirable to compress this data, for example, by a factor of about 10 to 100, to about 1000 data points.

For example, in one approach, the chemical shift axis, $\delta$, is "segmented" into "buckets" or "bins" of a specific length. For a 1-D $^1H$ NMR spectrum which spans the range from $\delta$ 0 to $\delta$ 10, using a bucket length, $\Delta\delta$, of 0.04 yields 250 buckets, for example, $\delta$ 10.0-9.96, $\delta$ 9.96-9.92, $\delta$ 9.92-9.88, etc., usually reported by their midpoint, for example, $\delta$ 9.98, $\delta$ 9.94, $\delta$ 9.90, etc. The signal intensity within a given bucket may be averaged or integrated, and the resulting value reported. In this way, a spectrum with, for example, 100,000 original data points can be compressed to an equivalent spectrum with, for example, 250 data points.

A similar approach can be applied to 2-D spectra, 3-D spectra, and the like. For 2-D spectra, the "bucket" approach may be extended to a "patch." For 3-D spectra, the "bucket" approach may be extended to a "volume." For example, a 2-D $^1H$ NMR spectrum which spans the range from $\delta$ 0 to $\delta$ 10 on both axes, using a patch of $\Delta\delta$ 0.1×$\Delta\delta$ 0.1 yields 10,000 patches. In this way, a spectrum with perhaps $10^8$ original data points can be compressed to an equivalent spectrum of $10^4$ data points.

In this context, the equivalent spectrum may be referred to as "a spectral data set," "a data set comprising spectral data," etc.

Software for such processing of NMR spectra, for example AMIX (Analysis of MIXture, V 2.5, Bruker Analytik, Rheinstetten, Germany) is commercially available.

Often, certain spectral regions carry no real diagnostic information, or carry conflicting biochemical information, and it is often useful to remove these "redundant" regions before performing detailed analysis. In the simplest approach, the data points are deleted. In another simple approach, the data in the redundant regions are replaced with zero values.

For example, due to the dynamic range problem with water in comparison with other molecules, the water resonance (around $\delta$ 4.7) is suppressed. However, small variations in water suppression remain, and these variations can undesirably complicate analysis. Similarly, variations in water suppression may also affect the urea signal (around $\delta$ 6.0), by cross saturation. Therefore, it is often useful to delete certain spectral regions, for example, from about $\delta$ 4.5 to 6.0 (e.g., $\delta$ 4.52 to 6.00).

In general, NMR data is handled as a data matrix. Typically, each row in the matrix corresponds to an individual sample (often referred to as a "data vector"), and the entries in the columns are, for example, spectral intensity of a particular data point, at a particular $\delta$ or $\Delta\delta$ (often referred to as "descriptors").

It is often useful to pre-process data, for example, by addressing missing data, translation, scaling, weighting, etc.

Multivariate projection methods, such as principal component analysis (PCA) and partial least squares analysis (PLS), are so-called scaling sensitive methods. By using prior knowledge and experience about the type of data studied, the quality of the data prior to multivariate modelling can be enhanced by scaling and/or weighting. Adequate scaling and/or weighting can reveal the important and interesting variation hidden within in the data, and therefore make subsequent multivariate modelling more efficient. Scaling and weighting may be used to place the data in the correct metric, based on knowledge and experience of the studied system, and therefore reveal patterns already inherently present in the data.

If at all possible, missing data, for example, gaps in column values, should be avoided. However, if necessary, such missing data may replaced or "filled" with, for example, the mean value of a column ("mean fill"); a random value ("random fill"); or a value based on a principal component analysis ("principal component fill"). Each of these different approaches will have a different effect on subsequent PR analysis.

"Translation" of the descriptor coordinate axes can be useful. Examples of such translation include normalisation and mean centring.

"Normalisation" may be used to remove sample-to-sample variation. Many normalisation approaches are possible, and they can often be applied at any of several points in the analysis. Usually, normalisation is applied after redundant spectral regions have been removed. In one approach, each spectrum is normalised (scaled) by a factor of 1/A, where A is the sum of the absolute values of all of the descriptors for that spectrum. In this way, each data vector has the same length, specifically, 1. For example, if the sum of the absolute values of intensities for each bucket in a particular spectrum is 1067, then the intensity for each bucket for this particular spectrum is scaled by $1/1067$.

"Mean centring" may be used to simplify interpretation. Usually, for each descriptor, the average value of that descriptor for all samples is subtracted. In this way, the mean of a descriptor coincides with the origin, and all descriptors are "centred" at zero. For example, if the average intensity at δ 10.0-9.96, for all spectra, is 1.2 units, then the intensity at δ 10.0-9.96, for all spectra, is reduced by 1.2 units.

In "unit variance scaling," data can be scaled to equal variance. Usually, the value of each descriptor is scaled by 1/StDev, where StDev is the standard deviation for that descriptor for all samples. For example, if the standard deviation at δ 10.0-9.96, for all spectra, is 2.5 units, then the intensity at δ 10.0-9.96, for all spectra, is scaled by ½.₅ or 0.4. Unit variance scaling may be used to reduce the impact of "noisy" data. For example, some metabolites in biofluids show a strong degree of physiological variation (e.g., diurnal variation, dietary-related variation) that is unrelated to any pathophysiological process. Without unit variance scaling, these noisy metabolites may dominate subsequent analysis.

"Pareto scaling" is, in some sense, intermediate between mean centering and unit variance scaling. In effect, smaller peaks in the spectra can influence the model to a higher degree than for the mean centered case. Also, the loadings are, in general, more interpretable than for unit variance based models. In pareto scaling, the value of each descriptor is scaled by 1/sqrt(StDev), where StDev is the standard deviation for that descriptor for all samples. In this way, each descriptor has a variance numerically equal to its initial standard deviation. The pareto scaling may be performed, for example, on raw data or mean centered data.

"Logarithmic scaling" may be used to assist interpretation when data have a positive skew and/or when data spans a large range, e.g., several orders of magnitude. Usually, for each descriptor, the value is replaced by the logarithm of that value. For example, the intensity at δ 10.0-9.96 is replaced the logarithm of the intensity at δ 10.0-9.96, for all spectra.

In "equal range scaling," each descriptor is divided by the range of that descriptor for all samples. In this way, all descriptors have the same range, that is, 1. For example, if, at δ 10.0-9.96, for all spectra, the largest value is 87 units and the smallest value is 1, then the range is 86 units, and the intensity at δ 10.0-9.96, for all spectra, is divided by 86 units. However, this method is sensitive to presence of outlier points.

In "autoscaling," each data vector is mean centred and unit variance scaled. This technique is a very useful because each descriptor is then weighted equally and, in the case of NMR descriptors, large and small peaks are treated with equal emphasis. This can be important for metabolites present at very low, but still detectable, levels.

Several supervised methods of scaling data are also known. Some of these can provide a measure of the ability of a parameter (e.g., a descriptor) to discriminate between classes, and can be used to improve classification by stretching a separation.

For example, in "variance weighting," the variance weight of a single parameter (e.g., a descriptor) is calculated as the ratio of the inter-class variances to the sum of the intra-class variances. A large value means that this variable is discriminating between the classes. For example, if the samples are known to fall into two classes (e.g., a training set), it is possible to examine the mean and variance of each descriptor. If a descriptor has very different mean values and a small variance, then it will be good at separating the classes.

"Feature weighting" is a more general description of variance weighting, where not only the mean and standard deviation of each descriptor is calculated, but other well known weighting factors, such as the Fisher weight, are used.

Multivariate Statistical Analysis

As discussed above, multivariate statistics analysis methods, including pattern recognition methods, are often the most convenient and efficient way to analyse complex data, such as NMR spectra.

For example, such analysis methods may be used to identify, for example diagnostic spectral windows and/or diagnostic species, for a particular condition under study.

Also, such analysis methods may be used to form a predictive model, and then use that model to classify test data. For example, one convenient and particularly effective method of classification employs multivariate statistical analysis modelling, first to form a model (a "predictive mathematical model") using data ("modelling data") from samples of known class (e.g., from subjects known to have, or not have, a particular condition), and second to classify an unknown sample (e.g., "test data"), as having, or not having, that condition.

Examples of pattern recognition methods include, but are not limited to, Principal Component Analysis (PCA) and Partial Least Squares-Discriminant Analysis (PLS-DA).

PCA is a bilinear decomposition method used for overviewing "clusters" within multivariate data. The data are represented in K-dimensional space (where K is equal to the number of variables) and reduced to a few principal components (or latent variables) which describe the maximum variation within the data, independent of any knowledge of class membership (i.e., "unsupervised"). The principal components are displayed as a set of "scores" (t) which highlight clustering, trends, or outliers, and a set of "loadings" (p) which highlight the influence of input variables on t. See, for example, B. R. Kowalski, M. Sharaf, and D. Illman, *Chemometrics* (John Wiley & Sons, Chichester, 1986).

The PCA decomposition can be described by the following equation:

$$X = TP' + E$$

where T is the set of scores explaining the systematic variation between the observations in X and P is the set of loadings explaining the between variable variation and provides the explanation to clusters, trends, and outliers in the score space. The non-systematic part of the variation not explained by the model forms the residuals, E.

PLS-DA is a supervised multivariate method yielding latent variables describing maximum separation between known classes of samples. PLS-DA is based on PLS which is the regression extension of the PCA method explained earlier. When PCA works to explain maximum variation between the studied samples PLS-DA suffices to explain maximum separation between known classes of samples in the data (X). This is done by a PLS regression against a "dummy vector or matrix" (Y) carrying the class separating information. The calculated PLS components will thereby be more focused on describing the variation separating the classes in X if this information is present in the data. From an interpretation point of view all the features of PLS can be used, which means that the variation can be interpreted in terms of scores (t,u), loadings (p,c), PLS weights (w) and regression coefficients (b). The fact that a regression is carried out against a known class separation means that the PLS-DA is a supervised method and that the class membership has to be known prior to the actual modelling. Once a model is calculated and validated it can be used for prediction of class membership for "new" unknown samples. Judgement of class membership is done on basis of predicted class membership (Ypred), predicted scores (tpred) and predicted residuals (DmodXpred)

using statistical significance limits for the decision. See, for example, Sjostrom et al., 1986; Stahle et al., 1987.

In PLS, the variation between the objects in X is described by the X-scores, T, and the variation in the Y-block regressed against is described in the Y-scores, U. In PLS-DA the Y-block is a "dummy vector or matrix" describing the class membership of each observation. Basically, what PLS does is to maximize the covariance between T and U. For each component, a PLS weight vector, w, is calculated, containing the influence of each X-variable on the explanation of the variation in Y. Together the weight vectors will form a matrix, W, containing the variation in X that maximizes the covariance between the scores T and U for each calculated component. For PLS-DA this means that the weights, W, contain the variation in X that is correlated to the class separation described in Y. The Y-block matrix of weights is designated C. A matrix of X-loadings, P, is also calculated. These loadings are apart from interpretation used to perform the proper decomposition of X.

The PLS decomposition of X and Y can hence be described as follows:

$$X = TP' + E$$

$$Y = TC' + F$$

The PLS regression coefficients, B, are then given by:

$$B = W(P'W)^{-1}C'$$

The estimate of Y, $Y_{hat}$, can then be calculated according to the following formula:

$$Y_{hat} = XW(P'W)^{-1}C' = XB$$

Both of the pattern recognition algorithms exemplified herein (PCA, PLS-DA) rely on extraction of linear associations between the input variables. When such linear relationships are insufficient, neural network-based pattern recognition techniques can in some cases improve the ability to classify individuals on the basis of the many inter-related input variables (see, e.g., Ala-Korpela et al., 1995; Hiltunen et al., 1995). Nevertheless, the methods applied herein are sufficiently powerful to allow classification of the individuals studied, and they provide an additional benefit over neural network methods in that they allow some information to be gained as to what aspects of the input dataset were particularly important in allowing classification to be made.

Spurious or irregular data in spectra ("outliers"), which are not representative, are preferably identified and removed. Common reasons for irregular data ("outliers") include spectral artefacts such as poor phase correction, poor baseline correction, poor chemical shift referencing, poor water suppression, and biological effects such as bacterial contamination, shifts in the pH of the biofluid, toxin- or disease-induced biochemical response, and other conditions, e.g., pathological conditions, which have metabolic consequences, e.g., diabetes.

Outliers are identified in different ways depending on the method of analysis used. For example, when using principal component analysis (PCA), small numbers of samples lying far from the rest of the replicate group can be identified by eye as outliers. A more objective means of identification for PCA is to use the Hotelling's T Test which is the multivariate version of the well known Student's T test used in univariate statistics. For any given sample, the T2 value can be calculated and this is compared with a standard value within which a chosen fraction (e.g., 95%) of the samples would normally lie. Samples with T2 values substantially outside this limit can then be flagged as outliers.

Also, when using more sophisticated supervised methods, such as SIMCA or PNNs, a similar method is used. A confidence level (e.g., 95%) is selected and the region of multivariate space corresponding to confidence values above this limit is determined. This region can be displayed graphically in several different ways (for example by plotting the critical T2 ellipse on a PCA scores plot). Any samples falling outside the high confidence region are flagged as potential outliers.

Confidence Limits for outlier detection are also calculated in the residual direction expressed as the distance to model in X (DModX).

Briefly, DModX is the perpendicular distance of an object to the principal component (or to the plane or hyper plane made up by two or more principal components). In the SIMCA software, DModX is calculated as:

$$D\,\text{Mod}\,X = v * \text{sqrt}(e^2/K - A)$$

wherein e is the residual for a single observation;
K is the number of original variables in the data set;
A is the number of principal components in the model;
v is a correction factor, based on the number of observations (N) and the number of principal components (A), and is slightly larger than one.

The outliers in this direction are not as severe as those occurring in the score direction but should always be carefully examined before making a decision whether to include them in the modelling or not. In general, all outliers are thoroughly investigated, for example, by examining the contributing loadings and distance to model (DModX) as well as visually inspecting the original NMR spectrum for deviating features, before removing them from the model. Outlier detection by automatic algorithm is a possibility using the features of scores and residual distance to model (DModX) described above.

When using PLS methods, the distance to the model in Y (DmodY) can also be calculated in the same way.

Data Filtering

Although pattern recognition methods may be applied to "unfiltered" data, it is often preferable to first filter data to removed irrelevant variation.

In one method, latent variables which are of no interest may be removed by "filtering."

Examples of filtering methods include the regression of descriptor variables against an index based on sample class to eliminate variables with low correlation to the predefined classes. Related methods include target rotation (see, e.g., Kvalheim et al., 1989) and PCT filtering (see, e.g., Sun, 1997). In these methods, the removed variation is not necessarily completely uncorrelated with sample class (i.e., orthogonal).

In another method, latent variables which are orthogonal to some variation or class index of interest are removed by "orthogonal filtering." Here, variation in the data which is not correlated to (i.e., is orthogonal to) the class separating variation of interest may be removed. Such methods are, in general, more efficient than non-orthogonal filtering methods.

Various orthogonal filtering methods have been described (see, e.g., Wold et al., 1998; Fearn, 2000; Anderson, 1999; Westerhuis et al., 2001; Wise et al., 2001).

One preferred orthogonal filtering method is conventionally referred to as Orthogonal Signal Correction (OSC), wherein latent variables orthogonal to the variation of interest are removed. See, for example, Wold et al., 1998.

The class identity is used as a response vector, Y, to describe the variation between the sample classes. The OSC method then locates the longest vector describing the variation between the samples which is not correlated with the Y-vector, and removes it from the data matrix. The resultant dataset has been filtered to allow pattern recognition focused on the variation correlated to features of interest within the sample population, rather than non-correlated, orthogonal variation.

OSC is a method for spectral filtering that solves the problem of unwanted systematic variation in the spectra by removing components, latent variables, orthogonal to the response calibrated against. In PLS, the weights, w, are calculated to maximise the covariance between X and Y. In OSC, in contrast, the weights, w, are calculated to minimize the covariance between X and Y, which is the same as calculating components as close to orthogonal to Y as possible. These components, orthogonal to Y, containing unwanted systematic variation are then subtracted from the spectral data, X, to produce a filtered predictor matrix describing the variation of interest. Briefly, OSC can be described as a bilinear decomposition of the spectral matrix, X, in a set of scores, $T^{}$, and a set of corresponding loadings, $P^{}$, containing varition orthogonal to the response, Y. The unexplained part or the residuals, E, is equal to the filtered X-matrix, $X_{osc}$, containing less unwanted variation. The decomposition is described by the following equation:

$$X = T^{}P^{\prime} + E$$

$$X_{osc} = E$$

The OSC procedure starts by calculation of the first latent variable or principal component describing the variation in the data, X. The calculation is done according to the NIPALS algorithm.

$$X = tp' + E$$

The first score vector, t, which is a summary of the between sample variation in X, is then orthogonalized against response (Y), giving the orthogonalized score vector $t^*$.

$$t^* = (I - Y(Y'Y)^{-1}Y')t$$

After orthogonalization, the PLS weights, w, are calculated with the aim of making $Xw = t^*$. By doing this, the weights, w, are set to minimize the covariance between X and Y. The weights, w, are given by:

$$w = x - t^*$$

An estimate of the orthogonal score $t^{**}$ is calculated from:

$$t^{**} = Xw$$

The estimate or updated score vector $t^{}$ is then again orthogonalized to Y, and the iteration proceeds until $t^{}$ has converged. This will ensure that $t^{}$ will converge towards the longest vector orthogonal to response Y, still giving a good description of the variation in X. The data, X, can then be described as the score, $t^{}$, orthogonal to Y, times the corresponding loading vector $p^{**}$, plus the unexplained part, the residual, E.

$$X = t^{}p^{\prime} + E$$

The residual, E, equals the filtered X, $X_{osc}$, after subtraction of the first component orthogonal to the response Y.

$$E = X - t^{}p^{\prime}$$

$$Xosc = E$$

If more than one component needs to be removed, the same procedure is repeated using the residual, E, as the starting data matrix, X.

New external data not present in the model calculation must be treated according to filtering of the modelling data. This is done by using the calculated weights, w, from the filtering to calculate a score vector, $t_{new}$, for the new data, $X_{new}$.

$$t_{new} = X_{new}W$$

By subtracting $t_{new}$ times the loading vector from the calibration, $p^{**}$, from the new external data, $X_{new}$, the residual, $E_{new}$, will be the resulting OSC filtered matrix for the new external data.

$$E_{new} = X_{new} - t_{new}p^{**\prime}$$

If PCA suggests separation between the classes under investigation, orthogonal signal correction (OSC) can be used to optimize the separation, thus improving the performance of subsequent multivariate pattern recognition analysis and enhancing the predictive power of the model. In the examples described herein, both PCA and PLS-DA analyses were improved by prior application of OSC.

An example of a typical OSC process includes the following steps:

(a) $^1$H NMR data are segmented using AMIX, normalised, and optionally scaled and/or mean centered. The default for orthogonal filtering of spectral data is to use only mean centered data, which means that the mean for each variable (spectral bucket) is subtracted from each single variable in the data matrix.

(b) a response vector (y) describing the class separating variation is created by assigning class membership to each sample.

(c) one latent variable orthogonal to the response vector (y) is removed according to the OSC algorithm.

(d) if desired, the removed orthogonal variation can be viewed and interpreted in terms of scores (T) and loadings (P).

(e) the filtered data matrix, which contains less variation not correlated to class separation, is next used for further multivariate modelling after optional scaling and/or mean centering.

Any particular model is only as good as the data used to formulate it. Therefore, it is preferable that all modelling data and test data are obtained under the same (or similar) conditions and using the same (or similar) experimental parameters. Such conditions and parameters include, for example, sample type (e.g., plasma, serum), sample collection and handling protocol, sample dilution, NMR analysis (e.g., type, field strength/frequency, temperature), and data-processing (e.g., referencing, baseline correction, normalisation). If appropriate, it may be desirable to formulate models for a particular sub-group of cases, e.g., according to any of the parameters mentioned above (e.g., field strength/frequency), or others, such as sex, age, ethnicity, medical history, lifestyle (e.g., smoker, nonsmoker), hormonal status (e.g., pre-menopausal, post-menopausal).

In general, the quality of the model improves as the amount of modelling data increases. Nonetheless, as shown in the examples below, even relatively small sets of modelling data (e.g., about 50-100 subjects) is sufficient to achieve a confident classification (e.g., diagnosis).

A typical unsupervised modelling process includes the following steps:

(a) optionally scaling and/or mean centering modelling data;

(b) classifying data (e.g., as control or positive, e.g., diseased);

(c) fitting the model (e.g., using PCA, PLS-DA);

(d) identifying and removing outliers, if any;

(e) re-fitting the model;

(f) optionally repeating (c), (d), and (e) as necessary.

Optionally (and preferably), data filtering is performed following step (d) and before step (e). Optionally (and preferably), orthogonal filtering (e.g., OSC) is performed following step (d) and before step (e).

An example of a typical PLS-DA modelling process, using OSC filtered data, includes the following steps:
  (a) OSC filtered data is optionally scaled and/or mean centered.
  (b) a response vector (y) describing the class separating variation is created by assigning class membership to all samples.
  (c) a PLS regression model is calculated between the OSC filtered data and the response vector (y). The calculated latent variables or PLS components will be focused on describing maximum separation between the known classes.
  (d) the model is interpreted by viewing scores (T), loadings (P), PLS weights (W), PLS coefficients (B) and residuals (E). Together they will function as a means for describing the separation between the classes as well as provide an explanation to the observed separation.

Once the model has been calculated, it may be verified using data for samples of known class which were not used to calculate the model. In this way, the ability of the model to accurately predict classes may be tested. This may be achieved, for example, in the method above, with the following additional step:
  (e) a set of external samples, with known class belonging, which were not used in the (e.g., PLS) model calculation is used for validation of the model's predictive ability. The prediction results are investigated, fore example, in terms of predicted response ($y_{pred}$), predicted scores ($T_{pred}$), and predicted residuals described as predicted distance to model ($DmodX_{pred}$).

The model may then be used to classify test data, of unknown class. Before classification, the test data are numerically pre-processed in the same manner as the modelling data.

Interpreting the output from the pattern recognition (PR) analysis provides useful information on the biomarkers responsible for the separation of the biological classes. Of course, the PR output differs somewhat depending on the data analysis method used. As mentioned above, methods for PR and interpretation of the results are known in the art. Interpretation methods for two PR techniques (PCA and PLS-DA) are discussed briefly herein.

Interpreting PCA Results

The data matrix (X) is built up by N observations (samples, rats, patients, etc.) and K variables (spectral buckets carrying the biomarker information in terms of $^1$H-NMR resonances).

In PCA, the N*K matrix (X) is decomposed into a few latent variables or principal components (PCs) describing the systematic variation in the data. Since PCA is a bilinear decomposition method, each PC can be divided into two vectors, scores (t) and loadings (p). The scores can be described as the projection of each observation on to each PC and the loadings as the contribution of each variable (spectral bucket) to the PC expressed in terms of direction.

Any clustering of observations (samples) along a direction found in scores plots (e.g., PC1 versus PC2) can be explained by identifying which variables (spectral buckets) have high loadings for this particular direction in the scores. A high loading is defined as a variable (spectral bucket) that changes between the observations in a systematic way showing a trend which matches the sample positions in the scores plot. Each spectral bucket with a high loading, or a combination thereof, is defined by its $^1$H NMR chemical shift position; this is its diagnostic spectral window. These chemical shift values then allow the skilled NMR spectroscopist to examine the original NMR spectra and identify the molecules giving rise to the peaks in the relevant buckets; these are the biomarkers. This is typically done using a combination of standard 1- and 2-dimensional NMR methods.

If, in a scores plot, separation of two classes of sample can be seen in a particular direction, then examination of those loadings which are in the same direction as in the scores plots indicates which loadings are important for the class identification. The loadings plot shows points which are labelled according to the bucket chemical shift. This is the $^1$H NMR spectroscopic chemical shift which corresponds to the centre of the bucket. This bucket defines a diagnostic spectral window. Given a list of these bucket identifiers, the skilled NMR spectroscopist then re-examines the $^1$H NMR spectra and identifies, within the bucket width, which of several possible NMR resonances are changed between the two classes. The important resonance is characterised in terms of exact chemical shift, intensity, and peak multiplicity. Using other NMR experiments, such as 2-D NMR spectroscopy and/or separation of the specific molecule using HPLC-NMR-MS for example, other resonances from the same molecule are identified and ultimately, on the basis of all of the NMR data and other data if appropriate, an identification of the molecule (biomarker) is made.

In a classification situation as described herein, one procedure for finding relevant biomarkers using PCA is as follows:
  (a) PCA of the data matrix (X) containing N observations belonging to either of two known classes (healthy or diseased). The description of the observations lies in the K variables (spectral buckets) containing the biomarker information in terms of $^1$H NMR resonances.
  (b) Interpretation of the scores (t) to find the direction for the separation between the two known classes in X.
  (c) Interpretation of loadings (p) reveals which variables (spectral buckets) have the largest impact on the direction for separation described in the scores (t). This identifies the relevant diagnostic spectral windows.
  (d) Assignment of the spectral buckets or combinations thereof to certain biomarkers. This is done, for example, by interpretation of the resonances in $^1$H NMR spectra and by using previously assigned spectra of the same type as a library for assignments.

Interpreting PLS-DA Results

In PLS-DA, which is a regression extension of the PCA method, the options for interpretation are more extensive compared to the PCA case. PLS-DA performs a regression between the data matrix (X) and a "dummy matrix" (Y) containing the class membership information (e.g., samples may be assigned the value 1 for healthy and 2 for diseased classes). The calculated PLS components will describe the maximum covariance between X and Y which in this case is the same as maximum separation between the known classes in X. The interpretation of scores (t) and loadings (p) is the same in PLS-DA as in PCA. Interpretation of the PLS weights (w) for each component provides an explanation of the variables in X correlated to the variation in Y. This will give biomarker information for the separation between the classes.

Since PLS-DA is a regression method, the features of regression coefficients (b) can also be used for discovery and interpretation of biomarkers. The regression coefficients (b) in PLS-DA provide a summary of which variables in X (spectral buckets) that are most important in terms of both describing variation in X and correlating to Y. This means that variables (spectral buckets) with high regression coefficients are important for separating the known classes in X since the Y matrix against which it is correlated only contains information on the class identity of each sample.

Again, as discussed above, the scores plot is examined to identify important loadings, diagnostic spectral windows, relevant NMR resonances, and ultimately the associated biomarkers.

In a classification situation as described herein, one procedure for finding relevant biomarkers using PLS-DA is as follows:

(a) A PLS model between the N*K data matrix (X) against a "dummy matrix" Y, containing information on class membership for the observations in X, is calculated yielding a few latent variables (PLS components) describing maximum separation between the two classes in X (e.g., healthy and diseased).

(b) Interpretation of the scores (t) to find the direction for the separation between the two known classes in X.

(c) Interpretation of loadings (p) revealing which variables (spectral buckets) have the largest impact on the direction for separation described in the scores (t); these are diagnostic spectral windows.

In PLS-DA, a variable importance plot (VIP) is another method of evaluating the significance of loadings in causing a separation of class of sample in a scores plot. Typically, the VIP is a squared function of PLS weights, and therefore only positive numerical values are encountered; in addition, for a given model, there is only one set of VIP-values. Variables with a VIP value of greater than 1 are considered most influential for the model. The VIP shows each loading in a decreasing order of importance for class separation based on the PLS regression against class variable.

A (w*c) plot is another diagnostic plot obtained from a PLS-DA analysis. It shows which descriptors are mainly responsible for class separation. The (w*c) parameters are an attempt to describe the total variable correlations in the model, i.e., between the descriptors (e.g., NMR intensities in buckets), between the NMR descriptors and the class variables, and between class variables if they exist (in the present two class case, where samples are assigned by definition to class 1 and class 2 there is no correlation). Thus for a situation in a scores plot (e.g., t1 vs. t2), if class 1 samples are clustered in the upper right hand quadrant and class 2 samples are clustered in the lower left hand quadrant, then the (w*c) plot will show descriptors also in these quadrants. Descriptors in the upper right hand quadrant are increased in class 1 compared to class 2 and vice versa for the lower left hand quadrant.

(d) Interpretation of PLS weights (w) reveals which variables (spectral buckets) in X are important for correlation to Y (class separation); these, too, are diagnostic spectral windows.

(e) Interpretation of the PLS regression coefficients (b) reveals an overall summary of which variables (spectral buckets) have the largest impact on the direction for separation described in the scores; these, too, are diagnostic spectral windows.

In a typical regression coefficient plot for $^1$H NMR, each bar represents a spectral region (e.g., 0.04 ppm) and shows how the $^1$H NMR profile of one class of samples differs from the $^1$H NMR profile of a second class of samples. A positive value on the x-axis indicates there is a relatively greater concentration of metabolite (assigned using NMR chemical shift assignment tables) in one class as compared to the other class, and a negative value on the x-axis indicates a relatively lower concentration in one class as compared to the other class.

(f) Assignment of the spectral buckets or combinations thereof to certain biomarkers. This is done, for example, by interpretation of the resonances in $^1$H NMR spectra and by using previously assigned spectra of the same type as a library for assignments.

Timed Sampling

The analysis methods described herein can be applied to a single sample, or alternatively, to a timed series of samples. These samples may be taken relatively close together in time (e.g., daily) or less frequently (e.g., monthly or yearly).

The timed series of samples may be used for one or more purposes, e.g., to make sequential diagnoses, applying the same classification method as if each sample were a single sample. This will allow greater confidence in the diagnosis compared to obtaining a single sample for the patient, or alternatively to monitor temporal changes in the subject (e.g., changes in the underlying condition being diagnosed, treated, etc.).

Alternatively, the timed series of samples can be collectively treated as a single dataset increasing the information density of the input dataset and hence increasing the power of the analysis method to identify weaker patterns.

As yet another alternative, the timed series of samples can be collectively processed to yield a single dataset in which the temporal changes (e.g., in each bin) is included as an extra list of variables (e.g., as in composite data sets). Temporal changes in the amount of (e.g., endogenous) diagnostic species may greatly improve the ability of the analysis method to accurate classify patterns (especially when patterns are weak).

Batch Modelling

The methods described herein, including their applications (e.g., diagnosis, prognosis), may be further improved by employing batch modelling.

Statistical batch processing can be divided into two levels of multivariate modelling. The lower or the observation level is usually based on Partial Least Squares (PLS) regression against time (or any other index describing process maturity), whereas the upper or batch level consists of a PCA based on the scores from the lower level PLS model. PLS can also be used in the upper level to correlate the matrix based on the lower level scores with the end properties of the separate batches. This is common in industrial applications where properties of the end product are used as a description of quality.

At the lower level of the Batch modelling the evolution of the studied process with time (maturity) can be monitored and interpreted in terms of PLS scores and loadings. Since the PLS performs a regression against sampling time (maturity), the calculated components will be focused on the evolution with time. The fact that the calculated PLS components are orthogonal to each other means that it is possible to detect independent time (maturity) profiles and also to interpret which measured variables are causing these profiles. Confidence limits are used for detection of deviating behaviour of any spectra at any time point for some optional significance level, usually 95% and/or 99%.

The residuals expressed as distance to model (DModX) is, at the lower level, another important tool for detecting outlying batches or deviating behaviour for a specific batch at a specific time point. The upper level or batch level provides the possibility to just look at the difference between the separate batches. This is done by using the lower level scores including all time points for each batch as new variables describing each single batch and then performing a PCA on this new data matrix. The features of scores, loadings and DmodX are used in the same way as for ordinary PCA analysis, with the exception that the upper level loadings can be traced back down to the lower level for a more detailed explanation in the original loadings.

Predictions for "new" batches can be done on both levels of the batch model. On the lower level monitoring of evolution with time using scores and DmodX is a powerful tool for detecting deviating behaviour from normality for batch at any time point. On the upper level prediction of single batch behaviour can be done in terms of scores and DmodX.

The definition of a batch process, and also a requirement for batch modelling, is a process where all batches have equal duration and are synchronised according to sample collection. For example, samples taken from a cohort of animals at identical fixed time points to monitor the effects of an administered xenobiotic substance.

The advantage of using batch modelling for such studies is the possibility of detecting known, or discovering new, metabolic processes which evolve with time in the lower level scores, and also the identification of the actual metabolites involved in the different processes from the contributing lower level loadings. The lower level analysis also makes it possible to differentiate between single observations (e.g., individual animals at specific time points).

Applications for the lower level modelling include, for example, distinguishing between undosed controls and dosed animals in terms of metabolic effects of dosing in certain time points; and creating models for normality and using the models as a classification tool for new samples, e.g., as normal or abnormal. This may be achieved using a PLS prediction of the new sample's class using the model describing normality. Decisions can then be made on basis of the combination of the predicted scores and residuals (DmodX).

An automated expert system can be used for early fault detection in the lower level batch modelling, and this can be used to further enhance the analysis procedure and improve efficiency.

The upper level provides the possibility of making predictions of new animals using the existing model. Abnormal animals can then be detected by judging predicted scores and residuals (DmodX) together. Since the upper level model is based on the lower level scores, the interpretation of an animal predicted to be abnormal can be traced back to the original lower level scores and loadings as well as the original raw variables making up the NMR spectra. Combining the upper and lower level for prediction of the status of a new animal, the classification can be based on four parameters: upper level scores and residuals (DmodX) and lover level scores and residuals (DModX). This demonstrates that batch modelling is an efficient tool for determining if an animal is normal or abnormal, and if the latter, why and when they are deviating from normality.

See, for example, Wold et al, 1998 and Eriksson et al., 1999.

Integrated Metabonomics

As discussed above, many of the methods of the present invention may also be applied to composite data or composite data sets. The term "composite data set," as used herein, pertains to a spectrum (or data vector) which comprises spectral data (e.g., NMR spectral data, e.g., an NMR spectrum) as well as at least one other datum or data vector. Examples of other data vectors include, e.g., one or more other NMR spectral data, e.g., NMR spectra, e.g., obtained for the same sample using a different NMR technique; other types of spectra, e.g., mass spectra, numerical representations of images, etc.; obtained for the another sample, of the same sample type (e.g., blood, urine, tissue, tissue extract), but obtained from the subject at a different timepoint; obtained for another sample of different sample type (e.g., blood, urine, tissue, tissue extract) for the same subject; and the like.

Examples of other data including, e.g., one or more clinical parameters. Clinical parameters which are suitable for use in composite methods include, but are not limited to, the following:

(a) established clinical parameters routinely measured in hospital clincal labs: age; sex; body mass index; height; weight; family history; medication history; cigarette smoking; alcohol intake; blood pressure; full blood cell count (FBCs); red blood cells; white blood cells; monocytes; lymphocytes; neutrophils; eosinophils; basophils; platelets; haematocrit; haemoglobin; mean corpuscular volume and related haemodilution indicators; fibrinogen; functional clotting parameters (thromoboplastin and partial thromboplastin); electrolytes (sodium, potassium, calcium, phosphate); urea; creatinine; total protein; albumin; globulin; bilirubin; protein markers of liver function (alanine aminotransferase, alkaline phosphatase, gamma glutamyl transferase); glucose; Hba1c (a measure of glucose-Haemoglobin conjugates used to monitor diabetes); lipoprotein profile; total cholesterol; LDL; HDL; triglycerides; blood group.

(b) established research parameters routinely measured in research laboratories but not usually measured in hospitals: hormonal status; testosterone; estrogen; progesterone; follicle stimulating hormone; inhibin; transforming growth factor-beta1; Transforming growth factor-beta2; chemokines; MCP-1; eotaxin; plasminogen activator inhibitor-1; cystatin C.

(c) early-stage research parameters measured in one or a small number of specialist labs: antibodies to sRII; antibodies to blood group A antigen; antibodies to blood group B antigen; immunoglobulin (IgD) against alpha-gal; immunoglobulin (IgD) against penta-gal.

B: Isatin Assay for Proline

As discussed above, many of the methods of the present invention involve the amount, or relative amount, of free proline. Some suitable methods for determining free proline, which may conveniently be described as isatin assays, are described below.

There have only been a small number of previous reports of the measurement of serum proline, mostly using chromatographic separation. These studies reported that the normal range of serum proline concentrations in several different populations was 200-300 µM (see, e.g., Stein et al., 1954a, 1954b; Tanaka et al., 1986) and that no alteration in serum proline levels were associated with the progress of various fibrotic diseases, such as liver cirrhosis. While being very accurate, such techniques are not well suited to population comparisons in cohorts with several hundred individuals, as each sample must be analysed separately.

A colorimetric determination of serum proline concentration has been reported (see, e.g., Boctor et al., 1971) which exploited the specific chemical interaction between proline and isatin (2,3-indolinedione) to form a blue-coloured insoluble product with an absorption maximum near 595 nm. This method, which employs 5 ml sample tubes, requires four steps (deproteinisation, removal of picric acid with ion-exchange resin, boiling with alcohol, and extraction of the precipitate with acetone), including a lengthy step for the extraction of the blue preciptated product with acetone.

There remains a lack of a relatively high throughput assay for proline in biological fluids.

The inventors have developed a sensitive and specific microtitre plate format assay for proline which exploits the chemical interaction between proline and isatin. This assay has significant advantages as compared to assays described previously, particularly in terms of the numbers of samples which can be measured simultaneously. The improved assays offers one or more of the following advantages:
(a) it is substantially simpler to perform;
(b) suitable for use in a conventional microtitre plate;
(c) it requires only two steps (deproteinisation followed by calorimetric determination);
(d) it circumvents the requirement for a lengthy step for the extraction of the blue preciptated product with acetone;
(e) it offers a coefficient of variation between replicates which is comparable with HPLC determinations.

a method of determining the proline content of a sample

One aspect of the present invention pertains to a method of determining (or, an assay for) the proline content of a sample, said method comprising the steps of:
(a) contacting said sample with sodium citrate buffer to form a precipitate;
(b) separating supernatant from said precipitate;
(c) contacting said supernatant with satin to form a mixture; and,
(d) quantifying any resultant blue colored product in said mixture.

In one embodiment, said sample is sample as described hereinabove.

In one embodiment, said sample is a serum sample or a plasma sample.

In one embodiment, said sample is a human serum sample or a human plasma sample.

In one embodiment, step (a) is contacting said sample with sodium citrate buffer pH 4.1 to form a precipitate.

In one embodiment, step (a) is contacting said sample with sodium citrate buffer pH 4.1 at about 95° C. to form a precipitate.

In one embodiment, step (a) is contacting said sample with sodium citrate buffer pH 4.1 at about 95° C. for about 1 hour to form a precipitate.

In one embodiment, said sodium citrate buffer is 500 mM sodium citrate buffer pH 4.1.

In one embodiment, said sodium citrate buffer is 500 mM sodium citrate buffer pH 4.1 and is in an amount approximately equal to the volume of said sample.

In one embodiment, step (b) is separating supernatant from said precipitate by centrifugation.

In one embodiment, the supernatant of step (b) contains less than 5% (w/w) of the protein in the sample.

In one embodiment, the supernatant of step (b) contains less than 3% (w/w) of the protein in the sample.

In one embodiment, the supernatant of step (b) contains less than 2% (w/w) of the protein in the sample.

In one embodiment, the supernatant of step (b) contains less than 1% (w/w) of the protein in the sample.

In one embodiment, the supernatant of step (b) contains less than 0.5% (w/w) of the protein in the sample.

In one embodiment, step (c) is contacting said supernatant with isatin to form a mixture with a final isatin concentration of about 0.2% (w/v).

In one embodiment, step (c) is contacting said supernatant with isatin to form a mixture and incubating said mixture at about 95° C.

In one embodiment, step (c) is contacting said supernatant with isatin to form a mixture with a final isatin concentration of about 0.2% (w/v) and incubating said mixture at about 95° C.

In one embodiment, step (c) is contacting said supernatant with isatin to form a mixture and incubating said mixture at about 95° C. for about 3 hours.

In one embodiment, step (c) is contacting said supernatant with isatin to form a mixture with a final isatin concentration of about 0.2% (w/v) and incubating said mixture at about 95° C. for about 3 hours.

In one embodiment, after step (c) and before step (d), there is the additional step of adding DMSO to said mixture.

In one embodiment, after step (c) and before step (d), there are the additional steps of: adding DMSO to said mixture; and, mixing the resulting DMSO-mixture.

In one embodiment, after step (c) and before step (d), there are the additional steps of: adding DMSO to said mixture; mixing the resulting DMSO-mixture; and incubating the resulting DMSO-mixture for about 15 minutes at about 20° C.

In one embodiment, the mixing step is mixing resulting DMSO-mixture by shaking.

In one embodiment, the resulting DMSO-mixture a final DMSO concentration of about 25% by volume.

In one embodiment, step (d) is quantifying any resultant blue colored product in said mixture spectrophotometrically.

In one embodiment, step (d) is quantifying any resultant blue colored product in said mixture spectrophotometrically at about 595 nm.

In one embodiment, step (d) is performed with reference to a control sample having a known quantity of proline.

In one embodiment, the method (e.g., assay) is a microtitre plate format method (e.g., assay).

In one embodiment, said amount, or relative amount, is determined by an isatin assay, for example, as described above.

Preparation of Serum and Plasma Samples

Serum and plasma were prepared from blood withdrawn from the cubital vein using a 19-gauge butterfly needle without the application of a tourniquet.

For serum, the blood was allowed to clot in a polypropylene tube for 2 hours at room temperature, then cells and the clot were spun out at 1000 g for 5 minutes and the supernatant (serum) removed.

For plasma, the blood was immediately mixed with anticoagulant (Diatube H; Diagnostica Stago) and incubated on ice for 15 minutes. Cells were then spun out at 2500 g for 30 minutes at 2-8° C. and the central one-third of the supernatant taken.

All samples were aliqoted and stored at −80° C. until assayed.

Deproteinization

Protein does not interfere with the assay directly (proline contained in proteins does not react with isatin), but it does precipitate under the highly denaturing conditions of the assay, thereby hindering or preventing spectrophotometric quantitation. Traditional methods of precipitating protein (e.g., treatment with 15% trichloroacetic acid or picric acid) do not remove sufficient protein to prevent a further precipitate forming at 95° C.

Deproteinisation was therefore carried out as follows: an equal volume of 500 mM sodium citrate buffer pH 4.1 is added to serum, mixed and incubated at 95° C. in an oven for 1 hour. Precipitated protein was then spun out (25,000 g for 10 minutes) and the supernatant retained for proline assay. This method removes 99.8±0.1% of the protein present in serum. Note that the supernatant must be removed very carefully, since transfer of even a small amount of precipitated protein results in over-estimation of the serum proline concentration.

For each assay, a 10 mM standard solution of L-proline (99% purity; Sigma) in water was prepared (weighing out at least 100 mg of solid to ensure accuracy) and discarded after use. This solution was diluted into phosphate buffered saline containing 70 mg/ml bovine serum albumin to prepare a series of standard solutions ranging from 1 mM to 15.8 µM proline concentration. These standards were subject to the deproteinisation procedure along side the serum samples.

Proline Assay

A 10% (w/v) stock solution of isatin (99% purity; Aldrich Chemical Co.) in DMSO was prepared and stored in the dark at room temperature for up to 1 week. 150 µl of each deproteinised standard or serum sample was then dispensed into a half-area 96-well microtitre plate (well volume ~200 µl; Code #3697, Corning). To each sample, 3 µl of isatin stock solution was added with mixing, generating a final isatin concentration of 0.2% (w/v) which is just below the limit of solubility of isatin in aqueous solution at room temperature. The spacer volumes between the wells of the plate were then filled with water and an adhesive plate sealer was firmly applied to prevent any possible of evaporation during the subsequent incubation. The plate was then incubated at 95° C. in an oven for 3 hours.

Formation of a blue suspension/precipitate in wells containing proline is visible by the end of the incubation. This suspension was fully dissolved by addition of 50 µl DMSO to each well (25% v/v final concentration) and mixed thoroughly on an orbital shaker, then incubated at room temperature for 15 minutes. After further orbital mixing, the plate was read at 595 nm and proline concentrations in the unknown samples calculated by interpolation of a linear-linear plot of a standard curve.

All incubations were performed in the dark. Standards and unknown samples were routinely assayed in duplicate.

Assay Characteristics

The kinetics of formation of the blue product was first investigated at room temperature, 45° C. and 95° C. The reaction proceeds with complex kinetics which are not adequately described by any simple biomolecular models, but equilibrium was apparently achieved after 2 hours at 95° C. There was no appreciable reaction at room temperature even after 8 hours and only a partial reaction at 45° C. The initial reaction rates, the Vmax rates, and the equilibrium absorbance were all correlated with proline concentration in the standards, but only the end-point determination of absorbance was sufficiently reproducible for assay purposes ($r=0.998\pm0.001$; n=8 determinations).

The other 19 proteogenic amino acids, plus taurine, citrulline and hydroxyproline were tested for cross-reactivity in this assay. With the exception of hydroxyproline, all of these amino acids read at <30 µM apparent proline concentration when tested at 10 mM, representing a cross-reactivity of <0.3%. The reading was only statistically significantly above background for cysteine (0.26%) and tryptophan (0.25%). Hydroxyproline showed a more significant cross-reactivity, with an apparent proline concentration of 312±14 µM when tested at 10 mM (3% cross-reactivity). Although this cross-reaction is statistically significant, it is unlikely to have any practical significance because circulating levels of hydroxyproline above 200 µM have not been reported, even among individuals with bone disorders who have elevated levels of this metabolite. At 200 µM, a 3% cross reactivity would result in an artefactual increase in serum proline concentration of approximately 2%.

The sensitivity of the assay, defined as the proline concentration equivalent to twice the standard deviation of eight sample blanks, was determined on three separate occasions. A linear standard curve in the range 15 µM to 1 mM ($r=0.998\pm0.002$; n=8 determinations) was obtained. The detection threshold was 31±11 µM, suggesting the assay is, at least, suitable for the detection of proline in serum or plasma which is in the range 200-300 µM.

To determine whether the assay shows linear dilution characteristics, two samples were prepared: serum from an individual (identified in a preliminary screen of healthy laboratory workers) with a relatively high level of proline (~400 µM), and serum from this individual with additional proline spiked into it, raising the final concentration by 500 µM. These samples were then assayed neat, and after serial two fold dilution in phosphate buffered saline (PBS) prior to deproteinisation. The assay showed excellent linear dilution characteristics for both samples, right down to the sensitivity threshold of the assay. The mean recovery of the spiked proline was 107±5% across the range of dilutions tested.

The reproducibility of the assay was characterised by measuring eight replicate aliquots of the same serum preparation (containing 323 µM proline) on each of three days. All the assays were performed by the same operator who had considerable practice at removing the supernatant following deproteinisation without disturbing the precipitated protein. The intra-assay coefficient of variation (CV) was 4.8% and the intra-day CV was 6.1%. (Note that it is difficult to achieve a coefficient of variation below 20% using the known isatin method.) Thus, the assay has reproducibility characteristics similar to many immunological or enzymatic assays currently used in biochemical laboratories.

In order to compare the original Boctor assay and the inventors' assay, as described herein, eleven (11) serum samples were measured on three (3) different days by each of the two methods. Some precise details regarding the methods are shown in the following table:

| Comparison of Assay Methods | |
| --- | --- |
| New Assay | Boctor Assay |
| Sample volume required: 100 µl. | Sample volume required: 1 ml. |
| 1. Deproteinise by addition of an equal volume of 500 mM citrate pH 4.1 at 95° C. for 1 hour. Spin and remove supernatant for assay. | 1. Deproteinise by addition of 5 volumes of 1% picric acid at room temperature for 30 mins. Spin and remove supernatant. |
|  | 2. Remove picric acid by passing through a Dowex 2-X8 ion exchange column. |
| 3. Add 10% isatin in DMSO to give final concentration of 0.2% w/v. Incubate for 3 hours at 95° C. | 3. Add 0.02% isatin in citrate buffer to give 0.01% w/v isatin, then add 10 volumes of 96% ethanol. Place in boiling water bath until all liquid has evaporated. |
| 4. Dissolve any precipitate by addition of DMSO (25% v/v final concentration). | 4. Extract precipitate with 3 ml of acetone/water (2:1 v/v). |
| 5. Read in microtitre plate reader at 595 nm. | 5. Read in a cuvette at 595 nm. |

The results are summarised in the following table.

| Comparison of Assay Results | | | | | |
| --- | --- | --- | --- | --- | --- |
| | New Assay | | | Boctor Assay | |
| # | Measurements | Mean | CV (%) | Measurements | Mean | CV (%) |
| 1 | 235, 225, 250 | 237 | 5.3 | 220, 200, 410 | 277 | 41.9 |
| 2 | 200, 200, 250 | 217 | 13.0 | 270, 300, 170 | 247 | 27.6 |
| 3 | 330, 290, 320 | 313 | 6.6 | 270, 720, 350 | 447 | 53.7 |

-continued

Comparison of Assay Results

| | New Assay | | | Boctor Assay | | |
|---|---|---|---|---|---|---|
| # | Measurements | Mean | CV (%) | Measurements | Mean | CV (%) |
| 4 | 180, 190, 190 | 187 | 3.1 | 150, <100, <100 | <117 | >24.7 |
| 5 | 265, 255, 270 | 263 | 2.9 | 380, 280, 220 | 293 | 27.5 |
| 6 | 300, 260, 265 | 275 | 7.9 | 320, 270, 370 | 320 | 15.6 |
| 7 | 285, 260, 290 | 278 | 5.8 | 250, 360, 260 | 290 | 20.1 |
| 8 | 420, 415, 440 | 425 | 3.1 | 380, 770, 560 | 570 | 34.2 |
| 9 | 195, 170, 180 | 182 | 6.9 | <100, 220, 270 | <197 | >44.4 |
| 10 | 150, 180, 175 | 168 | 9.5 | <100, 320, <100 | <173 | >73.2 |
| 11 | 250, 265, 250 | 255 | 3.4 | 200, 370, 300 | 290 | 29.5 |
| | Mean | 254 | 6.1 | Mean | 293 | 35.7 |

The data demonstrate that, not only is the new assay faster and easier to perform than the Boctor assay, but it also permits a 10-fold reduction in sample volume, the use of a microtitre plate format, and is also substantially more reproducible. The mean coefficient of variation (CV) for the 11 samples was 6.1% for the new assay compared with 35.7% for the Boctor assay.

Comparison with NMR Data

The quantitative levels of proline as determined by the new assay have been compared with the bucket integral values determined from the NMR spectra of the blood serum. These bucket integrals, in addition to containing a contribution from the proline NMR peaks, are also affected by contributions from many other molecular species, especially macromolecules such as albumin which have broad NMR peaks and contribute to many buckets. Hence a strong statistical correlation is not expected between the NMR and isatin assay values. However a correlation analysis between isatin-assay determined proline and NMR bucket integral values showed statistically significant values (correlation coefficients using Pearson's R statistic, Fishers r to z transformation; p<0.05) for the NMR buckets at 3.38, 3.34, 3.42. 2.06 and 2.02 but not at 2.34, as shown in the following table.

Comparison of Proline Assay with NMR Data

| NMR Bucket | Assignment | Correlation (n = 118) |
|---|---|---|
| 3.38 | Half $\delta$-CH$_2$ | 0.216 |
| 3.34 | Half $\delta$-CH$_2$ | 0.228 |
| 3.42 | Half $\delta$-CH$_2$ | 0.428 |
| 2.34 | Half $\beta$-CH$_2$ | 0.107 |
| 2.06 | Half $\beta$-CH$_2$ | 0.529 |
| 2.02 | $\gamma$-CH$_2$ | 0.413 |

The assay was used in epidemiological analysis of cohorts in an effort to identify factors which may be important in regulating serum proline levels.

The assay was used to measure the proline concentration in serum samples from 80 apparently healthy individuals (age range: 30 to 76; mean: 56±9 years). Serum proline concentration was approximately normally distributed in this population with a mean of 258 $\mu$M and a standard deviation of 55 $\mu$M, consistent with previous chromatographic determinations. There was no statistically significant difference between the sexes (males: 260±48 $\mu$M (n=38); females 252±58 $\mu$M (n=42)).

Serum proline is not associated with age (r=0.02; p=0.98) or with age of onset of menopause (r=0.072; p=0.57). Although serum proline is associated with weight, body mass index, and body composition, these measures are also tightly associated with a diagnosis of OP, making it difficult to determine whether they are genuinely associated with proline metabolism or whether bone mineral density is a confounding variable in the analysis. Hormone replacement therapy may be associated with significantly higher serum proline levels in the normal population (253±17 $\mu$M versus 243±8 $\mu$M) which might explain some of the benefit of the hormone therapy, but this observation may also result from the greater general health awareness of women taking hormone replacement therapy.

Interestingly, serum proline levels are robustly associated with proline content of the diet: vegetarians who take in, on average only 30% of the proline content of a meat-eater (because most dietary proline in obtained from collagen, an exclusively animal protein), have lower serum proline than meat eaters (202±17 $\mu$M versus 261±12 $\mu$M among meat-eaters). Within the meat-eaters, serum proline was directly correlated with the amount of meat consumed (r=0.329; p<0.05). Taken together, these observations suggests (a) that dietary proline intake is a major determinant of serum proline levels and hence proline availability for collagen biosynthesis, and (b) that proline metabolism could account for the recent observations that long-term vegetarians are at increased risk of osteoporosis compared to meat-eaters (see, e.g., Promislow et al., 2002).

Kits

One aspect of the present invention pertains to reagents, reagent mixtures, reagent sets comprising one or more separate reagents, and reagent kits (e.g., test kits) comprising one or more reagents, reagent mixtures, and reagent sets in packaged combination, all for use in the assay methods described herein.

Reagents, reagent mixtures, and/or sets of reagents for use in the assays described herein are typically provided in one or more suitable containers or devices. Each reagent may be in a separate container or various reagents can be combined in one or more containers (e.g., as a reagent mixture), depending on the compatibility (e.g., cross-reactivity) and stability of the reagents. Reagents (or reagent mixtures) may be in solid (e.g., lyophilised), liquid, or gaseous form, though typically are in solid or liquid form.

Reagents, reagent mixtures, and/or reagent sets are typically presented in a commercially packaged form as a reagent kit; for example, as a packaged combination of one or more containers, devices, or the like holding one or more reagents or reagent mixtures, and usually including written instructions for the performance of the assays. Reagent kits may also include materials (e.g., reagents, standards, etc.) for calibration and control purposes.

Reagents and reagent mixtures may further comprise one or more ancilliary materials, including, but not limited to, buffers, surfactants (e.g., non-ionic surfactants), stabilisers, preservatives, and the like.

C: Enzymatic Assays

As discussed above, many of the methods of the present invention involve the amount, or relative amount, of free proline. Some suitable methods for determining free proline, which may conveniently be described as enzymatic assays, are described below.

A range of enzymes which interconvert amino acids into proline are known. See, for example, FIG. 1 on page 1010 of Adams et al., 1980. Many of these enzymes have now been cloned either from mammalian sources or from bacteria. These enzymes can be utilised to measure the concentration of proline present in a sample. Importantly, none of the enzyme activities shown in this figure are present in human serum or plasma; this fact greatly simplifies the design of an enzymatic assay for such samples.

In general, enzyme assays rely upon the (usually specific) conversion of one species to another species by a particular enzyme. For example, in one approach, an enzyme is added to a sample containing an analyte of interest (e.g., proline) which specifically converts the analyte into a product. The reaction is monitored, for example, via the rate of the enzyme reaction or the total amount of product formed.

For example, a very common colorimetric determination relies upon the formation of a bright blue formazan product from a tetrazolium salt dye using a dehydrogenase enzyme (e.g., lactate dehydrogenase).

Thus, one general enzyme assay is based upon the following reactions:

Analyte+NAD⁺→product+NADH    (1)

NADH+tetrazolium→blue formazan+NAD⁺    (2)

where NAD⁺ is nicotinamide adenine dinucleotide, and in the reduced form is, NADH. Reaction (1) is catalysed by an appropriate enzyme which is specific for the analyte under study and reaction (2) is catalysed by an appropriate dehydrogenase (e.g., lactate dehydrogenase). Typically, in practice, both enzymes as well as NAD⁺ are added to the sample to be tested; the reaction is allowed to run to completion (e.g., at 37° C.); and the total amount of formazan product formed is determined.

Assays of this general type are routinely used in clinical analysers to measure biochemical analytes of interest. For example, glucose is measured in hospitals by an assay based on this principal which uses glucose oxidase as the enzyme that specifically reacts with the analyte (glucose).

Enzymatic assays for proline may, for example, rely upon a first enzyme (e.g., proline oxidase) for the conversion of proline to pyrroline-carboxylate (P5C) (e.g., reaction (3) below); a second enzyme (e.g., P5C dehydrogenase, P5CDH) for a reaction with the product (P5C) to form NADH (e.g., reaction (4) below); and a third enzyme, e.g., a dehydrogenase (e.g., lactate dehydrogenase) to generate a colored product (e.g., formazan) from NADH (e.g., reaction (5) below).

proline→P5C    (3)

P5C+NAD⁺→product+NADH    (4)

NADH+tetrazolium→blue formazan+NAD⁺    (5)

For example, in one embodiment, lactate dehydrogenase and P5C dehydrogenase are added to a serum sample, and the mixture incubated (e.g., at 37° C. for 30 mins), in order to pre-clear the system of endogenous NADH and P5C. Then, in order to initiate the assay, proline oxidase, NAD and tetrazolium salt are added. The concentration of proline oxidase should be rate limiting over P5C dehydrogenase and lactate dehydrogenase activities.

The initial rate of reaction (Vmax), the equilibrium concentration of formzan product, or any other suitable parameter may be used as an indicator of proline. Proline concentration can be determined from the experimental data using well known methods. For example, proline concentration can be determined by interpolation of a standard curve generated from standard solutions of known proline concentration.

A variety of different combinations of enzymes which utilise proline as a substrate may used to create analogous enzymatic assays for the determination of proline concentration. For example, one combination is: proline racemase and D-proline reductase. Another combination is: proline oxidase and ornithine transaminase.

Again, such assays can be adapted for use on many of the autoanalysers currently in use in clinical laboratories.

In one embodiment, said amount, or relative amount, is determined by an enzyme assay.

In one embodiment, said amount, or relative amount, is determined by an enzyme assay employing P5CDH.

In one embodiment, said amount, or relative amount, is determined by an enzyme assay employing proline oxidase and P5CDH.

In one embodiment, said amount, or relative amount, is determined by an enzyme assay employing proline racemase and D-proline reductase.

In one embodiment, said amount, or relative amount, is determined by an enzyme assay employing proline oxidase and ornithine transaminase.

D: Other Conventional Methods

As discussed above, many of the methods of the present invention involve the amount, or relative amount, of free proline. A wide range of other conventional well known methods for amino acid analysis may be used, and some of these are briefly described below.

For example, amino acid analysis can be performed on aqueous solutions containing free amino acids or on proteins and peptides following hydrolysis to release the amino adds. A common method for protein hydrolysis uses 6N HCl in sealed evacuated tubes for 20-24 hrs. at 110° C. Samples are preferably deproteinized before analysis. A common method of deproteinization is protein precipitation by TCA (trichloroacetic acid) followed by ethyl acetate or ether extraction of the residual TCA. Typically, samples are free of any amines, TRIS buffer, or urea. Typically, the presence of other salts is acceptable at low concentrations (less than 0.1 M in 100 microliters).

Amino acid analysis may be performed using, for example, chromatographic methods such as, for example, ion-exchange chromatography and high pressure liquid chromatography (HPLC).

For example, amino acid analysis may be performed by cation exchange chromatography. Amino acid elution may be accomplished, for example, by using a two buffer system; initially eluting with 0.2 N sodium citrate, pH 3.28 followed by 1.0 N sodium citrate, pH 7.4. Amino acids may be detected, for example, by on-line post column reaction, for example, by reaction with ninhydrin. Derivatized amino acids may be quantitated, for example, by their absorption at 570 nm wavelength, except for glutamic acid and proline, which are detected at 440 nm wavelength. This procedure may be performed, for example, on an automated Beckman system Gold HPLC amino acid analyzer. See, for example, West et al., 1989.

In another method, amino acid analysis may be performed by ion-exchange chromatography employing post-column derivatisation with Ortho-phthaldialdehyde (OPA).

Another method is reverse-phase HPLC employing pre-column derivatisation with DABSYL reagent. This method is more sensitive, and all normal amino acids are quantified, but it is also more expensive.

In one embodiment, said amount, or relative amount, is determined by chromatography.

In one embodiment, said amount, or relative amount, is determined by ion-exchange chromatography.

In one embodiment, said amount, or relative amount, is determined by high pressure liquid chromatography (HPLC).

Implementation

The methods of the present invention, or parts thereof, may be conveniently performed electronically, for example, using a suitably programmed computer system.

One aspect of the present invention pertains to a computer system or device, such as a computer or linked computers, operatively configured to implement a method of the present invention, as described herein.

One aspect of the present invention pertains to computer code suitable for implementing a method of the present invention, as described herein, on a suitable computer system.

One aspect of the present invention pertains to a computer program comprising computer program means adapted to perform a method according to the present invention, as described herein, when said program is run on a computer.

One aspect of the present invention pertains to a computer program, as described above; embodied on a computer readable medium.

One aspect of the present invention pertains to a data carrier which carries computer code suitable for implementing a method of the present invention, as described herein, on a suitable computer.

In one embodiment, the above-mentioned computer code or computer program includes, or is accompanied by, computer code and/or computer readable data representing a predictive mathematical model, as described herein.

In one embodiment, the above-mentioned computer code or computer program includes, or is accompanied by, computer code and/or computer readable data representing data from which a predictive mathematical model, as described herein, may be calculated.

One aspect of the present invention pertains to computer code and/or computer readable data representing a predictive mathematical model, as described herein.

One aspect of the present invention pertains to a data carrier which carries computer code and/or computer readable data representing a predictive mathematical model, as described herein.

One aspect of the present invention pertains to a computer system or device, such as a computer or linked computers, programmed or loaded with computer code and/or computer readable data representing a predictive mathematical model, as described herein.

Computers may be linked, for example, internally (e.g., on the same circuit board, on different circuit boards which are part of the same unit), by cabling (e.g., networking, ethernet, internet), using wireless technology (e.g., radio, microwave, satellite link, cell-phone), etc., or by a combination thereof.

Examples of data carriers and computer readable media include chip media (e.g., ROM, RAM, flash memory (e.g., Memory Stick™, Compact Flash™, Smartmedia™), magnetic disk media (e.g., floppy disks, hard drives), optical disk media (e.g., compact disks (CDs), digital versatile disks (DVDs), magneto-optical (MO) disks), and magnetic tape media.

Although the $^1$H-NMR spectra analysed here were generated using a conventional (and hence large and expensive) 600 MHz NMR spectrometer, on-going technological advances suggest that spectrometers of similar resolving power may soon be available as desktop units (provided the sample to be analyzed is small, as is the case with plasma or serum samples). Such units, together with a personal computer to perform automated pattern recognition, may soon be available not only in large hospitals but also in the primary healthcare milieu.

One aspect of the present invention pertains to a system (e.g., an "integrated analyser", "diagnostic apparatus") which comprises:

(a) a first component comprising a device for obtaining NMR spectral intensity data for a sample (e.g., a NMR spectrometer, e.g., a Bruker INCA 500 MHz); and, (b) a second component comprising computer system or device, such as a computer or linked computers, operatively configured to implement a method of the present invention, as described herein, and operatively linked to said first component.

In one embodiment, the first and second components are in close proximity, e.g., so as to form a single console, unit, system, etc. In one embodiment, the first and second components are remote (e.g., in separate rooms, in separate buildings).

A simple process for the use of such a system is described below.

In a first step, a sample (e.g., blood, urine, etc.) is obtained from a subject, for example, by a suitably qualified medical technician, nurse, etc., and the sample is processed as required. For example, a blood sample may be drawn, and subsequently processed to yield a serum sample, within about three hours.

In a second step, the sample is appropriately processed (e.g., by dilution, as described herein), and an NMR spectrum is obtained for the sample, for example, by a suitably qualified NMR technician. Typically, this would require about fifteen minutes.

In a third step, the NMR spectrum is analysed and/or classified using a method of the present invention, as described herein. This may be performed, for example, using a computer system or device, such as a computer or linked computers, operatively configured to implement the methods described herein. In one embodiment, this step is performed at a location remote from the previous step. For example, an NMR spectrometer located in a hospital or clinic may be linked, for example, by ethernet, internet, or wireless connection, to a remote computer which performs the analysis/classification. If appropriate, the result is then forwarded to the appropriate destination, e.g., the attending physician. Typically, this would require about fifteen minutes.

Applications

The methods described herein provide powerful means for the diagnosis and prognosis of disease, for assisting medical practitioners in providing optimum therapy for disease, for understanding the benefits and side-effects of xenobiotic compounds thereby aiding the drug development process, as well as for many other applications.

Furthermore, the methods described herein can be applied in a non-medical setting, such as in post mortem examinations and forensic science.

Examples of these and other applications of the methods described herein include, but are not limited to, the following:

Medical Diagnostic Applications (a) Early detection of abnormality/problem. For example, the methods described herein can be used to identify a clinically silent disease (e.g., low bone mineral density (osteoporosis)), prior to the onset of clinical symptoms (e.g., fracture).

(b) Diagnosis (identification of disease), especially cheap, rapid, and non-invasive diagnosis.

(c) Differential diagnosis, e.g., classification of disease, severity of disease, the ability to distinguish disease at different anatomical sites.

(d) Population targeting. A condition (e.g., osteoporosis) may be clinically silent for many years prior to an acute event (e.g., bone fracture), which may have significant associated morbidity or mortality. Drugs may exist to help prevent the acute event (e.g., bisphosphonates for osteoporosis), but often they cannot be efficiently targeted at the population level. The requirements for a test to be useful for population screening are that they must be cheap and non-invasive. The methods described herein are ideally suited to population screening. Screens for multiple diseases with a single blood sample (e.g., osteoporosis, heart disease, and cancer) further improve the cost/benefit ratio for screening.
(e) Classification, fingerprinting, and diagnosis of metabolic diseases (e.g., inborn errors of metabolism).

Medical Prognosis Applications (a) Prognosis (prediction of future outcome), including, for example, analysis of "old" samples to effect retrospective prognosis. For example, a sample can be used to assess the risk of osteoporosis among high risk groups, permitting a more aggressive therapeutic strategy to be applied to those at greatest risk of progressing to a fracture.
(b) Risk assessment, to identify people at risk of suffering from a particular indication. The methods described herein can be used for population screening (as for diagnosis) but in this case to screen for the risk of developing a particular disease. Such an approach will be useful where an effective prophylaxis is known but must be applied prior to the development of the disease in order to be effective. For example, bisphosphonates are effective at preventing bone loss in osteoporosis but they do not increase pathologically low bone mineral density. Ideally, therefore, these drugs are applied prior to any bone loss occurring. This can only be done with a technique which facilitates prediction of future disease (prognosis). The methods described herein can be used to identify those people at high risk of losing bone mineral density in the future, so that prophylaxis may begin prior to disease inception.
(c) Antenatal screening for disease susceptibility. The methods described herein can be used to analyse blood or tissue drawn from a pre-term fetus (e.g., during chorionic vilus sampling or amniocentesis) for the purposes of antenatal screening.

Aids to Theraputic Intervention (a) Therapeutic monitoring (e.g., of proline levels), e.g., to monitor the progress of treatment. For example, by making serial diagnostic tests, it will be possible to determine whether and to what extent the subject is returning to normal following initiation of a therapeutic regimen.
(b) Patient compliance, e.g., monitoring patient compliance with therapy. Patient compliance is often very poor, particularly with therapies that have significant side-effects. Patients often claim to comply with the therapeutic regimen, but this may not always be the case. The methods described herein permit the patient compliance to be monitored, for example by measuring the biological consequences of the drug. Thus, the methods described herein offer significant advantages over existing methods of monitoring compliance (such as measuring plasma concentrations of the drug) since the patient may take the drug just prior to the investigation, while having failed to comply for previous weeks or months. By monitoring the biological consequences of therapy, it is possible to assess long-term compliance.
(c) The methods described herein can be used for "pharmacometabonomics," in analogy to pharmacogenomics, e.g., subjects could be divided into "responders" and "nonresponders" using the metabonomic profile (including, e.g., proline level) as evidence of "response," and features of the metabonomic profile could then be used to target future patients who would likely respond to a particular therapeutic course.

Commercial and Other Non-Medical Applications (a) Commercial classification for actuarial assessment, to address the commercial need for insurance companies to assess future risk of disease. Examples include the provision of health insurance and general life cover. This application is similar to prognostic assessment and risk assessment in population screening, except that the purpose is to provide accurate actuarial information.
(b) Clinical trial enrolment, to address the commercial need for the ability to select individuals suffering from, or at risk of suffering from, a particular condition for enrolment in clinical trials. For example, at present to perform a clinical trial to assess efficacy of a drug intended to prevent heart disease it would be necessary to enroll at least 4,000 subjects and follow them for 4 years. If it were possible to select individuals who were suffering from heart disease, it is estimated that it would be possible to use 400 subjects followed for 2 years reducing the cost by 25-fold or more.
(c) Application to pathology and post-mortem studies. For example, the methods described herein could be used to identify the proximate cause of death in a subject undergoing post-mortem examination.

The methods described herein may be used as an alternative or adjunct to other methods, e.g., the various genomic, pharmacogenomic, and proteomic methods.

Other Aspects of the Invention

Once an individual has been identified as proline deficient, for example, using the methods described herein, it may be desirable to return serum proline levels to the normal range, and thereby reduce the risk of diseases specifically linked with proline deficiency, e.g., bone disorders, e.g., conditions associated with low bone mineral density, e.g., osteoporosis.

Depending upon the cause of the proline deficiency, proline levels may be normalised, for example, by:
  (a) dietary supplementation, e.g., by an increase in the proline content of the diet (e.g., by nutritional supplements, e.g., "nutraceuitcals");
  (b) altered dietary compoisition, e.g., by an increase in the dietary content of arginine which can be converted to proline as required;
  (c) pharmacological therapy, e.g., by chronic treatment with paracetamol or with drugs designed to increase the activity of enzymes in the proline anabolic pathway; and/or,
  (d) gene therapy to modulate the activity of enzymes involved in proline metabolism or the metabolism of related amino acids (e.g., arginine or cysteine).

Dietary supplementation with proline may be particularly desirable in individuals who necessarily have a diet low in proline (e.g., vegetarians or individuals with restricted diets for religious or medical reasons).

Alternatively, or in addition, the individual is given amino acids or sources of amino acids (e.g., peptides or proteins) rich in amino acids that can be converted to proline, i.e., proline precursors, such as arginine, ornithine, citruline, glutamate, □-pyrolline-5-carboxylate, aminovalerate, and glutamine.

The individual is given the dietary supplement, for example, as a powder or a tablet, at a suitable dosage, in order to normalise serum proline levels. Serum proline levels may be monitored, e.g., using the methods described herein, during treatment. Typically an individual with low serum proline levels (below 220 µM) may be treated with 0.1 to 100 grams of proline per day, more typically between 1 and 10 grams per day. Such treatment would result in a sustained increase in serum proline levels to 250-300 µM in most individuals. Any excess dietary proline is excreted either as proline or as ▢-pyrroline-5-carboxylate in the urine.

Serum proline levels are also affected by the long-term use of paracetamol. Paracetamol, like other drugs which are cleared by conjugation with glutathione, and which are used at very high doses (often several grams a day) can significantly deplete the glutathione pool. Gluathione (which is a tripeptide consisting of glutamate, glycine and cysteine) synthesis increases and becomes rate-limited by dietary availability of cysteine. As a result, glutamate availability increases, and this is converted through Δ-pyrroline-5-carboxylate to proline.

Thus, another type of therapy is chronic treatment with paracetamol, or other drug which is eliminated by conjugation with glutathione. Such a treatment may be particularly desirable in individuals who cannot tolerate dietary supplementation with proline, or who are unable (for example, due to genetic defects) to convert arginine or ornithine into proline. The individual is given paracetamol at a dose sufficient to normalise serum proline levels. Serum proline levels may be monitored, e.g., using the methods described herein, during treatment. Typically, an individual with low serum proline levels (below 220 μM) may be treated with 0.1 to 5 grams of paracetamol per day, more typically between 2 and 5 grams per day. Such treatment would result in a sustained increase in serum proline levels to 250-300 μM in most individuals. Care must be taken not exceed the safe dose of paracetamol, which is set by the risk of liver damage at doses above 5 grams per day.

One aspect of the present invention pertains to a method of treatment of a condition associated with proline deficiency (e.g., a condition associated with low bone mineral density, e.g., osteoporosis), comprising chronic administration of paracetamol.

One aspect of the present invention pertains to use of paracetamol in the preparation of a medicament for the treatment of a condition associated with proline deficiency (e.g., a condition associated with low bone mineral density, e.g., osteoporosis).

Since cysteine metabolism and proline metabolism are intimately linked through the size of the glutathione pool (as illustrated by the impact of glutathione depletion during chronic paracetamol use), genetic disorders of cysteine metabolism are also linked to proline metabolism. Hyperhomocysteinemia is the result of one of two relatively common polymorphisms in genes encoding enzymes responsible for cysteine metabolism. Hyperhomocysteinemia is associated with a range of chonic illnesses, including atherosclerosis and osteoporosis. Consequently, the methods described bwlow for modulating proline metabolism would be expected to be useful in any disease manifesting itself as a result of hyperhomocysteinemia or other defects in cysteine metabolism.

Another therapy is chronic treatment with a drug known to increase the biosynthesis of proline. Such molecules can be identified by enzyme activity screening assays. For example, purified enzymes from proline biosynthesis pathways are exposed to drug candidates and a radiolabelled substrate (e.g., tritium labelled glutamate). The rate of production of labelled proline is monitored, and a candidate drug which causes increased rate of proline production is then identified as a potential therapeutic drug.

Genetic defects any of the enzymes involved in proline metabolism may also contribute to deficiency in the serum proline pool. Defects in gamma-glutamyl kinase, gamma-glutamyl phosphate reductase, ▢-pyrroline-5-carboxylate reductase, ornithine transaminase, ornithine cyclase (deaminating), proline oxidase, ▢-pyrroline-5-carboxylate dehydrogenase, proline racemase or D-proline reducase would all be expected to result in low serum proline (and hence osteoporosis). Inidividuals with low serum proline as a result of genetic defects, as opposed to dietary insufficiency, may be less responsive or unresponsive to dietary supplementation or other treatments with proline. Such individuals may require treatment with agents designed to increase proline biosynthesis via a pathway which has not been compromised by the genetic mutation.

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e., prophylaxis) is also included.

The term "therapeutically-effective amount," as used herein, pertains to that amount of an active compound, or a material, composition or dosage form comprising an active compound, which is effective for producing some desired therapeutic effect, commensurate with a reasonable benefit/risk ratio.

The term "treatment" includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy.

One aspect of the present invention pertains to methods of treatment (e.g., therapy) of a condition associated with a bone disorder, e.g., with low bone mineral density, e.g., osteoporosis, based upon normalisation of an observed proline deficiency in a patient, and the materials and/or compositions used in such methods.

One aspect of the present invention pertains to a method of treatment of and/or the prevention of (e.g., as a prophylaxis for) a condition associated with a bone disorder, e.g., with low bone mineral density, e.g., osteoporosis, comprising administration of a composition rich in proline, and/or free proline, and/or one or more proline precursors.

One aspect of the present invention pertains to a composition rich in proline, and/or free proline, and/or one or more proline precursors, for the treatment of and/or the prevention of (e.g., as a prophylaxis for) a condition associated with a bone disorder, e.g., with low bone mineral density, e.g., osteoporosis.

One aspect of the present invention pertains to use of a composition rich in proline, and/or free proline, and/or one or more proline precursors in the preparation of a medicament for the treatment of and/or the prevention of (e.g., as a prophylaxis for) a condition associated with a bone disorder, e.g., with low bone mineral density, e.g., osteoporosis.

In one embodiment, said composition rich in proline, and/or free proline, and/or one or more proline precursors is administered orally.

One aspect of the present invention pertains to a dietary supplement (e.g., nutraceutical) rich in proline, and/or free proline, and/or one or more proline precursors, for use in the treatment of and/or the prevention of (e.g., as a prophylaxis for) a condition associated with a bone disorder, e.g., with low bone mineral density, e.g., osteoporosis.

One aspect of the present invention pertains to use of a dietary supplement rich in proline, and/or free proline, and/or one or more proline precursors, in the treatment of and/or the prevention of (e.g., as a prophylaxis for) a condition associated with a bone disorder, e.g., with low bone mineral density, e.g., osteoporosis.

One aspect of the present invention pertains to a method of treatment of and/or the prevention of (e.g., as a prophylaxis for) a condition associated with a bone disorder, e.g., with low bone mineral density, e.g., osteoporosis, comprising administration of a dietary supplement rich in proline, and/or free proline, and/or one or more proline precursors.

In one embodiment, said dietary supplement rich in proline, and/or free proline, and/or one or more proline precursors is administered orally.

In one embodiment, said "proline, and/or free proline, and/or one or more proline precursors" is proline and/or free proline."

In one embodiment, said "proline, and/or free proline, and/or one or more proline precursors" is proline.

In one embodiment, said "proline, and/or free proline, and/or one or more proline precursors" is free proline.

In one embodiment, said "proline, and/or free proline, and/or one or more proline precursors" is one or more proline precursors.

One aspect of the present invention pertains to a method of therapy, especially of a condition associated with a bone disorder, e.g., with low bone mineral density, e.g., osteoporosis, based upon correction of metabolic defect in one or more of (a) proline synthesis, (b) proline transport, (c) proline absorption, and (d) proline loss mechanisms.

One aspect of the present invention pertains to a method of therapeutic monitoring of the treatment (e.g., therapy) of a patient having a condition associated with a bone disorder, e.g., with low bone mineral density, e.g., osteoporosis, comprising monitoring proline levels in said patient.

One aspect of the present invention pertains to a genetic test, and a method of genetic testing, for susceptibility to conditions associated with a bone disorder, e.g., with low bone mineral density, e.g., osteoporosis, based upon, for example, polymorphisms of, e.g., enzymes involved in proline metabolism, e.g., P5CDH, proline oxidase, P5C reductase, gamm-glutamyl kinase, gamm-glutamyl phosphate reductase and ornithine transaminase.

One aspect of the present invention pertains to the use of P5CHD, and/or associated enzymes and/or compounds involved in proline metabolism (e.g., P5CDH, proline oxidase, P5C reductase, gamm-glutamyl kinase, gamm-glutamyl phosphate reductase and ornithine transaminase), as a target for the identification of a compound (e.g., modulators, inhibitors, etc.) which is useful in the treatment of a condition associated with a bone disorder, e.g., with low bone mineral density, e.g., osteoporosis; for example, to prevent hydroxyproline mediated product inhibition of the P5CDH pathway.

One aspect of the present invention pertains to a method of identifying a compound (e.g., modulator, inhibitor, etc.) which is useful in the treatment of a condition associated with a bone disorder, e.g., with low bone mineral density, e.g., osteoporosis, and which employs an enzyme involved in proline metabolism (e.g., P5CDH, proline oxidase, P5C reductase, gamm-glutamyl kinase, gamm-glutamyl phosphate reductase and ornithine transaminase), and/or associated compounds, as a target.

One aspect of the present invention pertains to novel compounds so identified, which target an enzyme involved in proline metabolism, and/or associated compounds.

One aspect of the present invention pertains to a method of treatment, especially of a condition associated with a bone disorder, e.g., with low bone mineral density, e.g., osteoporosis, which involves administration of a compound so identified.

One aspect of the present invention pertains to a compound so identified for use in a method of treatment, especially of a condition associated with a bone disorder, e.g., with low bone mineral density, e.g., osteoporosis.

One aspect of the present invention pertains to a method of genetically modifying an animal, for example, so as to have a predetermined condition associated with a bone disorder (e.g., a predisposition towards low bone mineral disease, e.g., a predisposition towards osteoporosis), or, e.g., a deficiency in circulating free proline, for example, for use as animal models for bone disorder studies. For example, "knock-out animals," where one or more genes have been removed or made non-functional; "knock-in" animals, where one or more genes have been incorporated from the same or a different species; and in animals where the number of copies of a gene has been increased. For example, genetic medications involving one or more genes important and/or critical in proline metabolism (e.g., encoding P5CHD) may be used in the design of animals useful as animal models for conditions associated with a bone disorder, e.g., with low bone mineral density, e.g., osteoporosis.

One aspect of the present invention pertains to an animal so prepared.

One aspect of the present invention pertains to use of an animal so prepared for the development and/or testing of a treatment or therapy, e.g., in drug development, drug testing, etc.

EXAMPLES

The following are examples are provided solely to illustrate the present invention and are not intended to limit the scope of the present invention, as described herein.

Example 1

Osteoporosis

As discussed above, the inventors have developed novel methods (which employ multivariate statistical analysis and pattern recognition (PR) techniques, and optionally data filtering techniques) of analysing data (e.g., NMR spectra) from a test population which yield accurate mathematical models which may subsequently be used to classify a test sample or subject, and/or in diagnosis.

These techniques have been applied to the analysis of blood serum in the context of osteoporosis. The metabonomic analysis can distinguish between individuals with and without osteoporosis. Novel diagnostic biomarkers for osteoporosis have been identified, and methods for associated diagnosis have been developed.

Briefly, metabonomic methods were applied to blood serum sample for subjects in an osteoporosis study. Biomarkers, including free proline, were identified as being diagnostic for osteoporosis. Subsequently, proline levels were used to classify (e.g., diagnose) patients, specifically, by using predictive mathematical models which take account of free proline levels.

Collection of NMR Spectra

Analysis was performed on serum samples collected from subjects under study. Serum taken from control subjects (n=40) and patients with osteoporosis (n=29), prior to a formal diagnosis of bone disease.

The data were classified as "control" (triangle, ▲) or "osteoporosis" (circle, ●).

Osteoporosis was diagnosed according to bone mineral density (BMD) of the lumbar spine (LS), which was expressed as a Z-score. Osteoporosis in a subject was diagnosed using the World Health Organisation (WHO) definition of osteoporosis as a bone mineral density (BMD) which was below a cut-off value which was 1.5 standard deviations (SDs) below the age- and sex-matched mean (i.e., a Z-score of −1.5 or below) or by the presence of spinal fractures (see, e.g., World Health Organisation, 1994). Control subjects had a Z-score above this cut-off value and no history of fractures.

Blood was drawn from each patient, allowed to clot in plastic tubes for 2 hours at room temperature, and the serum was collected by centrifugation. Aliquots of serum were stored at −80° C. until assayed.

Prior to NMR analysis, samples (150 μl) were diluted with solvent solution (10% $D_2O$ v/v, 0.9% NaCl w/v) (350 μl). The diluted samples were then placed in 5 mm high quality NMR tubes (Goss Scientific Instruments Ltd).

Conventional 1-D $^1H$ NMR spectra of the blood serum samples were measured on a Bruker DRX-600 spectrometer using the conditions set forth in the section entitled "NMR Experimental Parameters."

NMR Experimental Parameters
(a) General:
Samples were NON-SPINNING in the spectrometer
Temperature: 300 K
Operating Frequency: 600.22 MHz
Spectral Width: 8389.3 Hz
Number of data points (TD): 32K
Number of scans: 64
Number of dummy scans: 4 (once only, before the start of the acquisition).
Acquisition time: 1.95 s
(b) Pulse Sequence:
noesypr1d (Bruker standard noesypresat sequence, as listed in their manual): RD-90°-$t_1$-90°-$t_m$-90°-FID
Relaxation delay (RD): 1.5 s
Fixed interval ($t_1$): 4 μs
Mixing time ($t_m$): 150 ms
90° pulse length: 10.9 μs
Total recycle period: 3.6 s
Secondary irradiation at the water resonance during RD and $t_m$
(c) Phase Cycling The phase of the RF pulses and the receiver was cycled on successive scans to remove artefacts according to the following scheme, where PH1 refers to the first 90° pulse, PH2 refers to the second, PH3 refers to the third and PH31 refers to the phase of the receiver. In the following scheme:
0 denotes 0° phase increment
1 denotes 90° phase increment
2 denotes 180° phase increment
3 denotes 270° phase increment
PH1=0 2
PH2=0 0 0 0 0 0 0 0 2 2 2 2 2 2 2 2
PH3=0 0 2 2 1 1 3 3
PH31=0 2 2 0 1 3 3 1 2 0 0 2 3 1 1 3
(d) Processing of the FIDs:
This was done using using XWINNMR (version 2.1, Bruker GmbH, Germany).
Automatic zero fill×2 at end of FID.
Line broadening by multiplying the FID by a negative exponential equivalent to a line broadening of +0.3 Hz.
Fourier transform.

(e) Processing of the NMR Spectra:
This was done using using XWINNMR (version 2.1, Bruker GmbH, Germany).
Spectrum peak phase adjusted manually using the zero and first order parameters PHC0, PHC1.
Baseline corrected manually using the command "basl." This allows the subtraction of baselines of various degrees of polynomial. The simplest is to subtract a constant to remove a DC offset and this was sufficient in the present case. In other cases, it can be necessary to subtract a straight line of adjustable slope or to subtract a baseline defined by a quadratic function. The possibility exists within the software for functions up to quartic in nature.

Once properly phased and baseline corrected, the full spectra showed a flat featureless baseline on both sides of the main set of signals (i.e., outside the range δ 0 to 10), and the peaks of interest showed a clear in-phase absorption profile.

$^1H$ NMR chemical shifts in the spectra were defined relative to that of the lactate methyl group (the middle of the doublet, taken to be at δ 1.33).
(f) Reduction of the NMR Spectra to Descriptors The $^1H$ NMR spectra in the region δ 10-δ 0.2 were segmented into 245 regions or "buckets" of equal length (δ 0.04) using AMIX (Analysis of MIXtures software, version 2.5, Bruker, Germany). The integral of the spectrum in each segment was calculated. In order to remove the effects of variation in the suppression of the water resonance, and also the effects of variation in the urea signal caused by partial cross solvent saturation via solvent exchanging protons, the region δ 6.0 to 4.5 was set to zero integral. The following AMIX profile was used:
command=bucket_I d_table
input-file=<namesfile>
output_file=<mydata.amix>
left_ppm=10
right_ppm=0.2
exclude1_left_ppm=6.0
exclude1_right_ppm=4.5
exclude2_left_ppm=(intentionally undefined)
exclude2_right_ppm=(intentionally undefined)
bucket_width=0.04
bucket_mode=0
bucket_scale_mode=3
bucket_multiplier=0.01
bucket_output_format=2
normalization_region_left=10
normalization_region_right=0.2

The integral data were normalized to the total spectral area using Excel (Microsoft, USA). Intensity was integrated over all included regions, and each region was then divided by the total integral and multiplied by a constant (i.e., 100, so that final integrated intensities are expressed as percentages of the total intensity).

The normalized data were then exported to the SIMCA-P (version 8.0 Umetrics, Sweden) software package and each descriptor was mean-centered. All subsequent analysis was therefore performed on normalised mean-centered data.
Data Analysis A Principal Components Analysis (PCA) model was calculated from the 1D $^1H$ NMR spectra of serum samples from control subjects (▲) and patients with osteoporosis (●). The corresponding scores and loadings plots are shown in FIG. 1A-OP and FIG. 1B-OP, respectively. Those regions of the NMR spectrum which are responsible for causing separation between the different samples are also indicated in FIG. 1B-OP. Separation between controls and osteoporosis is evident in PC2, with control samples dominating the lower two quadrants and osteoporosis samples dominating the upper two quadrants.

A Principal Components Analysis (PCA) model was calculated from the 1D $^1$H NMR spectra of serum samples from control subjects (▲) and patients with osteoporosis (●), but, in this case, prior to PCA, the data were filtered by application of orthogonal signal correction (OSC), which serves to remove variation that is not correlated to class and therefore improves subsequent data analysis. The corresponding scores and loadings plots are shown in FIG. 1C-OP and FIG. 1D-OP, respectively.

The improved separation between the control and osteoporosis samples is evident, with controls dominating the left hand side of the plot and osteoporosis dominating the right hand side. Note also, that application of OSC results in maximum variation being observed in PC1 rather than in PC2.

Improved separation is possible using PLS-DA (rather than the unsupervised PCA). A scores plot and the corresponding loadings plot is shown in FIG. 1E-OP and FIG. 4-1F-OP, respectively. Improved separation is evident, with controls dominating the right hand side of the plot and osteoporosis dominating the left hand side.

FIG. 2A-OP shows sections of the variable importance plots (VIP) and regression coefficient plots derived from the PLS-DA model described in FIG. 1E-OP.

FIG. 2B-OP shows a section of the regression coefficient plot derived from the PLS-DA model described in FIG. 1E-OP. In the regression coefficient plot, each bar represents a spectral region covering 0.04 ppm and shows how the $^1$H NMR profile of one control samples differs from the $^1$H NMR profile of a osteoporosis samples. A positive value on the x-axis indicates there is a relatively greater concentration of metabolite (assigned using NMR chemical shift assignment tables) and a negative value on the x-axis indicates a relatively lower concentration of metabolite.

The 10 most important chemical shift windows for the PLS-DA model are summarised in the following table. The assignments were made by comparing the loadings with published tables of NMR data.

TABLE 1-OP

| # | Bucket Region (ppm) | Assignment | Chem. Shift (ppm) and Multiplicity | NMR spectral intensity, in osteoporosis wrt control |
|---|---|---|---|---|
| 1 | 1.34 | predominantly lipid $CH_2CH_2CH_2CO$ | 1.32(m) | decreased* |
|   |      | also lactate $CH_3$ | 1.33(d) | increased* |
| 2 | 1.30 | lipid $CH_2$ | 1.30(m) | decreased |
| 3 | 1.26 | lipid $(CH_2)_n$, mainly LDL | 1.25(m) | decreased |
| 4 | 0.86 | lipid $CH_3$, mainly LDL, VLDL | 0.84(t) & 0.87(t) | decreased |
| 5 | 3.38 | proline half δ-$CH_2$ | 3.34(m) | decreased |
| 6 | 2.06 | proline half β-$CH_2$ | 2.05(m) | decreased |
| 7 | 2.02 | proline γ-$CH_2$ | 1.99(m) | decreased |
| 8 | 4.10 | lactate CH | 4.11(q) | increased |

TABLE 1-OP-continued

| # | Bucket Region (ppm) | Assignment | Chem. Shift (ppm) and Multiplicity | NMR spectral intensity, in osteoporosis wrt control |
|---|---|---|---|---|
| 9 | 3.34 | proline half δ-$CH_2$ | 3.34(m) | decreased |
| 10 | 3.22 | choline $N(CH_3)_3$ | 3.21(s) | decreased |

*Intensity changes of these overlapped peaks were determined by referral to the original $^1$H NMR spectra.

In summary, with respect to control samples, osteoporosis samples appear to have decreased levels of lipids, proline, choline, and 3-hydroxybutyrate, and increased levels of lactate, alanine, creatine, creatinine, glucose, and aromatic amino acids. Additional data for the buckets associated with these species are described in the following table. Again, the assignments were made by comparing the loadings with published tables of NMR data.

TABLE 2-OP

| Bucket Region (ppm) | Assignment | Chem. Shift (ppm) and Multiplicity | NMR spectral intensity, in osteoporosis wrt control* |
|---|---|---|---|
| lipid | | | |
| 1.34 | $CH_2CH_2CH_2CO$ | 1.32(m) | decreased |
| 1.30 | $CH_2$ | 1.30(m) | decreased |
| 1.26 | $(CH_2)_n$, LDL | 1.25(m) | decreased |
| 1.22 | $CH_3CH_2CH_2$ | 1.22(m) | |
| 0.86 | $CH_3$, LDL, VLDL | 0.84(t)&0.87(t) | decreased |
| proline | | | |
| 3.38 | half δ-$CH_2$ | 3.34(m) | decreased |
| 3.46 | half δ-$CH_2$ | 3.45(m) | decreased |
| 3.42 | half δ-$CH_2$ | 3.45(m) | decreased |
| 2.34 | half β-$CH_2$ | 2.36(m) | decreased |
| 2.06 | half β-$CH_2$ | 2.05(m) | decreased |
| 2.02 | γ-$CH_2$ | 1.99(m) | decreased |
| choline | | | |
| 3.22 | $N(CH_3)_3$ | 3.21(s) | decreased |
| 3.66 | $NCH_2$ | 3.66(m) | decreased |
| 3-hydroxybutyrate | | | |
| 4.14 | β-CH | 4.13(m) | decreased |
| 2.38 | half α-$CH_2$ | 2.38(m) | decreased |
| 2.30 | half α-$CH_2$ | 2.31(m) | decreased |
| 1.14 | γ-$CH_3$ | 1.20(d) | decreased |
| lactate | | | |
| 4.14 & 4.10 | CH | 4.11(q) | increased |
| 1.34 | $CH_3$ | 1.33(d) | increased |
| alanine | | | |
| 3.74 | α-CH | 3.76(q) | increased |
| 1.46 | $CH_3$ | 1.46(d) | increased |
| creatine | | | |
| 3.90 | $CH_2$ | 3.93(s) | increased |
| 3.02 | $CH_3$ | 3.04(s) | increased |
| creatinine | | | |
| 4.06 | $CH_2$ | 4.05(s) | increased |
| 3.06 | $CH_3$ | 3.05(s) | increased |

TABLE 2-OP-continued

| Bucket Region (ppm) | Assignment | Chem. Shift (ppm) and Multiplicity | NMR spectral intensity, in osteoporosis wrt control* |
|---|---|---|---|
| glucose | | | |
| 3.66-4.42 | various | 3.2-5.5 | increased |
| aromatic amino acids | | | |
| 7.00-8.00 | various | 7.00-8.00 | increased |

The intensity changes for the proline resonance at δ3.42 and δ3.46, the choline resonance at δ3.66, the lactate resonance at δ1.34 and the β-hydroxybutyrate resonance at δ4.14, all of which overlap with other peaks, were confirmed by referral to the original $^1$H NMR spectra.

Validation

Validation was performed using a y-predicted scatter plot. FIG. 3-OP shows the y-predicted scatter plot, and hence the ability of $^1$H NMR based metabonomics to predict class membership (control or osteoporosis) of unknown samples. Using ~85% of the control and osteoporosis samples, a PLS-DA model was constructed and used to predict the presence of disease in the remaining 15% of samples (the validation set). The y-predicted scatter plot assigns samples to either class 1 (in this case corresponding to control) or class 0 (in this case corresponding to osteoporosis); 0.5 is the cut-off. The PLS-DA model predicted the presence or absence of osteoporosis in 100% of cases, furthermore, for a four-component model, class can be predicted with a significance level ≧88%, using a 99% confidence limit.

Proline as Diagnostic Species/Biomarker

Following this analysis, the buckets designated 3.38, 2.06, 2.02, 3.34 were identified as having lower intensity in osteoporosis patient plasma as compared to control samples.

Re-examination of the original NMR spectra rather than the data-reduced, segmented files derived from them which are used for the statistical analysis, enables a visual inspection of the NMR peaks in those specific regions. Identification of the peak multiplicities in these regions leads a trained NMR spectroscopist to suggest free proline as the molecule responsible for the peaks. The fact that these peaks are spin-coupled to each other and hence are part of the same molecule comes from interpretation of the cross-peaks seen in a 2-dimensional COSY spectrum. The NMR peaks seen in the conventional 1-dimensional NMR spectrum are then compared visually with those of authentic proline dissolved in water at a comparable pH value. See, for example, Ellenberger et al., 1975; Lindon et al., 1999.

The regions 3.38 and 3.34 are both seen to include part of a multiplet at δ3.34 assignable to one of the protons of the δ-$CH_2$ pair of hydrogen atoms. The region designated 2.06 shows a resonance at δ2.05 identifiable as one of the protons from the β-$CH_2$ group. Similarly the region designated 2.02 contains a resonance at δ1.99 identified as one or both of the γ-$CH_2$ protons of proline (the chemical shift difference between the two γ protons is small). The peak multiplicity of each of these peaks is consistent with an authentic sample of proline measured under comparable conditions.

There are 4 other proton resonances for proline which should also show a change in level with osteoporosis if proline is a biomarker. These are the other β-, γ-, and δ-$CH_2$ protons at δ2.34, ~δ2.0, and δ3.45 respectively and the α-CH proton at δ4.14. Indeed, examination of the spectra shows that the intensity of the signals for the other β-$CH_2$ and δ$CH_2$ protons also correlate with the diagnosis. It is not possible to distinguish the other γ-$CH_2$ proton because its shift is close to the first γ-$CH_2$ proton and may already have been included above. Nor is it possible to observe the chemical shift of the α-CH proton because of spectral overlap.

Finally, confirmation that proline is the substance responsible for the diagnostic NMR peaks is obtained by adding a sample of authentic proline to a plasma sample and noting complete coincidence of all of the endogenous signals assigned to proline with those of the added proline.

The $^1$H NMR chemical shifts for all amino acids including proline are dependent on the solution pH because of the presence of the ionisable groups. In the case of proline, these are the carboxylic acid group (—COOH) and the secondary amine group (—NH—). Hence it is important to compare the NMR spectra of plasma with that of an authentic sample of proline at the same pH. This has been done as described above.

In addition, it is possible for amino acids to react with bicarbonate ion ($HCO_3^-$) in a biological sample to form carbamate adducts, i.e., formed between the amino acid amino group and the bicarbonate ion. The resulting adduct has different NMR chemical shifts to those of the parent amino acid. This problem has not been seen with proline specifically. However, this problem of changed chemical shifts can be overcome by adding authentic proline to the appropriate plasma sample and noting exact coincidence of all of the added proline proton peaks with those of the endogenous biomarker peaks.

Example 2

Application of Isatin Assay

As discussed above, peak assignment in the NMR study described above suggested that proline is particularly significant for distinguishing subjects with osteoporosis from subjects with normal bone mineral density.

This finding was confirmed using a novel high-throughput microtitre format assay for proline (also developed by the inventors) to the same serum samples used in the NMR study (subjects diagnosed with osteoarthritis were excluded from the data analysis). The independent biochemical assay data confirms that the differences in the NMR spectra attributed to proline are in fact due to proline.

Without wishing to be bound to any particular theory, the inventors postulate that low serum proline is associated with low bone mineral density through a causal link whereby proline deficiency slightly but significantly decreases the rate of synthesis of collagen, the key structural protein in bone.

The data are summarised in the following table.

| Variation in Serum Proline Levels | | |
|---|---|---|
| Proline Level (µM) | Controls (n) | Osteoporosis (n) |
| 51-75 | 0 | 0 |
| 76-100 | 0 | 1 (4%) |
| 101-125 | 0 | 1 (4%) |
| 126-150 | 0 | 1 (4%) |
| 151-175 | 2 (5%) | 4 (15%) |
| 176-200 | 3 (8%) | 4 (15%) |
| 201-225 | 4 (10%) | 7 (26%) |
| 226-250 | 7 (18%) | 5 (19%) |
| 251-275 | 10 (26%) | 2 (7%) |
| 276-300 | 4 (10%) | 1 (4%) |
| 301-325 | 3 (8%) | 0 |

-continued

Variation in Serum Proline Levels

| Proline Level (μM) | Controls (n) | Osteoporosis (n) |
|---|---|---|
| 326-350 | 2 (5%) | 1 (4%) |
| 351-375 | 2 (5%) | 0 |
| 376-400 | 2 (5%) | 0 |
| 401-425 | 0 | 0 |
| 426-450 | 0 | 0 |

Serum proline was lower in the individuals with osteoporosis (OP) as compared to controls, specifically, 226±11 μM in individuals with OP versus 258±9 μM in controls (p=0.03 Student's unpaired t-test with n=39 controls and n=28 OP subjects).

A statistically significant reduction in serum proline associated with low bone mineral density of about 10-20% was found (normal distribution), even for this relatively small group of subjects.

Example 3

Further Application of Isatin Assay

In an independent study of 865 women with OP (using the same WHO definition of osteoporosis as in the first study) and 612 women with normal bone mineral density, serum proline was found to be lower among women with osteoporosis, specifically, 211±4 μM in OP versus 252±3 μM in control subjects (p<0.001 Student's unpaired t-test).

Further analyses of these cohorts indicate that serum proline concentration is correlated with bone mineral density, even among healthy controls (r=0.271; p<0.0001 Spearman's rank correlation coefficient, versus lumbar spine bone mineral density from DEXA scan).

A similar correlation was seen with femoral neck bone mineral density (r=0.202; p<0.0001).

However, low serum proline was not significantly associated with the presence of clinical fracture (213±16 μM in those with fracture compared to 229±8 μM in those with OP defined by low bone mineral density but no fracture).

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention as defined by the appended claims.

REFERENCES

A number of patents and publications are cited above in order to more fully describe and disclose the invention and the state of the art to which the invention pertains. Full citations for these references are provided below. Each of these references is incorporated herein by reference in its entirety into the present disclosure.

Adams, E. & Grank, L., 1980, "Metabolism of Proline and the Hydroxyprolines," *Ann. Rev. Biochem.*, Vol. 49, pp. 1005-1061.

Ala-Korpela, M., Hiltunen, Y. and Bell, J. D., 1995, "Quantification of biomedical NMR data using artificial neural network analysis: Lipoprotein lipid profiles from H-1 NMR data of human plasma," *NMR Biomed.*, Vol. 8, pp. 235-244.

Andersen, C. A., 1999, "Direct orthogonalization," *Chemometrics and Intelligent Laboratory Systems*, Vol. 47, pp. 51-63.

Bocter, F. N., 1971, "An improved method for colorimetrix determination of Proline with isatin," *Analytical Biochemistry*, Vol. 43, pp. 66-70.

Claridge, T. D. W., *High-Resolution NMR Techniques in Organic Chemistry: A Practical Guide to Modern NMR for Chemists*, Oxford University Press, 2000.

Ensenat, D., Hassan, S. Reyna, S. Schaffer, A & Durante, W., 2001, "TGF-beta stimulates vascular smooth muscle cell L-proline transport by inducing system A amino acid tansporter 2 (SA2) gene expression," *Biochem. J.*, Vol., 360, pp. 507-512.

Eriksson, L., Johansson, E., Kettaneh-Wold, H., and Wold, S., 1999, *Introduction to Multi and Megavariate Analysis using Projection Methods (PCA & PLS)*, UMETRICS Inc. (Box 7960, SE90719 Umea, SWEDEN), pp. 267-296.

Fan, T. W.-M., 1996, "Metabolic profiling by one- and two-dimensional NMR analysis of complex mixtures," *Progress in NMR Spectroscopy*, Vol. 28, pp.161-219.

Fearn, T., 2000, "On orthogonal signal correction," *Chemometrics and Intelligent Laboratory Systems*, Vol. 50, pp. 47-52.

Felson D T et al., 2000, "Osteoarthritis: new insights," *Ann. Intern. Med.*, Vol. 133, pp. 635-646.

Felson D T, Zhang Y., 1998, "An update on the epidemiology of knee and hip osteoarthritis with a view to prevention," *Arthritis Rheum.*, Vol. 41, pp. 1343-1355.

Garnero P, Hausherr E, Chapuy M-C, Marcelli C, Grandjean H, Muller C et al., 1996, "Markers of bone resorption predic hip fracture in elderly women: the EPIDOS prospective study," *J. Bone Miner. Res.*, Vol. 11, pp. 1531-1538.

Guccione A A, Felson D T, Anderson J J, Anthony J M, Zhang Y, Wilson P W et al., 1994, "The effects of specific medical conditions on functional limitations of elders in the Framingham Study," *Am. J. Public Health*, Vol. 84, pp. 351-358.

Guyton A C., 1991, *A textbook of medical physiology*, Eighth edition. (publisher: W.B. Sauders, London), p. 881.

Hiltunen, Y., Heiniemi, E. and Ala-Korpela, M., 1995, "Lipoprotein lipid quantification by neural-network analysis of H-1 NMR data from human blood-plasma," *J. Mag. Res. Ser. B*, Vol. 106, pp. 191-194.

Hughes D E, Boyce B F, 1997, "Apoptosis in bone physiology and disease," *Mol. Pathol.*, Vol. 50(3), pp. 132-137.

Kowalski, B. R., Sharaf, M. and lllman D., *Chemometrics* (John Wiley & Sons, Chichester, 1986).

Kvalheim, O. M., Karstang, T. V., 1989, "Interpretation of latent-variable regression models," *Chemometrics and Intelligent Laboratory Systems*, Vol. 7, pp. 39-51.

Lindon, J. C., et al., 1999, "NMR spectroscopy of biofluids," in *Annual Reports on NMR Spectroscopy* (Webb, G. A., ed.), Academic Press (London), Vol. 38, pp. 1-88.

Melton L J, Chrischilles E A, Cooper C, Lane A W, Riggs B L, 1992, "Perspective: How many women have osteoporosis?," *J. Bone. Miner. Res.*, Vol. 7, pp. 1005-1010.

Mundy, G. R., 1996, *Bone Remodelling and its disorders* (2nd edition), London: Martin Dunitz Nicholson, J. K., et al., 1999, "Metabonomics—understanding the metabolic responses of living systems to pathophysiological stimuli via multivariate statistical analysis of biological NMR spectroscopic data," *Xenobiotica*, Vol. 29, pp. 1181-1189.

Pocock N A, Culton N L, Gilbert G R, Hoy M L, Babicheva R, Chu, J M, Lee K S, Freund J., 2000, "Potential roles for quantitative ultrasound in the management of osteoporosis," *Medical Journal of Australia*, Vol. 173 (7), pp. 355-358.

Prince R L, 2001, "How to diagnose the presence of osteoporosis and assess the risk of fracture," *Best Practice & Research in Clinical Rheumatology*," Vol. 15(3), pp. 345-358.

Promislow, J. H., Goodman-Gruen, D., Slymen, D. J. & Barrett-Connor, E., 2002, "Protein consumption and bone mineral density in the elderly: the Rancho Bernado Study," *Am. J. Epidemiol.*, Vol. 155, pp. 636-644.

Raisz, L. G., 1988, "Local and systemic factors in the pathogenesis of osteoporosis," *N. Engl. J. Med.*, Vol. 318, pp. 818-828.

Sjostrom, M., Wold, S., and Soderstrom, B., 1986, "PLS Discriminant Plots," *Proceedings of PARC in Practice*, Amsterdam, Jun. 19-21, 1985, Elsevier Science Publishers B.V., North Holland.

Stahle, L., and Wold, S., 1987, "Partial Least Squares Analysis with Cross-Validation for the Two-Class Problem: A Monte Carlo Study," *Journal of Chemometrics*, Vol. 1, pp. 185-196.

Stein W H, Beam A G, Moore S, 1954b, "The amino acid content of the blood and urine in Wilson's Disease," *J. Clin. Invest.*, Vol. 33, pp. 410-419.

Stein W H, Morre S, 1954a, "The free amino acids of human blood plasma," *J. Biol. Chem.*, Vol. 211, pp. 915-926.

Sun, J., 1997, "Statistical analysis of NIR data: data pretreatment," *Journal of Chemometrics*, Vol. 11, pp. 525-532.

Tanaka, Y, Minato, Y., Hasumura, Y. & Takeuchi, J., 1986, "Evaluation of hepatic fibrosis by serum proline and amino-terminal type III procollagen peptide levels in alcoholic patients," *Digestive Diseases and Sciences*, Vol. 31, pp. 712-717.

West, K A, Crabb, J W, 1989, In: *Techniques in Protein Chemistry* (T. E. Hugli, ed.) Academic Press, pp. 295-304.

Westerhuis, J. A., de Jong, S., Smilde, A. K., 2001, "Direct orthogonal signal correction," *Chemometrics and Intelligent Laboratory Systems*, Vol. 56, pp. 13-25.

Wise, B. M., Gallagher, N. B., 2001, http://www.eigenvector.com/MATLAB/OSC.html.

Wold, S., Antti, H., Lindgren, F., and Ohman, J., 1998, "Orthogonal Signal Correction of Near-infrared Spectra," *Chemometrics and Intelligent Laboratory Systems*, Vol. 44, pp. 175-185.

Wold, S., Kettaneh, N., Friden, H., and Holmberg, A., 1998, "Modelling and Diagnostics of Batch Processes and Analogous Kinetic Experiments," *Chemometrics and Intelligent Laboratory Systems*, Vol. 44, pp. 331-340.

World Health Organisation, 1994, "Assessment of fracture risk and its application to screening for postmenopausal osteoporosis," *WHO Technical Report Series* 843 (Geneva: WHO).

Yelin E., 1998, "The economics of osteoarthritis," in: *Osteoarthritis* (Eds. Brandt K D, Doherty M, Lohmander L S) (publisher: Oxford University Press, New York), pp. 23-30.

The invention claimed is:

1. A method of classifying a sample, said method comprising the steps of:
    obtaining a sample from a subject;
    determining the amount of, or relative amount of, one or more diagnostic species in the sample; and
    relating the amount of, or relative amount of, the one or more diagnostic species present in said sample, as compared to a control sample, with a predetermined condition associated with a bone disorder;
    wherein said predetermined condition is a predetermined condition associated with osteoporosis; and
    wherein said diagnostic species include free proline.

2. A method according to claim 1, wherein said relating with a predetermined condition is relating with the presence or absence of a predetermined condition.

3. A method according to claim 1, wherein said one or more diagnostic species is a single diagnostic species.

4. A method according to claim 1, wherein said one or more diagnostic species is a single diagnostic species, and is free proline.

5. A method according to claim 1, wherein said one or more diagnostic species is a plurality of diagnostic species.

6. A method according to claim 1, wherein said diagnostic species additionally include one or more selected from lipids, choline, 3-hydroxybutyrate, lactate, alanine, creatine, creatinine, glucose, and aromatic amino acids.

7. A method according to claim 1, wherein said relating is performed on the basis of an amount, or a relative amount, of each of a plurality of diagnostic species.

8. A method according to claim 1, wherein said relating is performed on the basis of a total amount, or a relative total amount, of a plurality of diagnostic species.

9. A method according to claim 1, wherein said predetermined condition is osteoporosis.

10. A method according to claim 1, wherein said predetermined condition is predisposition towards osteoporosis.

11. A method according to claim 1, wherein the sample is a blood sample or a blood-derived sample; a plasma sample; a serum sample; or a urine sample or a urine-derived sample.

12. A computer program encoded on a non-transitory computer readable medium, comprising a computer program means adapted to perform a method according to claim 1, when said program is run on a computer.

13. The method according to claim 1, further comprising classifying said subject based on the classification of said sample.

14. The method according to claim 1, further comprising diagnosing said subject based on the classification of said sample.

15. The method according to claim 1, further comprising prognosing said subject based on the classification of said sample.

16. A method, according to claim 1, wherein said relating the amount of, or relative amount is relating a decrease in the amount of, or relative amount as compared to a control sample.

17. A method according to claim 16, wherein said one or more diagnostic species is a single diagnostic species, and is free proline.

18. A method according to claim 16, wherein said one or more diagnostic species is a single diagnostic species.

19. A method according to claim 16, wherein said one or more diagnostic species is a plurality of diagnostic species.

20. A method of classifying a sample, said method comprising the steps of:
    obtaining a sample from a subject;
    determining the amount of, or relative amount of, one or more diagnostic species in the sample; and
    relating the amount of, or relative amount of, the one or more diagnostic species present in said sample, as compared to a control sample, with a predetermined condition associated with a bone disorder;
    wherein said predetermined condition is a predetermined condition associated with osteoporosis; and
    wherein said diagnostic species include free proline;

wherein determining the amount, or relative amount, of the one or more diagnostic species in the sample is performed by using an isatin assay; an enzyme assay; an enzyme assay employing P5CDH; an enzyme assay employing proline oxidase and P5CDH; or an enzyme assay employing proline racemase and D-proline reductase.

21. A method of classifying a sample, said method comprising the steps of:

obtaining a sample from a subject;

determining the amount of, or relative amount of, one or more diagnostic species in the sample; and relating the amount of, or relative amount of, the one or more diagnostic species present in said sample, as compared to a control sample, with a predetermined condition associated with a bone disorder;

wherein said predetermined condition is a predetermined condition associated with osteoporosis; and wherein said diagnostic species include free proline;

wherein determining the amount, or relative amount, of the one or more diagnostic species in the sample is performed by using chromatography; ion-exchange chromatography; or high pressure liquid chromatography (HPLC).

22. A method of classifying a sample, said method comprising the steps of:

obtaining a sample from a subject;

determining the amount of, or relative amount of, one or more diagnostic species in the sample; and relating the amount of, or relative amount of, the one or more diagnostic species present in said sample, as compared to a control sample, with a predetermined condition associated with a bone disorder;

wherein said predetermined condition is a predetermined condition associated with low bone mineral density; and wherein said diagnostic species include free proline.

* * * * *